US007304037B2

(12) United States Patent
Lerchen et al.

(10) Patent No.: US 7,304,037 B2
(45) Date of Patent: Dec. 4, 2007

(54) CYTOSTATIC CONJUGATES WITH INTEGRIN LIGANDS

(75) Inventors: Hans-Georg Lerchen, Leverkusen (DE); Jörg Baumgarten, Wuppertal (DE); Andreas Schoop, Mittelbiberach (DE); Markus Albers, Leverkusen (DE)

(73) Assignee: Bayer Akiengesellschaft, Leverkusen (DE)

( * ) Notice: Subject to any disclaimer, the term of this patent is extended or adjusted under 35 U.S.C. 154(b) by 229 days.

(21) Appl. No.: 10/096,120

(22) Filed: Mar. 8, 2002

(65) Prior Publication Data

US 2002/0193311 A1 Dec. 19, 2002

(30) Foreign Application Priority Data

Mar. 8, 2001 (EP) ................. 01105350

(51) Int. Cl.
 A61K 38/06 (2006.01)
 A61K 38/07 (2006.01)
 C07K 5/08 (2006.01)
 C07K 5/10 (2006.01)
(52) U.S. Cl. ............... 514/18; 514/283; 514/401; 514/539; 514/562; 530/330; 530/331; 530/345
(58) Field of Classification Search ............. 514/18, 514/283, 401, 539, 562; 530/330, 331, 345; 546/48; 548/333.1; 560/13, 34; 562/4, 562/430, 439
See application file for complete search history.

(56) References Cited

U.S. PATENT DOCUMENTS

| 4,757,072 | A | 7/1988 | Kabbe et al. ............... 514/257 |
| 4,975,278 | A | 12/1990 | Senter et al. .............. 424/94.3 |
| 4,980,343 | A | 12/1990 | Stella et al. .................. 514/18 |
| 5,464,796 | A | 11/1995 | Petersen et al. ............ 514/312 |
| 5,561,119 | A | 10/1996 | Jacquesy et al. .............. 514/34 |
| 5,955,100 | A | 9/1999 | Bosslet et al. ............. 424/450 |
| 6,271,342 | B1 | 8/2001 | Lerchen et al. ............ 530/322 |
| 6,291,503 | B1 | 9/2001 | Schoop et al. ............. 514/401 |

FOREIGN PATENT DOCUMENTS

| DE | 4229903 | 3/1994 |
| EP | 0511917 | 11/1992 |
| EP | 0516861 | 12/1992 |
| EP | 0520240 | 12/1992 |
| EP | 0595133 | 5/1994 |
| WO | 8807378 | 10/1988 |
| WO | 9602546 | 2/1996 |
| WO | 9631532 | 10/1996 |
| WO | 9810795 | 3/1998 |
| WO | 9851703 | 11/1998 |
| WO | 9951638 | 10/1999 |
| WO | 0041469 | 7/2000 |
| WO | 0069472 | 11/2000 |
| WO | 0117563 | 3/2001 |

OTHER PUBLICATIONS

De Marre, A., Soyez, H., Schacht, E., Shoaibi, M., Seymour, L., Rihova, B., "Synthesis and Evaluation of Macromolecular Prodrugs of Mitomycin C", J. of Controlled Release, 36:87-97 (1995).
Soyez, H., Seymour, L., Schacht, E., "Macromolecular Derivatives of N,N-di-(2-chloroethyl)-4-phenylene Diamine Mustard. 2. In Vitro Cytotoxicity and In Vivo Anticancer Efficacy", J. of Controlled Release, 57:187-196 (1999).
Kasafirek, E., Fric, P., Slaby, J., "Role of Amino Acid Residues in Chromogenic Substrates Cleaved by Pancreatic Elastase", Collection Czechoslovak Chem. Commun., 52:1625-1633 (1987).
Fields, G., "Integrins: Cell Adhesion Molecules in Cancer", Exp. Opin. Ther. Patents 8: 633-644, (1998).
Ashwell, G., Harford, J., "Carbohydrate-Specific Receptors of the Liver", Ann. Rev. Biochem., 51: 531-554 (1982).
Aminoff, D., Bruegge, W., Bell, W., Sarpolis, K., Williams, R., "Role of Sialic Acid in Survival of Erythrocytes in the Circulation: Interaction of Neuraminidase-Treated and Untreated Erythrocytes With Spleen and Liver at the Cellular Level", Proc. Natl. Acad. Sci. USA, 74: 1521-1524 (1977).
Haltiwanger, R., Lehrman, M., Eckhardt, A., Hill, R., "The Distribution and Localization of the Fucose-Binding Lectin in Rat Tissues and the Identification of a High Affinity Form of the Mannose/N-Acetylglucosamine-Binding Lectin in Rat Liver", J. Biol. Chem., 261: 7433-7439 (1986).
Jansen, R., Molema, G., Ching, T., Oosting, R., Harms, G., Moolenaar, F., Hardonk, M., Meijer, D., "Hepatic Endocytosis of Various Types of Mannose-Terminated Alburnins", J. Biol. Chem., 266: 3343-3348 (1991).
Wall, J., Wani, M., Cook, C., Palmer, K., McPhail, A., Sim, G., "Plant Antitumor Agents. I. The Isolation and Structure of Camptothecin, A Novel Alkaloidal Leukemia and Tumor Inhibitor from *Camptotheca acuminata*", J. Am. Chem. Soc., 88: 3888-3890 (1966).
Brooks, P., Montgomery, A., Rosenfeld, M., Reisfeld, R., Hu, T., Klier, G., Cheresh, D., "Integrin αvβ3 Antagonists Promote Tumor Regression by Inducing Apoptosis of Angiogenic Blood Vessels", Cell, 79: 1157-1164 (1994).
Brooks, P., Stromblad, S., Lemke, R., Visscher, D., Sarkar, F., Cheresh, D., "Antiintegrin αvβ3 Blocks Human Breast Cancer Growth and Angiogenesis in Human Skin", J. Clin. Invest., 96: 1815-1822 (1995).
Fitzpatrick, J., Garnett, M., "Design, Synthesis and *In Vitro* Testing of Methotrexate Carrier Conjugates Linked Via Oligopeptide Spacers", Anti-Cancer Drug Design, 10: 1-9 (1995).
March, J., Advanced Organic Chemistry, 3rd. Ed., John Wiley & Sons, pp. 370-371, 802-803, no date.

(Continued)

*Primary Examiner*—Jeffrey Edwin Russel

(57) ABSTRACT

The present invention relates to cytostatics which have a tumor-specific action as a result of linkage to $\alpha_v\beta_3$ integrin antagonists via preferred linking units which can be selectively cleaved by elastase, i.e. by an enzyme which can especially be found in tumor tissue. The preferred linking units provide sufficient stability of the conjugate of cytostatic and $\alpha_v\beta_3$ integrin antagonist in biological fluids and, at the same time, the desired intracellular action within tumor cells as a result of its specific enzymatic or hydrolytic cleavability with release of the cytostatic.

17 Claims, No Drawings

OTHER PUBLICATIONS

Jiang, J., Li, W., Przeslawski, R., Joullie, M., "Comparative Study of Selected Reagents for Carboxyl Activation", Tetrahedr. Lett., 34: 6705-6708 (1993).

Rodionow, W., Postovskaja, E., "The Mechanism of Formation of Beta-Aryl-Beta-Amino Fatty Acids by the Condensation of Aromatic Aldehydes With Malonic Acid and its Derivatives", J. Am. Chem. Soc., 51: 841-847 (1929).

Ishihara, K., Hanaki, N., Funahashi, M., Miyata, M., Yamamoto, H., "Tris (pentafluorophenyl) Boron as an Efficient, Air Stable, and Water Tolerant Lewis Acid Catalyst", Bull. Chem. Soc. Jpn., 68: 1721-1730 (1995).

Arlt, D., Bomer, B., Grosser, R., Lange, W., "New Chiral Polyamide Stationary Phases for Chromatographic Enantiomer Separation", Angew. Chem. Ed. Engl., 30: 1662-1664 (1991).

Kunz, H., Muller, B., Schanzenbach, D., "Diastereoselective Diels—Alder Reaction on Carbohydrate Matrices", Angew. Chem. Int. Ed. Engl., 26: 267-269 (1987).

Gabius, H.J., "Endogene Lektine in Tumoren und Ihre Mogliche Bedeutung Fur Diagnose und Therapie Von Krebserkrankungen",Onkologie, 12: 175-181 (1989).

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Peptide Linker

<400> SEQUENCE: 1

Ala Ala Pro Val
1

<210> SEQ ID NO 2
<211> LENGTH: 4
<212> TYPE: PRT
<213> ORGANISM: Artificial
<220> FEATURE:
<223> OTHER INFORMATION: Peptide Linker
<220> FEATURE:
<221> NAME/KEY: MISC_FEATURE
<222> LOCATION: (1)..(4)
<223> OTHER INFORMATION: X is Nva

<400> SEQUENCE: 2

Ala Ala Pro Xaa
1
```

CYTOSTATIC CONJUGATES WITH INTEGRIN LIGANDS

The present invention relates to cytostatics which have a tumour-specific action as a result of linkage to $\alpha_v\beta_3$ integrin antagonists via preferred linking units which can be selevtively cleaved by elastase, i.e. by an enzyme which can especially be found in tumour tissue. The preferred linking units provide sufficient stability of the conjugate of cytostatic and $\alpha_v\beta_3$ integrin antagonist in biological media, e.g. culture medium or serum and, at the same time, the desired intracellular action within tumour tissue as a result of its specific enzymatic or hydrolytic cleavability with release of the cytostatic.

Chemotherapy in cancer is accompanied by usually serious side effects which are to be attributed to the toxic action of chemotherapeutics on proliferating cells of other tissue types than tumour tissue. For many years, scientists have occupied themselves with the problem of improving the selectivity of active compounds employed. A frequently followed approach is the synthesis of prodrugs which are released more or less selectively in the target tissue, for example, by change of the pH (DE-A 42 29 903), by enzymes (e.g. glucuronidases; EP-A 511 917 and 595 133) or by antibody-enzyme conjugates (WO 88/07378; U.S. Pat. No. 4,975,278; EP-A 595 133). A problem in these approaches is, inter alia, the lack of stability of the conjugates in other tissues and organs, and in particular the ubiquitous active compound distribution which follows the extracellular release of active compound in the tumour tissue.

The marked lectin pattern on tumour cell surfaces (Gabius, Onkologie 12, 175 (1989)) opens up the fundamental possibility of addressing these specifically on tumour cells by linkage of appropriate carbohydrate units to cytostatics. This prospect is restricted by the fact that, even in other tissues, in particular in the liver, lectins having similar carbohydrate specificities (galactose, lactose, mannose, N-acetyl glucosamine, fucose etc.) occur (Ashwell et al., Annu. Rev. Biochem. 46, 531 (1982); Stahl et al., Proc. Natl. Acad. Sci. USA 74, 1521 (1977); Haltiwanger et al., J. Biol. Chem. 261, 7433–7439 (1986); Jansen et al., J. Biol. Chem. 266, 3343 (1991)). Accordingly, a marked concentration of active compound-containing glycoconjugates in the liver and other lectin-rich organs must be expected if, in this approach, carbohydrates are used without particular modification establishing a selectivity to tumour tissue.

The heterocyclic amine batracylin (1) shows a good antitumour action in various stomach cancer models (U.S. Pat. No. 4,757,072).

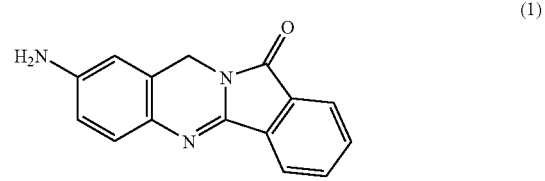

Peptide conjugates of (1) having good in-vitro action and more favourable solubility properties (U.S. Pat. No. 4,980,343) are more poorly tolerable in animal experiments than free batracylin. The fucose conjugates of batracylin (1) described in EP-A 501 250 disadvantageously concentrate very strongly in the liver.

Quinolone-a (2), 7-[(3a-R,S, 4-R,S, 7a-S,R)-4-amino-1,3,3a,4,7,7a-hexahydro-isoindol-2-yl]-8-chloro-1-cyclopropyl-6-fluoro-1,4-dihydro-4-oxo-3-quinoline carboxylic acid, also shows, in addition to its outstanding antibacterial activity, a very good activity against various tumour cell lines (EP-A 520 240, JP-A 04 253 973). However, considerable toxicological problems face it (e.g. genotoxicity, bone marrow toxicity, high acute toxicity in-vivo etc.).

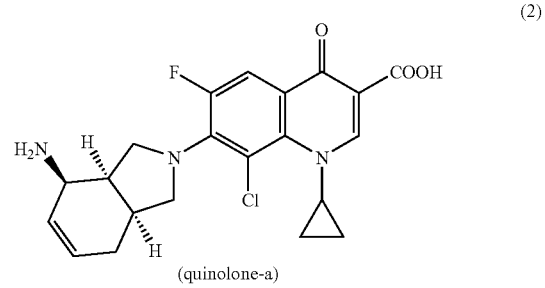

(quinolone-a)

20(S)-Camptothecin is a pentacyclic alkaloid which was isolated in 1966 by Wall et al. (J. Am. Chem. Soc. 88, 3888 (1966)). It has a high active antitumour potential in numerous in-vitro and in-vivo tests. Unfortunately, however, the realization of the promising potential in the clinical investigation phase failed because of toxicity and solubility problems.

By opening of the E ring lactone and formation of the sodium salt, a water-soluble compound was obtained which is in a pH-dependent equilibrium with the ring-closed form. Here too, clinical studies have not led to success as yet.

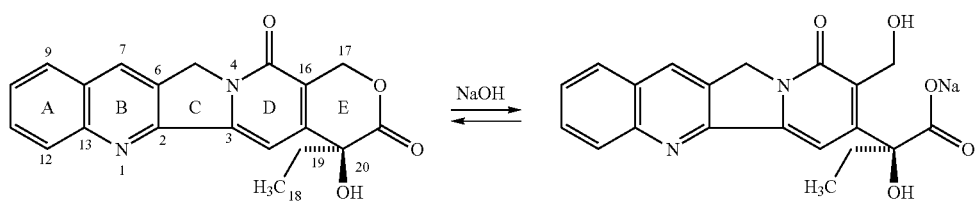

About 20 years later, it was found that the biological activity is to be attributed to enzyme inhibition of topoisomerase I. Since then, the research activities have again been increased in order to find a camptothecin derivative which is more soluble and more tolerable and which is active in-vivo.

For improvement of the water solubility, salts of A-ring- and B-ring-modified camptothecin derivatives and of 20-O-acyl derivatives with ionizable groups have been described (U.S. Pat. No. 4,943,579). The latter prodrug concept was later also transferred to modified camptothecin derivatives (WO 96/02546). The described 20-O-acyl prodrugs, however, have a very short half-life in vivo and are very rapidly cleaved to give the parent structure.

WO 96/31532 describes carbohydrate-modified cytostatics in which both serum stability and release of the cytostatic within the tumour cells and a specific concentration of the cytostatic in tumour tissue is achieved by a novel linkage of selectively modified carbohydrates to cytostatics (for example batracylin, quinolone-a, camptothecin) via preferred spacer and linker groups.

Integrins are heterodimeric transmembrane proteins found on the surface of cells, which play an important part in the adhesion of the cells to an extracellular matrix. They recognize extracellular glycoproteins such as fibronectin or vitronectin on the extracellular matrix via the RGD sequence occurring in these proteins (RGD is the single-letter code for the amino acid sequence arginine-glycine-aspartate).

In general, integrins such as, for example, the vitronectin receptor, which is also called the $\alpha_v\beta_3$ receptor, or alternatively the $\alpha_v\beta_5$ receptor or the GpIIb/IIIa receptor play an important part in biological processes such as cell migration, angiogenesis and cell-matrix adhesion and thus for diseases in which these processes are crucial steps. Cancer, osteoporosis, arteriosclerosis, restenosis and ophthalmia may be mentioned by way of example.

The $\alpha_v\beta_3$ receptor occurs, for example, in large amounts on growing endothelial cells and makes possible their adhesion to an extracellular matrix. The $\alpha_v\beta_3$ receptor thus plays an important part in angiogenesis, i.e. the formation of new blood vessels, which is a crucial prerequisite for tumour growth and metastasis formation in carcinomatous disorders.

It was possible to show that the blockade of the above-mentioned receptors is an important starting point for the treatment of disorders of this type. If the adhesion of growing endothelial cells to an extracellular matrix is suppressed by blocking their corresponding integrin receptors, for example, by a cyclic peptide or a monoclonal antibody, angiogenesis does not occur, which leads to a stoppage or regression of tumour growth (cf., for example, Brooks et al. in Cell 79, 1157–1164 (1994)).

Moreover, the invasive properties of tumour cells and thus their capability to form metastases markedly decrease when their $\alpha_v\beta_3$ receptor is blocked by an antibody (Brooks et al. in J. Clin. Invest. 96, 1815 (1995)).

WO 98/10795 describes conjugates in which a molecule adding to tumours is linked to a functional unit such as, for example, a cytostatic or a detectable label such as, for example, a radioactive nuclide. Inter alia, integrin antagonists such as, for example, peptides having the RGD sequence described above are described as molecules adding to tumours. Doxorubicin is described as an example of a cytostatic which is linked to a molecule of this type addressing tumours.

In the case of the compounds of WO 98/10795, the linkage is carried out such that the molecule addressing a tumour and the functional unit are directly bonded to one another with retention of their respective properties (cf., for example, p. 56, l. 17, to p. 58, l. 10, and Ex. 6). This has the result that these compounds are indeed selectively concentrated in the immediate vicinity of tumour cells by binding of the entity addressing a tumour (in the case of a radical having $\alpha_v\beta_3$ integrin-antagonistic action by binding to the $\alpha_v\beta_3$ integrin receptor which, in particular, is expressed on endothelial cells newly formed by angiogenesis), but on account of the direct combination the functional unit such as, for example, a cytostatic cannot be released into the intracellular space of the tumour tissue.

Fundamentally, the conjugate which on the one hand is selectively concentrated in tumour tissue by the effect of a part addressing $\alpha_v\beta_3$ or $\alpha_v\beta_5$ integrin receptors found in the conjugate, but on the other hand comprises a cytostatic which can be released from the conjugate, should have an increased toxophoric effect on tumour tissue due to the possibility of the more direct action of the cytostatic on the tumour cells compared with the conjugates described in WO 98/10795. In particular, such a toxophoric effect and tumour selectivity should even be higher, if the release of the cytostatic takes place in the immediate vicinity of the tumour tissue or even in the tumour cells.

In principle, medicament-containing conjugates are complex, difficult-to-prepare compounds, as is explained, for example, in Anti-Cancer Drug Design 10, 1–9 (1995), in particular p. 1. This article describes conjugates of the cytostatic methotrexate, an oligopeptide spacer, and a protein (human serum albumin). However, it is also pointed out (cf. p. 7, first paragraph) that the nature of the linking unit and the type of linkage of this unit to the toxophore and the carrier (for example an antibody) can affect the cleavage of the linking unit. This article therefore teaches that the linkage presented there cannot be transferred to other conjugate systems without difficulty. In particular, nothing is said about whether moieties addressed also to $\alpha_v\beta_3$ integrin receptors in this manner can be linked to toxophores without the moiety addressing $\alpha_v\beta_3$ integrin receptors by this means losing its ability to bind to $\alpha_v\beta_3$ integrin receptors.

The linking units disclosed in WO 96/31532 are used specifically for the linkage of a toxophore to a mono- or oligosaccharide radical. Nothing is said about whether moieties addressed also to $\alpha_v\beta_3$ integrin receptors can be linked to toxophores in this manner, without, by this means, the moiety addressing $\alpha_v\beta_3$ integrin receptors losing its ability to bind to $\alpha_v\beta_3$ integrin receptors.

In WO 00/69472 enzyme-activated anti-tumour prodrug compounds are disclosed which can be specifically cleaved by collagenase (IV) and elastase. With respect to linking units cleavable by elastase this application describes that the specific tetrapeptide sequences Ala-Ala-Pro-Val (SEQ ID NO: 1) and Ala-Ala-Pro-Nva (SEQ ID NO: 2) are suitable therefore. Furthermore, in this reference, no conjugates which comprise a moiety addressing $\alpha_v\beta_3$ integrin receptors and a cytostatic are mentioned.

It was therefore one object of the present invention to develop conjugates which comprise a moiety addressing $\alpha_v\beta_3$ integrin receptors and a cytostatic which can be released from the conjugate preferably at least in the vicinity of tumour tissue, where the moiety in the conjugate addressing $\alpha_v\beta_3$ integrin receptors retains its ability to bind to the $\alpha_v\beta_3$ integrin receptor and therefore provides tissue selectivity to such compounds.

The above object is achieved by conjugates which comprise a non-peptide moiety addressing $\alpha_v\beta_3$ integrin receptors, a cytostatic and a linking unit which is selevtively enzymatically cleavable with release of the cytostatic by elastase, i.e. by an enzyme which can especially be found in tumour tissue.

According to the present invention, it has surprisingly been found that a linking unit which is a peptide radical based on three specific amino acid residues can be selectively cleaved by the tumour-associated enzyme elastase or an elastase-like activity. Since advantageously the bond between this specific linking unit and the cytostatic is cleaved by elastase, the cytostatic is directly released. This leads to an increase in the tissue specificity of the conjugates according to the invention and thus to an additional decrease of toxicity of the conjugates according to the invention in other tissue types.

According to a further preferred embodiment of the invention, the linking unit can be cleaved by enzymes which are coupled to antibodies with selectivity for tumour tissue and are thus addressed to tumour tissue. This is also called the ADEPT approach. This likewise leads to a further increase in the tissue specificity of the conjugates according to the invention and thus to an additional decrease of the conjugates according to the invention in other tissue types.

The present invention concerns conjugates of the formula $$CT-LI-Sp_x-IA \quad (I)$$

wherein

CT denotes a monovalent radical from the group of a cytotoxic radical, a radical of a cytostatic and a radical of a cytostatic derivative, which can each additionally carry hydroxyl, carboxyl or amino group, LI denotes a bivalent peptide radical of the formula

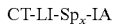

wherein independently of one another each of the radicals AA1 to AA4 represents an amino acid residue in the D- or L-configuration, which can each optionally carry protective groups, and q denotes zero or 1, Sp denotes a carbonyl or a thiocarbonyl group, x is zero or 1, IA denotes a monovalent non-peptide radical addressing an $\alpha_v\beta_3$ integrin receptor, which radical corresponds to the formula

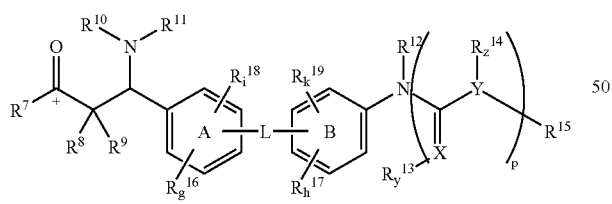

wherein the bond between radical (II) and SP (if x=1) or LI (if x=zero) is located as one of the following alternatives:

a) between radical (II) and LI via the carbon atom which in formula (II) is marked with a cross, b) between radical (II) and SP or LI
  (i) via Y (possible only, if p 1),
  (ii) (ii) via the nitrogen atom, to which $R^{10}$ is attached or—preferably
  (iii) via $R^{10}$, in which formula (II)

$R^7$ denotes hydroxyl, substituted or unsubstituted alkoxy, substituted or unsubstituted cycloalkoxy, substituted or unsubstituted aryloxy, or saturated or unsaturated, optionally substituted heterocyclyloxy or represents a single bond, in case the radical (II) is bonded to the rest of the conjugate directly via the carbon atom marked with a cross;

$R^8$ denotes hydrogen, hydroxyl, substituted or unsubstituted alkyl or alkoxy, substituted or unsubstituted cycloalkyl, substituted or unsubstituted aryl, saturated or unsaturated, substituted or unsubstituted heterocyclyl, substituted or unsubstituted alkenyl, substituted or unsubstituted alkinyl, or together with (i) $R^9$ and (ii) the carbon atom, to which $R^8$ is bonded, forms a substituted or unsubstituted carbocycle or heterocycle;

$R^9$ denotes hydrogen, hydroxyl, substituted or unsubstituted alkyl or alkoxy, substituted or unsubstituted cycloalkyl, substituted or unsubstituted alkenyl, substituted or unsubstituted alkinyl, substituted or unsubstituted aryl, saturated or unsaturated, substituted or unsubstituted heterocyclyl, or together with (i) $R^8$ and (ii) the carbon atom, to which $R^9$ is bonded, forms a substituted or unsubstituted carbocycle or heterocycle;

$R^{10}$ denotes a) one of the monovalent groups of $-SO_2R^{101}$, $-CO-R^{101}$, $-CO-OR^{102}$, $-CO-NR^{101}R^{103}$, $-CS-NR^{101}R^{103}$ in case the radical (II) is bonded to the rest of the conjugate directly via the carbon atom marked with a cross or via Y, or b) one of the bivalent groups of $-SO_2R^{101}$, $-CO-R^{101}$, $-CO-OR^{102}$, $-CO-NR^{101}R^{103}$, $-CS-NR^{101}R^{103}$ in case the radical (II) is bonded to the rest of the conjugate via $R^{10}$, or c) a single bond in case the radical (II) is bonded to the rest of the conjugate via the nitrogen atom, to which $R^{11}$ is bonded;

$R^{101}$ denotes a) substituted or unsubstituted alkyl, substituted or unsubstituted cycloalkyl, substituted or unsubstituted aryl, or saturated or unsaturated, substituted or unsubstituted heterocyclyl, in case the radical (II) is not bonded to the rest of the conjugate via $R^{101}$; or b) a bivalent group selected from substituted or unsubstituted alkylene, substituted or unsubstituted cycloalkylene, substituted or unsubstituted arylene, and saturated or unsaturated, substituted or unsubstituted heterocyclo-diyl, in case the radical (II) is bonded to the rest of the conjugate via $R^{101}$, $R^{102}$ denotes a) a monovalent group selected from substituted or unsubstituted alkyl, substituted or unsubstituted cycloalkyl, substituted or unsubstituted aryl, or saturated or unsaturated, substituted or unsubstituted heterocyclyl, in case the radical (II) is not bonded to the rest of the conjugate via $R^{102}$, or b) a bivalent group selected from substituted or unsubstituted alkylene, substituted or unsubstituted cycloalkylene, substituted or unsubstituted arylene, or saturated or unsaturated, substituted or unsubstituted heterocyclo-diyl, in case the radical (II) is bonded to the rest of the conjugate via $R^{102}$;

$R^{103}$ denotes hydrogen or one of the meanings of $R^{101}$, $R^{11}$ denotes (i) hydrogen, (ii) substituted or unsubstituted alkyl, (iii) the radical of a saturated or unsaturated (non-aromatic or aromatic) cyclic compound which can contain up to 4 hetero atoms per molecule or (iv) alkyl, substituted with a radical of group (iii) above;

L denotes $-(CH_2)_n NHSO_2(CH_2)_o-$, $-(CH_2)_n SO_2 NH(CH_2)_o-$, $-(CH_2)_n NH-CO(CH_2)_o-$, $-(CH_2)_n CONH(CH_2)_o-$, $-(CH_2)_n O-CH_2 (CH_2)_o-$, $-(CH_2)_n CH_2 O(CH_2)_o-$, $-(CH_2)_n COO (CH_2)_o-$, $-(CH_2)_n OOC-(CH_2)_o-$, $-(CH_2)_n CH_2 CO(CH_2)_o-$, $-(CH_2)_n-COCH_2(CH_2)_o-$, $-NHCONH-$, $-(CH_2)_n SCH_2(CH_2)_o-$, $-(CH_2)_n CH_2 S(CH_2)_o-$, $-(CH_2)_n CH_2 SO (CH_2)_o-$, $-(CH_2)_n SO-CH_2(CH_2)_o-$, $-(CH_2)_n CH_2-SO_2(CH_2)_o-$ or $-(CH_2)_n-SO_2CH_2 (CH_2)_o-$, wherein n and o denote zero or 1 and wherein $n+o \leq 1$;

$R^{12}$ denotes hydrogen, substituted or unsubstituted alkyl, substituted or unsubstituted cycloalkyl, substituted or unsubstituted aryl, or saturated or unsaturated, substituted or unsubstituted heterocyclyl, or together with (i) one of $R^{15}$ (if present), $R^{13}$ or $R^{14}$ and (ii) the nitrogen atom, to which $R^{12}$ is bonded, forms saturated or unsaturated, substituted or unsubstituted heterocyclyl which can contain further hetero atoms;

X denotes N, O or S;

y denotes zero, if X=O or S, and denotes 1, if X=N;

$R^{13}$ denotes hydrogen, substituted or unsubstituted alkyl, substituted or unsubstituted cycloalkyl, cyano, nitro, $-CO-R^{104}$ or $-CO-OR^{105}$, or together with (i) X and (ii) one of $R^{12}$, $R^{14}$ or $R^{15}$ forms substituted or unsubstituted heterocyclyl which can contain further hetero atoms;

$R^{104}$ denotes hydrogen, substituted or unsubstituted alkyl, substituted or unsubstituted cycloalkyl, substituted or unsubstituted aryl, or saturated or unsaturated, substituted or unsubstituted heterocyclyl which can contain further hetero atoms;

$R^{105}$ denotes hydrogen or one of the meanings of $R^{104}$;

Y denotes N or S;

$R^{14}$ denotes (i) hydrogen, (ii) substituted or unsubstituted alkyl, (iii) the radical of a saturated or unsaturated (non-aromatic or aromatic) cyclic compound which can contain up to 4 hetero atoms per molecule or (iv) alkyl, substituted with a radical of group (iii) above; or together with (i) Y and (ii) one of $R^{15}$ (if present), $R^{12}$ or $R^{13}$ forms a saturated or unsaturated, substituted or unsubstituted heterocyclyl which can contain further hetero atoms;

z denotes zero, if Y=S, and denotes 1, if Y=N;

p denotes zero or 1;

$R^{15}$ denotes hydrogen, substituted or unsubstituted alkyl, substituted or unsubstituted cycloalkyl, substituted or unsubstituted aryl, or saturated or unsaturated, substituted or unsubstituted heterocyclyl or together with (i) Y and (ii) one of $R^{14}$ (if p=z=1), $R^{12}$, or $R^{13}$ forms saturated or unsaturated, substituted or unsubstituted heterocyclyl which can contain further hetero atoms, or represents a single bond in case the radical (II) is bonded to the rest of the conjugate via Y;

$R^{16}$ to $R^{19}$ independently from each other denote cyano, halogen, substituted or unsubstituted alkyl or alkoxy, or substituted or unsubstituted cycloalkyl; and g, h, i, and k independently from each other denote zero or 1;

and their stereoisomers, their hydrates, their physiologically acceptable salts and the hydrates of these salts.

In this specification, bivalent substituents are indicated such that their respective left end is connected to the group indicated left of the corresponding substituent in formula (II) and their respective right end is connected to the group indicated right of the corresponding substituent in formula (II). If, for example, the radical L in formula (II) stands for $-(CH_2)_n NH-SO_2(CH_2)_o-$, the nitrogen atom is connected via the group $(CH_2)_n$ to the phenylene A in formula (II).

In the conjugates (I) according to the invention, radicals of quinolone-a or of camptothecin or of derivatives of camptothecin are preferred toxophore radicals CT; they can be linked to the rest of the conjugate via the oxygen atom (which in camptothecin is part of a hydroxyl group) at the $C_{20}$-carbon atom or via a functional group which is optionally present. Preferred examples of camptothecin derivatives include A- and B-ring-substituted camptothecins such as, for example, 9-amino-camptothecin, hydroxyl-substituted camptothecins such as, for example, 10-hydroxy camptothecin, and derivatives such as, for example, 10.11-methylenedioxy and 10.11-ethylenedioxy camptothecins, 7-substituted camptothecins such as, for example, 7-ethyl-10-hydroxy camptothecin, and homocamptothecins which in addition can carry substituents on the A- and/or the B-ring (O. Lavergne et al., J. Med. Chem. 41, 5410 (1998)). For the purpose of this invention, 20(R)- and 20(S)-camptothecin (derivatives) or mixtures thereof can be used. The 20(S)-configuration is preferred.

The term "amino acids" in the context of group LI in particular refers to the α-amino acids occurring in nature, but moreover also includes their homologues, isomers and derivatives. The term "derivatives" includes, for example, amino acids provided with protective groups. The amino acid radicals within the radical LI can each be linked to one another and to the radicals CT, Sp or IA via their carboxyl or amino functions. AA1 to AA4 independently from each other represent an amino acid residue in the D- and/or L-configuration. The residues of the naturally occurring amino acids glycine, alanine, valine, leucine, isoleucine, norvaline, serine, threonine, cysteine, S-methyl cysteine, ornithine, methionine, aspartate, glutamate, asparagine, glutamine, arginine, lysine, histidine, tryptophan, phenyl alanine, tyrosine, and proline are preferred. The L-configuration is particularly preferred.

According to the present invention, AA1 preferably is the residue of a naturally occurring amino acid in the D- or L-configuration selected from glycine, alanine, valine, leucine, isoleucine, histidine, glutamate, aspartate, serine, lysine, ornithine and phenyl alanine.

According to the present invention, AA2 preferably is the residue of a naturally occurring amino acid in the D- or L-configuration selected from alanine, valine, phenyl alanine, tyrosine, threonine, serine, isoleucine, lysine, glutamate, histidine, glycine, arginine, asparagine, glutamine, S-methyl cysteine, methionine, aspartate, tryptophane, proline, ornithine and leucine. The L-configuration is preferred; AA2 most preferably is a proline residue.

According to the present invention, AA3 and AA4 (if q=1) independently from each other preferably are the residues of a naturally occurring amino acid in the D- or L-configuration selected from alanine, valine, phenyl alanine, tyrosine, serine, isoleucine, lysine, glutamate, glutamine, histidine, glycine, arginine, asparagine, aspartate, tryptophane, proline, ornithine, methionine, S-methyl cysteine, norvaline and leucine. The L-configuration is preferred; AA3 and AA4 (if q=1) respectively most preferably are residues of an amino acid selected from alanine, norvaline, histidine, glycine, asparagine and aspartate.

Preferred conjugates (I) are those LI denotes a group of the formula -AA1-AA2-AA3-AA4$_q$- (III), wherein each of the amino acid radicals of LI is selected from the above groups.

The linking unit is preferably formed from the LI radical comprising three or four amino acid residues AA1 to AA3 or AA4 (if q=1) respectively and the radical Sp; it is possible, in particular, for the unit AA2 and AA3/AA4 to be modified on the side chain by protective groups. In these cases, the linkage to the radical CT as a rule takes place via the carboxyl function of the amino acid AA1, and the linkage to the IA radical directly or via the Sp radical takes place using an amino, a hydroxyl or a carboxyl group of the unit IA.

In the case in which the linkage is to take place via a carboxyl function of the unit IA, it is preferred, however, to use linking units without the unit Sp. In this case, the linkage between the radicals LI and IA can take place via an amino function of an amino acid which is part of LI.

Particularly preferred conjugates (I) are those wherein LI denotes a bivalent group of the above formula (III), wherein
  AA1 denotes a bivalent residue of valine, leucine or isoleucine;
  AA2 denotes a bivalent proline residue,
  AA3/AA4 independently from one another denote a bivalent residue of alanine, norvaline, histidine, glycine, asparagine or aspartate,
  q denotes zero or 1,
  and the radicals CT, Sp and IA are as defined above, and their stereoisomers, their hydrates, their physiologically acceptable salts and the hydrates of these salts.

In the case of amino acids having functional groups in the side chains, these functional groups can be free or protected by conventional protective groups used in peptide chemistry. Protective groups employed for the functional groups of amino acids include, for example, groups of the urethane, alkyl, acyl, ester or amide type. They preferably include benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitrobenzyloxycarbonyl, 2-nitro-4,5-dimethoxybenzyloxycarbonyl, methoxycarbonyl, ethoxycarbonyl, tert.-butoxycarbonyl (Boc), allyloxycarbonyl, vinyloxycarbonyl, 3,4,5-trimethoxybenzyloxycarbonyl, phthaloyl, 2,2,2-trichloroethoxycarbonyl, 2,2,2-trichloro-tert.-butoxycarbonyl, menthyloxycarbonyl, 4-nitrophenoxycarbonyl, fluorenyl-9-methoxycarbonyl (Fmoc), formyl, acetyl, propionyl, pivaloyl, 2-chloroacetyl, 2-bromo-acetyl, 2,2,2-trifluoro-acetyl, 2,2,2-trichloro-acetyl, benzoyl, benzyl, 4-chlorobenzoyl, 4-bromobenzoyl, 4-nitrobenzoyl, phthalimido, isovaleroyl, benzyloxymethylene, 4-nitrobenzyl, 2,4-dinitrobenzyl, 4-nitrophenyl and 2-nitrophenylsulphenyl. Fmoc and Boc are particularly preferred.

The removal of protective groups in appropriate reaction steps can be effected, for example, by the action of acid or base, hydrogenolytically or reductively in another manner.

The radicals (i) $R^{12}$ and $R^{13}$ or (ii) $R^{12}$ and $R^{14}$ or (iii) $R^{13}$ and $R^{14}$ or (iv) $R^{14}$ and $R^{15}$ or (v) (if p=zero) $R^{12}$ and $R^{15}$ can be connected to one another and thus together with X and/or Y form a heterocyclic ring system based on the following radicals:

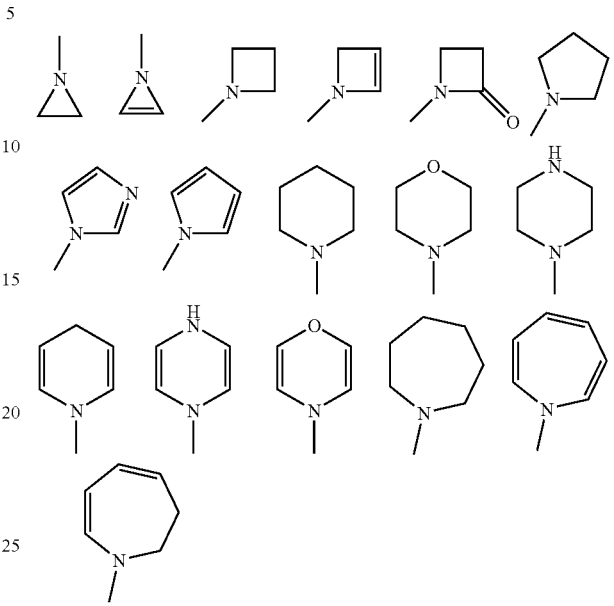

Of the ring systems shown above, the 4- to 6-membered ring systems are preferred.

As mentioned above, the group —N($R^{12}$)[C(=X$R^{13}$$_y$)Y$R^{14}$$_z$]$_p$$R^{15}$, the amino, urea, thiourea or guanidine unit can be acyclic or incorporated into a cyclic system and thus be a constituent of one of the following preferred functional units:

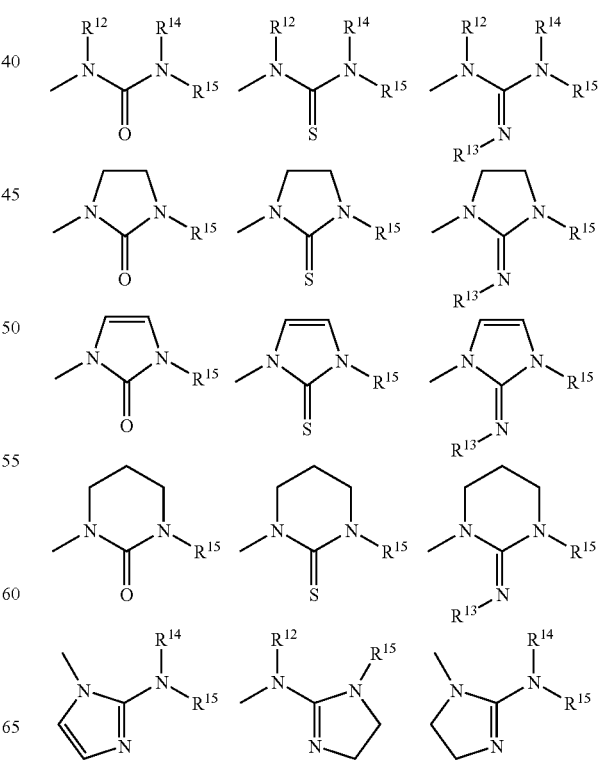

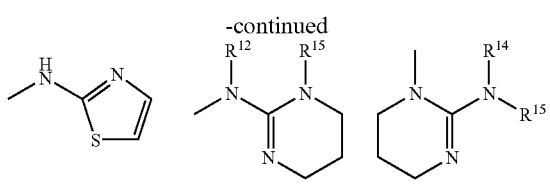

where the above list represents a non-exclusive enumeration of possible structural units.

In addition to the above-mentioned preferred structural units, their analogues, in which one or more 4- to 6-membered ring systems are fused to the heterocycle, such as, for example, the corresponding benzo-fused analogues of the above structural units, are also included.

Particularly preferred are radicals (II) whose central (phenylene A-linker L-phenylene B) unit contains a m-substituted phenylene unit A and a m-substituted phenylene unit B. According to the invention, the nitrogen atom to which $R^{10}$ and $R^{11}$ are attached is particularly preferably substituted by —$SO_2R^{101}$, —$COR^{101}$, —CO—$OR^{102}$, —$CONR^{101}R^{103}$ or $CSNR^{101}R^{103}$, wherein $R^{101}$, $R^{102}$ and $R^{103}$ are as defined above. In particular, radicals (II) are preferred in which $R^8=R^9=$hydrogen and $R^{10}$ does not represent a single bond.

Preferably, the linker group L is —$NHSO_2$—, —$CH_2NHSO_2$—, —$NHSO_2CH_2$—, —$OCH_2$—, —$CH_2O$—, —$CH_2OCH_2$—, —$CH_2CH_2O$— or —$OCH_2CH_2$—, and the radical found on the phenylene unit B is an acyclic or cyclic guanidine unit; cyclic guanidine units such as, for example, 4,5-dihydro-1H-imidazol-2-ylamino are particularly preferred.

Further particularly preferred conjugates (I) are those wherein

CT denotes the radical of camptothecin or a camptothecin derivative, which is formally formed by the abstraction of the hydrogen atom from the hydroxyl group at its $C_{20}$-carbon atom or from a functional group present in the molecule such as an amino or a hydroxy group;

LI and Sp are as defined above; and

IA is a non-peptide radical of the formula (II) addressing an $\alpha_v\beta_3$ integrin receptor, wherein $R^7$ denotes methoxy, ethoxy, propoxy, isopropoxy, butoxy, isobutoxy, tert.-butoxy, pentoxy, isopentoxy, neopentoxy, hexoxy, cyclopropoxy, cyclopropylmethoxy, cyclobutoxy, cyclopentoxy, cyclohexoxy, phenoxy, tolyloxy, benzyloxy, or a substituted derivative thereof or, preferably, hydroxyl or a single bond (in case the radical (II) is bonded to the rest of the conjugate via the carbon atom marked with a cross);

$R^8$ denotes hydrogen, hydroxyl, methyl, ethyl, propyl, isopropyl, butyl, isobutyl, tert.-butyl, pentyl, isopentyl, neopentyl, hexyl, methoxy, ethoxy, propoxy, butoxy, pentoxy, hexoxy, cyclopropyl, cyclobutyl, cyclopentyl, cyclohexyl, cycloheptyl, phenyl, tolyl, benzyl, benzyloxy, or a substituted derivative thereof, or together with (i) $R^9$ and (ii) the carbon atom, to which $R^8$ is bonded, forms a substituted or unsubstituted 3- to 6-membered carbocycle or heterocycle;

$R^9$ denotes hydrogen, hydroxyl, methyl, ethyl, propyl, isopropyl, butyl, isobutyl, tert.-butyl, pentyl, isopentyl, neopentyl, hexyl, methoxy, ethoxy, propoxy, butoxy, pentoxy, hexoxy, cyclopropyl, cyclobutyl, cyclopentyl, cyclohexyl, cycloheptyl, phenyl, tolyl, benzyl, or a substituted derivative thereof, or together with (i) $R^8$ and (ii) the carbon atom, to which $R^9$ is bonded, forms a substituted or unsubstituted 3- to 6-membered carbocycle or heterocycle;

$R^{10}$ is as defined above;

$R^{101}$ denotes a monovalent radical selected from methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, phenyl, tolyl, benzyl, or a substituted derivative thereof, —$C_6H_2(CH_3)_3$, —$C_6(CH_3)_5$, —$CH_2$—$C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenyl-methyl, 2,4-dichlorophenyl-methyl, 2,6-dichlorophenyl-methyl, 3-aminophenyl, 4-aminophenyl, 4-carboxyphenyl, 2-methoxycarbonylphenyl-methyl, 3-trifluoromethyl-phenyl, 4-trifluoromethyl-phenyl, 3,5-bis(trifluoromethyl)-phenyl, 4-trifluoromethoxyphenyl, benzyl, 2-acetamido-4-methylthiazol-5-yl, phenylethyl, 1-phenyl-propyl, (S)-(+)-camphor-10-yl, (R)-(−)-camphor-10-yl, 2-thiophenyl, 4-methoxy-phenyl, 3,5-dimethoxy-phenyl, 3-methylphenyl, 4-methylphenyl, 4-tert.-butyl-phenyl, 4-propylphenyl, 2,5-dimethyl-phenyl, 2-meth-oxy-5-methylphenyl, 2,3,5,6-tetramethylphenyl, 1-naphthyl, 2-naphthyl, 4-fluorophenyl, 2,4-difluorophenyl, 2-chloro-6-methyl-phenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)-anilino, 4-acetamidophenyl, 2,2,2-trifluoro-ethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methyl-isoxazol-3-yl, 1-adamantyl, 4-chlorophenoxymethyl, 2-chloro-pyridine-5-methyl, 5,7-dimethyl-1,3,4-triaza-indolizin-2-yl, (S)-camphan-1-yl, (R)-camphan-1-yl or 8-quinolinyl, or a bivalent radical formally obtained by abstraction of a hydrogen from the above monovalent $R^{101}$ radicals, via which (bivalent radical) the radical (II) can be bonded to the rest of the conjugate;

$R^{102}$ denotes a monovalent radical selected from methyl, ethyl, propyl, isopropyl, butyl, isobutyl, tert.-butyl, pentyl, isopentyl, neopentyl, hexyl; cyclopropyl, cyclobutyl, cyclopentyl, cyclohexyl, cycloheptyl; phenyl, tolyl, benzyl, or a substituted derivative thereof; —$C_6H_2(CH_3)_3$, —$C_6(CH_3)_5$, —$CH_2C_6H_2$ $(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 3-aminophenyl, 4-aminophenyl, 4-chlorophenyl-methyl, 2,4-dichlorophenyl-methyl, 2,6-dichlorophenyl-methyl, 2-methoxycarbonylphenyl-methyl, 3-trifluoromethylphenyl, 4-trifluoromethylphenyl, 3,5-bis(trifluoromethyl)-phenyl, 4-trifluoromethoxyphenyl, 2-acetamido-4-methylthiazol-5-yl, phenylethyl, 1-phenyl-propyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-tert.-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonyl-phenyl, 2-arylsulphonylphenyl, 3-(N-acetyl-6-methoxy)-aniline, 4-acetamidophenyl, 2,2,2-trifluoro-ethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methyl-isoxazol-3-yl, 1-adamantyl, 4-chlorophenoxymethyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl, or a bivalent radical formally obtained by abstraction of a hydrogen from the above monovalent $R^{102}$ radicals, via which (bivalent radical) the radical (II) can be bonded to the rest of the conjugate;

$R^{103}$ denotes hydrogen or one of the meanings of $R^{101}$, via which radical $R^{103}$, if it is bivalent, the radical (II) can be bonded to the rest of the conjugate;

$R^{11}$ denotes hydrogen, methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methyl-hex-2-yl, amino-$C_{1-4}$alkyl, $C_{1-4}$-alkylamino-$C_{1-4}$-alkyl, $C_{1-4}$-dialkylamino-$C_{1-4}$-alkyl or $C_{1-4}$-alkoxy-$C_{1-4}$-alkyl, phenyl, tolyl, benzyl, or a substituted derivative thereof, or one of the following radicals:

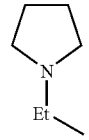
(a1)

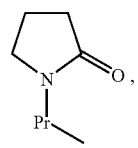
(a2)

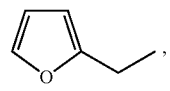
(a3)

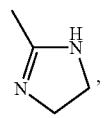
(a4)

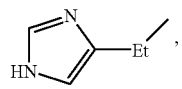
(a5)

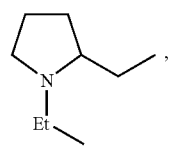
(a6)

-continued

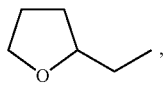
(a7)

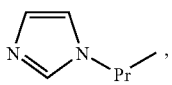
(a8)

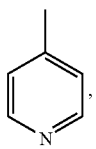
(a9)

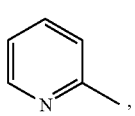
(a10)

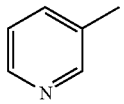
(a11)

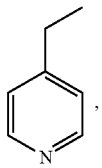
(a12)

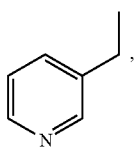
(a13)

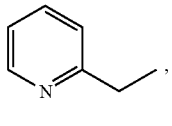
(a14)

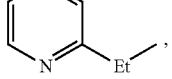
(a15)

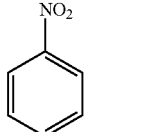
(a16)

(a17)

-continued (a18) 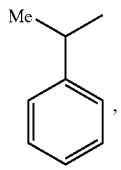

(a19) 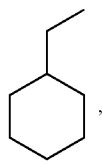

(a20) 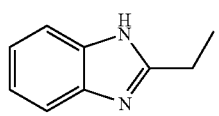

(a21) 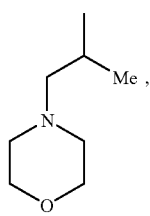

(a22) 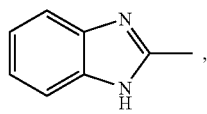

(a23) 

(a24) 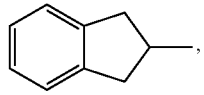

(a25) 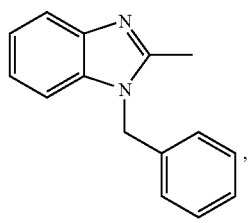

(a26) 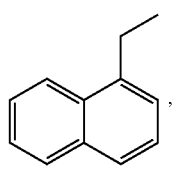

(a27) 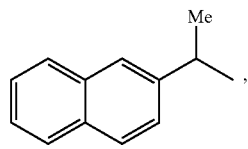

(a28) 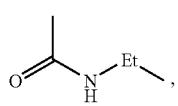

L denotes —NHSO$_2$—, —CH$_2$NHSO$_2$—, —NHSO$_2$CH$_2$—, —SO$_2$—NH—, —CH$_2$SO$_2$NH—, —SO$_2$NHCH$_2$—, —NHCO—, —CH$_2$NH—CO—, —NHCOCH$_2$—, —CONH—, —CH$_2$CONH—, —CONHCH$_2$—, —OCH$_2$—, —CH$_2$OCH$_2$, —OCH$_2$CH$_2$—, —CH$_2$O— or —CH$_2$CH$_2$O—;

$R^{12}$ denotes hydrogen, methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methyl-hex-2-yl, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$- alkyl, phenyl, tolyl, benzyl, or a substituted derivative thereof, or one of the radicals (a1) to (a28) or together with (i) one of $R^{15}$ (if present), $R^{13}$ or $R^{14}$, and (ii) the nitrogen atom, to which $R^{12}$ is bonded, forms a substituted or unsubstituted, saturated or unsaturated 4- to 6-membered heterocyclic residue which can contain further hetero atoms;

X denotes N, O or S;

p denotes zero or 1;

$R^{13}$ denotes hydrogen, methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, nitro, cyano, —COR$^{104}$, —CO—OR$^{105}$ or together with (i) X and (ii) one of $R^{12}$, $R^{14}$ or $R^{15}$ forms a substituted or unsubstituted 4- to 6-membered heterocycle which can contain further hetero atoms;

$R^{104}$ denotes hydrogen, methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, phenyl, tolyl, benzyl, or a substituted derivative thereof;

$R^{105}$ denotes hydrogen or one of the meanings of $R^{104}$,

Y denotes N or S;

$R^{14}$ denotes hydrogen, methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methyl-hex-2-yl, phenyl, tolyl, benzyl, or a substituted derivative thereof, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$-alkyl, one of the radicals (a1) to (a28), or together with (i) Y and (ii) one of $R^{15}$ (if present), $R^2$, or $R^{13}$ forms a saturated or unsaturated, substituted or unsubstituted 4- to 6-membered heterocyclic residue which can contain further hetero atoms; and $R^{15}$ denotes hydrogen, methyl, ethyl, propyl, isopropyl, butyl, isobutyl, tert.-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methylhex-2-yl, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$- alkyl, phenyl, tolyl, benzyl, or a substituted derivative thereof, one of the radicals (a1) to (a28) or together with (i) Y and (ii) one of $R^{14}$ (if p=z=1), $R^{12}$, or $R^{13}$ forms a saturated or unsaturated, substituted or unsubstituted 4- to 6-membered heterocyclic residue which can contain further hetero atoms, or represents a single bond in case the radical (II) is bonded to the rest of the conjugate via Y, and the other radicals are as defined above, and their stereoisomers, their hydrates, their physiologically acceptable salts and the hydrates of these salts.

Preferred conjugates (I) in this further preferred embodiment are those in which $R^7$ represents a hydroxy group or a direct bond, so that the radical (II) is bonded to the rest of the conjugate directly via the carbon atom marked with a cross.

Particularly preferred conjugates (I) in this further preferred embodiment are those in which the radical (II) is linked to the rest of the conjugate via the nitrogen atom, to which $R^{10}/R^{11}$ are attached. From these conjugates especially preferred are those wherein CT represents the camptothecin radical which is linked to the rest of the conjugate via the oxygen atom at the $C_{20}$-carbon atom;

LI denotes a group of the formula -AA1-AA2-AA3- (III) wherein

AA1 denotes a divalent residue of valine, leucine, or isoleucine;

AA2 denotes a divalent proline residue, and

AA3 denotes a divalent residue of alanine, norvaline, histidine, glycine, asparagine, or aspartate, Sp denotes a carbonyl or thiocarbonyl group, IA denotes a non-peptide radical of the formula (II) addressing an $\alpha_v\beta_3$ integrin receptor, wherein $R^7$ denotes hydroxyl;

$R^8$, $R^9$, $R^{12}$, and $R^{14}$ denote hydrogen;

g, h, i, and k denote zero, $R^{10}$ denotes a —CONHR$^{101}$ group;

$R^{101}$ denotes -Ph-NH—, so that the radical (II) is linked to the rest of the conjugate via the nitrogen atom in $R^{101}$;

L denotes —NH—SO$_2$— being linked to the adjacent phenylene units A and B such that each of these phenylene units is 1,3-substituted;

X denotes oxygen;

y is zero;

p is 1, $R^{15}$ is propyl, and the other symbols are as defined above, and their stereoisomers, their hydrates, their physiologically acceptable salts and the hydrates of these salts.

The present invention also includes both the individual enantiomers and diastereomers and the corresponding racemates, diastereomer mixtures of the conjugates (I). In addition, all possible tautomeric forms of the conjugates described above are included according to the present invention. Furthermore, the present invention includes both the pure E- and Z-isomers of the conjugates (I) and their E/Z-mixtures in all ratios. The diastereomer mixtures or E/Z-mixtures can be separated into the individual isomers by chromatographic processes. The racemates can be resolved into the respective enantiomers either by chromatographic processes on chiral phases or by resolution.

Physiologically acceptable salts of the conjugates (I) according to the invention are understood according to the invention as meaning non-toxic salts which in general are accessible by reacting the conjugates (I) with an inorganic or organic base or acid conventionally used for this purpose. Examples of preferred salts of the compounds (I) are the corresponding alkali metal salts, e.g. lithium, potassium and sodium salts, the corresponding alkaline earth metal salts such as the magnesium or calcium salts, the quaternary ammonium salts such as, for example, the triethyl ammonium salt, acetate, benzene sulphonate, benzoate, dicarbonate, disulphate, ditartrate, borate, bromide, carbonate, chloride, citrate, dihydrochloride, fumarate, gluconate, glutamate, hexyl resorcinate, hydrobromide, hydrochloride, hydroxynaphthoate, iodide, isothionate, lactate, laurate, linoleate, malate, maleate, mandelate, mesylate, methyl bromide, methyl nitrate, methyl sulphate, nitrate, oleate, oxalate, palmitate, pantothenate, phosphate, diphosphate, polygalacturonate, salicylate, stearate, sulphate, succinate, tartrate, tosylate and valerate and other salts used for medicinal purposes.

In the context of the present invention, the substituents, if not stated otherwise, in general have the following meanings:

Alkyl per se as well as the prefixes "alkyl" and "alk" in the terms such as "alkylcarbonyl", "alkylsulphonyl", "alkylaminocarbonylamino", "alkoxy", "alkoxyalkyl" and "alkoxycarbonyl" as well as the suffixes in "haloalkyl", "haloalkoxy" and "aryloxyalkyl" represent linear or branched alkyl preferably having from 1 to 20, more preferably from 1 to 14 and most preferably from 1 to 6 carbon atoms. Non-limiting examples include methyl, ethyl, propyl, isopropyl, butyl, isobutyl, tert.-butyl, pentyl, isopentyl, neopentyl, hexyl, isohexyl, heptyl, isoheptyl, octyl, iso-octyl, nonyl, decyl, dodeyl and eicosyl. Non-limiting examples of alkoxy include methoxy, ethoxy, propoxy, isopropoxy, butoxy, isobutoxy, pentoxy, isopentoxy, hexoxy, isohexoxy, heptoxy, isoheptoxy, octoxy and isooctoxy.

Non-limiting examples of alkoxyalkyl include ethoxyethyl, ethoxypropyl, etc. Non-limiting examples of alkoxycarbonyl include methoxycarbonyl, ethoxycarbonyl, propoxycarbonyl, isopropoxycarbonyl, butoxycarbonyl and isobutoxycarbonyl. A non-limiting example of haloalkyl is 2,2,2-trifluoro-ethyl. A non-limiting example of haloalkoxy is trifluoromethoxy. Non-limiting examples of aryloxyalkyl include phenoxy-methyl and 4-chlorophenoxy-methyl.

Alkenyl represents linear or branched alkenyl preferably having from 2 to 20, more preferably from 2 to 12 and most preferably from 2 to 6 carbon atoms and at least one, preferably from 1 to 2, C—C double bonds. Non-limiting examples include allyl, propenyl, isopropenyl, butenyl, isobutenyl, 2,2-dimethyl-ethenyl, pentenyl, isopentenyl, hexenyl, isohexenyl, heptenyl, isoheptenyl, octenyl, and iso-octenyl.

Alkynyl represents linear or branched alkynyl preferably having from 2 to 20, more preferably from 2 to 12 and most preferably from 2 to 6 carbon atoms and at least one, preferably from 1 to 2, C—C triple bonds. Non-limiting examples include ethynyl, 2-butynyl, 2-pentynyl and 2-hexynyl.

Acyl represents linear or branched acyl preferably having from 1 to 9 carbon atoms. Non-limiting examples include acetyl, ethylcarbonyl, propylcarbonyl, isopropylcarbonyl, butylcarbonyl and isobutylcarbonyl.

Cycloalkyl per se as well as the prefix "cycloalk" in the terms "cycloalkoxy" and "cycloalkyl-alkyl" represent a cycloalkyl preferably having from 3 to 10, more preferably from 3 to 7 carbon atoms. Non-limiting examples include cyclopropyl, cyclobutyl, cyclopentyl, cyclohexyl, cycloheptyl, adamantyl, (R)- and (S)-camphanyl and keto derivatives thereof such as camphoryl, (R)-(−)- and (S)-(+)-camphoryl; cyclopropyl, cyclopentyl and cyclohexyl are preferred. Non-limiting examples of cycloalkoxy include cyclopropoxy and cyclohexoxy. A non-limiting example of cycloalkyl-alkyl is cyclopropyl-methyl.

Aryl per se as well as the prefix "ar(yl)" in the terms "aryloxy", "aralkyl" and "aralkoxy" represents an aromatic radical preferably having from 6 to 10 carbon atoms or a derivative thereof substituted preferably with alkyl, halogenalkyl, alkoxy, halogenalkoxy, halogen, amino, acylamino, alkylsulphonyl and/or arylsulphonyl such as 3- and 4-methylphenyl, 4-propylphenyl, 4-tert.-butylphenyl, 2,5-dimethylphenyl, 2,3,5,6-tetramethylphenyl, 4-methoxyphenyl, 2,5-, 3,4- and 3,5-dimethoxyphenyl, 2-methoxy-5-methylphenyl, 4-fluorophenyl, 2-, 3- and 4-chlorophenyl, 2,4-difluorophenyl, 2,3-, 2,4-, 3,4-, 2,5-, 3,5- and 2,6-dichlorophenyl, 2-chloro-4-fluoro-phenyl, 2-chloro-6-methylphenyl, 3-chloro-6-methoxy-phenyl, 2-, 3- and 4-trifluoromethyl-phenyl, 4-trifluoromethoxy-phenyl, 3,5-bis(trifluoromethyl)-phenyl, 3- and 4-aminophenyl, 1-acetylamino-2-methoxy-phen-5-yl, 2-alkyl- and 2-arylsulphonylphenyl, 4-acetamino-phenyl. Phenyl, tolyl, xylyl and pentamethylphenyl are preferred.

Aralkyl preferably represents a $C_{6-10}$-aryl-$C_{1-4}$-alkyl, more preferably a $C_{5-6}$-aryl-$C_{1-2}$-alkyl, such as benzyl, 2-phenethyl, or 1-phenylpropyl, or a derivative thereof substituted preferably with alkyl, halogen or alkoxycarbonyl such as dimethylbenzyl, 4-chlorobenzyl, 2,4- and 2,6-dichlorophenyl-methyl, 2-methoxycarbonylphenyl-methyl,.

Hetaralkyl preferably represents a $C_{3-10}$-hetaryl-$C_{1-4}$-alkyl, more preferably a $C_{5-6}$-hetaryl-$C_{1-2}$-alkyl which can contain up to 3 hetero atoms selected from the group consisting of S, N and O, such as 2-chloropyridin-5-methyl.

Aralkoxy preferably represents a $C_{6-10}$-aryl-$C_{1-4}$-alkoxy, more preferably a $C_6$-aryl-$C_{1-2}$-alkoxy, such as benzyloxy.

Aralkenyl preferably represents a $C_{6-10}$-aryl-$C_{2-4}$-alkenyl, more preferably a $C_6$-aryl-$C_{2-4}$-alkenyl such as 2-phenylethenyl.

Halogen represents fluorine, chlorine, bromine and iodine.

Heterocyclyl represents saturated, partially unsaturated or aromatic 3- to 10-membered, for example 5- or 6-membered, heterocyclyl which can contain up to 3 hetero atoms selected from the group consisting of S, N and O and which, in the case of a nitrogen atom, can also be bonded via this. Non-limiting examples include oxadiazolyl, thiadiazolyl, pyrazolyl, pyridyl, pyrimidinyl, pyridazinyl, pyrazinyl, thienyl, furyl, pyrrolyl, pyrrolidinyl, piperazinyl, tetrahydropyranyl, tetrahydrofuranyl, 1,2,3-triazolyl, thiazolyl, oxazolyl, isoxazolyl, imidazolyl, morpholinyl, piperidyl, and quinolinyl and derivatives thereof. Thiazolyl, furyl, oxazolyl, pyrazolyl, triazolyl, pyridyl, pyrimidinyl, pyridazinyl and tetrahydropyranyl are preferred.

Non-limiting examples of heterocyclyl derivatives include heterocyclyl substituted preferably with halogen, alkyl, alkoxycarbonyl, and/or acylamino such as 2-chloropyridin-3-yl, N-methoxycarbonylpiperidin-3-yl, 5-methyl-isoxazol-3-yl, 2-acetamino-4-methyl-thiazol-5-yl, 5-chloro-3-methyl-benzothiazol-2-yl, 5,7-dimethyl-1,3,4-triaza-indolizin-2-yl. The terms "heteroaryl" and "hetaryl" represent aromatic heterocyclic radicals.

The terms "carbocycle or heterocycle" and "carbocyclic or heterocyclic" used in this specification as, for example, in the definition of the substituents $R^5$ and $R^9$, preferably refer to a 3- to 6-membered ring such as, for example, a cyclopropane ring, cyclobutane ring, cyclopentane ring, cyclohexane ring, dihydrofuran ring, tetrahydrofuran ring, dihydropyran ring, tetrahydropyran ring, dioxane ring, dihydrothiophene ring, tetrahydrothiophene ring or a substituted derivative thereof.

The conjugates according to the invention are characterized in that a cytotoxic radical or a radical of a cytostatic or of a cytostatic derivative is bonded via a linking unit to a non-peptide radical IA addressing $\alpha_v\beta_3$ integrin receptors. The non-peptide moiety of the conjugate addressing $\alpha_v\beta_3$ integrin receptors serves to bring the toxophoric part of the conjugate into tumour cells or into the vicinity of tumour cells and thus to achieve tissue selectivity. Growing tumour tissue stimulates the formation of new blood vessels, i.e. angiogenesis, to a considerable extent in order to cover its increasing nutritional need. The blood vessels newly formed by angiogenesis differ from conventional tissue by specific markers on the surfaces of the endothelial cells formed. Moreover, the $\alpha_v\beta_3$ integrin receptor is expressed by many human tumours (cf. WO 98/10795 and the references cited therein). Thus, the conjugate is brought selectively into the tumour tissue or into the vicinity of the tumour tissue to be treated by the interaction of its non-peptide part addressing $\alpha_v\beta_3$ integrin receptors with $\alpha_v\beta_3$ integrin receptors found on endothelial cells or on tumour cells formed by angiogenesis.

Unlike peptide radicals addressing $\alpha_v\beta_3$ integrin receptors (such as disclosed, for example, in WO 98/10795), the non-peptide moieties according to the invention addressing $\alpha_v\beta_3$ integrin receptors are distinguished by an increased serum stability, whereby the transport of the toxophore in the conjugate to the tumour tissue is ensured to an increased extent.

In a preferred embodiment, the above-mentioned conjugates (I) having antagonistic action against $\alpha_v\beta_3$ integrin receptors retain their property of addressing $\alpha_v\beta_3$ integrin receptors in the conjugate. This means that the radicals IA is linked to the toxophore radical CT in such a way that no or only a slight impairment of the above-mentioned action of the compounds results thereby. In the normal case, the linkage with the linking unit -LI-$Sp_x$- will take place via a suitable functional group in the moiety comprising an IA radical, for example via an amino, hydroxyl or carboxyl function. (The term "moiety comprising" in the context of this invention means a compound formally obtained by adding a group such as, for example, hydrogen or hydroxyl, for completing the molecule). If the above-mentioned moieties have no functional group, such functional group can easily be introduced into the molecule by conventional processes known to the person skilled in the art without the loss of the antagonistic action against $\alpha_v\beta_3$ integrin receptors.

The conjugate according to the invention can release its toxophoric radical at its target site and this can enable penetration into the tumour tissue. This is carried out by the specific choice of a unit linking the toxophoric radical CT to the radical IA addressing $\alpha_v\beta_3$ integrin receptors. The linking unit of the conjugates of the present invention is designed such that it can be cleaved by the tumour-associated enzyme elastase or an elastase-like activity. It is surprising that the enzyme recognizes and cleaves a substrate seuqence as in the compounds of the present invention which is bonded to rather bulky moieties both at the amino and the carboxy terminus and that it directly releases the toxophore.

A further suitable starting point for promoting the tissue selectivity of the action of the conjugates according to the invention consists in the so-called ADEPT approach, wherein conjugates are cleaved by certain enzymes. These enzymes are introduced into the body coupled to antibodies together with the conjugates according to the invention, the antibodies serving as vehicles specifically addressing tumour tissue. This leads to a selective concentration both of the conjugate and of the enzyme/antibody system in the tumour tissue, whereby the toxophore is released in the tumour tissue with even greater selectivity and can display its action there.

The novel conjugates according to the invention can be prepared by linkage of the toxophore radical CT to the linking unit -LI-$Sp_x$- and subsequent linkage to the radical IA addressing $\alpha_v\beta_3$ integrin receptors. However, it is also possible to first connect the radical IA addressing $\alpha_v\beta_3$ integrin receptors to the linking unit -LI-$Sp_x$- and then to bind the toxophore radical CT to the linking unit.

The combination of the individual units of the conjugates (I) can preferably be carried out by means of functional groups which can be reacted with one another and, as a result, can be linked by conventional processes known in the art. For example carboxyl functions can be reacted with amino functions with formation of an amide group. It is also possible to synthesize the linking unit -LI-$Sp_x$- stepwise on one of the two moieties to be connected, i.e. on the toxophore moiety comprising radical CT or the moiety comprising radical IA addressing $\alpha_v\beta_3$ integrin receptors, by conventional processes known in the art and then to link the finished linking unit to the radical which is still to be bound.

Thus, the present invention relates to a process for the preparation of the conjugates (I) comprising

[A] (for conjugates (I) wherein x=zero) the reaction of a moiety comprising radical (II) which has a free or an activated carboxyl function, with a moiety comprising the unit CT-LI- which has a free primary or secondary amino group, or

[B] the reaction of a moiety comprising radical (II) which has a free primary or secondary amino function,
with a carbonic acid derivative such as, for example, phosgene, thiophosgene or a chloroformic acid ester, followed by the reaction with a moiety comprising the unit CT-LI- which has a free primary or secondary amino group, or

[C] the reaction of a moiety comprising radical (II) which contains a free primary or secondary amino function, with a moiety comprising the unit CT-LI- which contains a free or activated carboxyl function, wherein all radicals throughout [A] to [C] have the meanings of formula (I).

If appropriate, protective groups can be introduced and removed; derivatization of nitrogen atoms can be derivatisized; compounds obtained can be converted into the free acid and/or into one of the physiologically acceptable salts by reaction with an inorganic or organic base or acid; all these steps being possible at the appropriate points in time in the preparation process.

According to a preferred embodiment, several steps of the preparation process are carried out on a solid phase.

In variant [A] of the preparation process, a moiety comprising radical IA addressing $\alpha_v\beta_3$ integrin receptors from the group of radicals (II) is linked via its free carboxyl function to the amino function of a moiety comprising the unit CT-LI- with formation of an amide group. This reaction can be carried out by conventional methods known to the person skilled in the art (cf., for example, J. March, Advanced Organic Chemistry, $3^{rd}$ ed., p. 370 et seq., Wiley 1985). It is preferred according to the invention to activate the carboxyl function of the moiety comprising radical IA addressing $\alpha_v\beta_3$ integrin receptors and then to react with the moiety comprising the unit CT-LI-, preferably in an organic solvent and preferably in the presence of a base.

For the activation of the carboxyl group, the coupling reagents known in peptide chemistry can be used, such as are described, for example, by Jakubke/Jeschkeit in Aminosäuren, Peptide, Proteine [Amino Acids, Peptides, Proteins], Verlag Chemie 1982, or Tetrahedron Lett. 34, 6705 (1993). Examples mentioned are N-carboxylic acid anhydrides, acid chlorides or mixed anhydrides, adducts with carbodiimides, e.g. N,N'-diethyl-, N,N'-diisopropyl- or N,N'-dicyclohexyl-carbodiimide, N-(3-dimethylaminopropyl)-N'-ethyl-carbodiimide hydrochloride, N-cyclohexyl-N'-(2-morpholinoethyl)-carbodiimide p-toluenesulphonate, or carbonyl compounds such as carbonyl diimidazole, or 1,2-oxazolium compounds such as 2-ethyl-5-phenyl-1,2-oxazolium-3-sulphate or 2-tert.-butyl-5-methyl-isoxazolium perchlorate, or acylamino compounds such as 2-ethoxy-1-ethoxycarbonyl-1,2-dihydroquinoline or propanephosphonic anhydride or isobutyl chloroformate or benzotriazolyloxy-tris(dimethylamino)-phosphonium hexafluorophosphate, 1-hydroxybenzotriazole or N-hydroxysuccinimide esters. It is furthermore possible to employ the acid components in the form of a Leuchs' anhydride.

Bases which can be employed in variants [A] to [C] of the preparation process include, for example, triethyl amine, diisopropyl ethyl amine, pyridine, N,N-dimethylaminopyridine or other bases conventionally used in steps of this types; diisopropyl ethyl amine is particularly preferred.

Variants [A] to [C] of the above preparation process can be carried out within a wide range of pressure and temperature conditions, for example from 0.5 to 2 bar and preferably under normal pressure, or from −30 to +100° C. and preferably from −10 to +80° C., in suitable solvents such as dimethyl formamide, tetrahydrofuran, dichloromethane, chloroform, $C_{1-4}$-alcohols, acetonitrile, dioxane, water or mixtures thereof. As a rule, reaction in DMF, dichloromethane, THF, dioxane/water or THF/dichloromethane at room temperature or with ice-cooling and under normal pressure is preferred.

In variant [B] of the above preparation process, a moiety comprising radical (II) is reacted via its free amino function first with a carbonic acid derivative with formation of the corresponding isocyanate, isothiocyanate or carbamate, which is then linked to the amino function of a toxophore-linking unit conjugate (Ia) with formation of the conjugate (I).

The reaction of the moiety comprising radical (II) via their free amino function with a carbonic acid derivative can be carried out by conventional methods known in the art (cf., for example, J. March, Advanced Organic Chemistry, $3^{rd}$ ed., p. 370 et seq., Wiley 1985). The reaction is preferably carried out with phosgene or a substitute thereof such as, for example, trichloromethyl chloroformate, thiophosgene or a chloroformic acid ester such as chloroformic acid-p-nitrophenyl ester, in a solvent such as dimethyl formamide or a dioxane/water (1:1) mixture or a tetrahydrofuran/dichloromethane (1:1) mixture with cooling or, preferably, at room temperature, and stirring for approximately 10 minutes up to approximately 3 hours, if appropriate in the presence of a base.

The subsequent reaction of the isocyanate, isothiocyanate or carbamate thus obtained with the amino function of a toxophore-linking unit conjugate (Ia) with formation of a corresponding thiourea or urea group can be carried out by conventional methods known to the person skilled in the art (cf., for example, J. March, Advanced Organic Chemistry, 3$^{rd}$ ed., p. 802 et seq., Wiley 1985).

According to the invention, the carbamate or isocyanate or isothiocyanate is preferably reacted with the amino function of the compound (Ia) at room temperature with stirring for approximately 1 to 5 hours, preferably approximately 2 to 3 hours, in the presence of a base in a solvent such as dimethyl formamide.

In variant [C] of the above preparation process, a moiety comprising radical (II) is linked via its free amino function to the carboxyl function of a unit CT-LI with formation of an amide group. This reaction can be carried out by conventional methods (cf., for example, J. March, Advanced Organic Chemistry, 3$^{rd}$ ed., p. 370 et seq., Wiley 1985). It is preferred to activate the carboxyl function of the compound (Ia) and then to react it with a moiety comprising radical (II), preferably in an organic solvent and preferably in the presence of a base.

For activation of the carboxyl group, the coupling reagents known in peptide chemistry can be used, such as described, for example, by Jakubke/Jeschkeit in Aminosäuren, Peptide, Proteine [Amino Acids, Peptides, Proteins], Verlag Chemie 1982 or in Tetrahedron Lett. 34, 6705 (1993). Examples include N-carboxylic anhydrides, acid chlorides or mixed anhydrides, adducts with carbodiimides, e.g. N,N'-diethyl-, N,N'-diisopropyl- or N,N'-dicyclohexyl-carbodiimide, N-(3-dimethylaminopropyl)-N'-ethyl-carbodiimide hydrochloride, N-cyclohexyl-N'-(2-morpholinoethyl)-carbodiimide p-toluenesulphonate, or carbonyl compounds such as carbonyl diimidazole, or 1,2-oxazolium compounds such as 2-ethyl-5-phenyl-1,2-oxazolium-3-sulphate or 2-tert.-butyl-5-methyl-isoxazolium perchlorate, or acylamino compounds such as 2-ethoxy-1-ethoxycarbonyl-1,2-dihydroquinoline, or propanephosphonic anhydride, or isobutyl chloroformate, or benzotriazolyloxy-tris(dimethylamino)-phosphonium hexafluorophosphate, 1-hydroxybenzotriazole or N-hydroxysuccinimide esters. It is furthermore possible to employ the acid components in the form of a Leuchs' anhydride.

The compounds obtained by the process explained above can furthermore be derivatized by removal of protective groups which may be present, further substitution of nitrogen atoms present at preferred positions in the preparation process and/or conversion of the compound obtained into the free acid and/or its physiologically acceptable salts. By way of example, the tert.-butoxymethoxycarbonyl groups conventionally used as protective groups for nitrogen atoms are removed in acidic medium, for example by addition of trifluoroacetic acid. Preferable alkylating agents for the derivatization of nitrogen atoms in this step are reagents conventionally used for this purpose, using which, for example, substituted or unsubstituted alkyl, substituted or unsubstituted cycloalkyl, substituted or unsubstituted aryl or saturated or unsaturated, substituted or unsubstituted heterocyclyl can be bonded to the appropriate nitrogen atom. The above reactions and their implementation are well known in the art and are described in detail in standard works such as, for example, in "Methoden der Organischen Chemie" [Methods of Organic Chemistry] (Houben-Weyl), Vols. 15.1 and 15.2, Georg Thieme Verlag, Stuttgart; 1974.

The moiety comprising the unit CT-LI- which can serve as starting substances may be prepared by conventional methods. The linkage of the radical CT to amino acid units can be carried out by conventional methods of peptide chemistry (cf., for example, Jakubke/Jeschkeit in Aminosäuren, Peptide, Proteine [Amino Acids, Peptides, Proteins], Verlag Chemie 1982, or in "Methoden der Organischen Chemie" [Methods of Organic Chemistry] (Houben-Weyl), 4$^{th}$ ed.; Vols. 15.1 and 15.2, Georg Thieme Verlag, Stuttgart, 1974 and is also described, for example, in WO 96/31532 and 98/51703, the contents of which are incorporated herein by reference.

The bonding of the appropriate carbonyl or thiocarbonyl groups can be carried out as described above by reaction of the moiety comprising the unit CT or of the CT-amino acid conjugate with phosgene or a substitute thereof such as, for example, trichloromethyl chloroformate or thiophosgene.

Although it is preferred to first synthesize the moiety comprising the unit CT-LI-, it is also possible, of course, to build up the moiety comprising the unit -LI-Sp$_x$- in series first on the moiety comprising radical IA addressing $\alpha_v\beta_3$ integrin receptors or to bond it as a whole and then to connect the conjugate thus obtained to the radical CT.

According to a preferred embodiment, the synthesis of the compounds according to the invention is partly carried out on a solid phase such as a polystyrene resin, particularly preferably a commercially available Wang polystyrene resin. The resin is in this case first swollen in a solvent such as dimethyl formamide. The moiety (II) addressing $\alpha_v\beta_3$ integrin receptors is then bonded to the resin via its carboxyl function by standard processes. For example, the bonding of the carboxylic acid to the resin can be carried out in the presence of a base such as pyridine and a reagent activating the carboxyl unit, such as an acid halide, for example dichlorobenzoyl chloride, in a solvent such as dimethyl formamide. However, other reagents conventionally used for this purpose can also be employed. The reaction mixture is agitated at room temperature and normal pressure for at least 2 hours, preferably 12 hours, particularly preferably approximately 24 hours, the carboxylic acid being employed in an excess with respect to the loading of the solid phase, preferably in a two- to three-fold excess. All reactions described herein can then be carried out on the moiety (II) bound to the resin and addressing $\alpha_v\beta_3$ integrin receptors, as described below.

After linkage of the first amino acid to the moiety comprising radical CT, diastereomer mixtures can come into existence. Pure diastereomers can be prepared by the processes indicated above, for example, by separating the diastereomers in a suitable manner after coupling of the first amino acid unit to the camptothecin and optionally subsequent protective group removal.

The moiety comprising radical (II) can be prepared from commercially available starting compounds as described hereinafter. The essential steps of the preparation process are the reaction of a β-amino acid of the formula

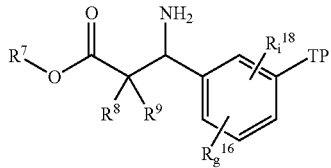

(IIa)

wherein

TP denotes —(CH$_2$)$_m$NO$_2$, —(CH$_2$)$_m$O—C$_{1-6}$-alkyl, —(CH$_2$)$_m$SO$_2$G, —(CH$_2$)$_m$COG or —(CH$_2$)$_m$CH$_2$O—C$_{1-6}$-alkyl, wherein m is in each case zero or 1;

G denotes hydroxyl or C$_{1-6}$-alkoxy, and the other radicals are as defined above, where R$^7$ can additionally be a solid phase conventionally used for carrying out a solid-phase reaction, with a compound R$^{10}$-A, wherein R$^{10}$ denotes —SO$_2$R$^{101}$, —COR$^{101}$ or —COOR$^{102}$, A denotes —Cl, —Br, —I, trifluoromethoxy, —O-tosyl, C$_{1-6}$-alkoxy, —O—CO—C$_{1-6}$-alkyl, —O—CO—C$_{1-6}$-alkoxy or —OC(CH$_3$)=CH$_2$, and the other radicals are as defined above, to give a compound of the formula

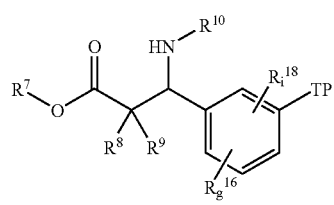

(IIb)

the conversion of the radical TP into the radical Q, where

Q denotes —(CH$_2$)$_m$NH$_2$, —(CH$_2$)$_m$OH, —(CH$_2$)$_m$CH$_2$OH, —(CH$_2$)$_m$SO$_2$A or —(CH$_2$)$_m$COA, A is as defined above; and m is zero or 1;

the reaction of resultant compound with a compound of the formula

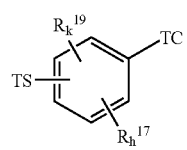

(IIc)

wherein

TS denotes ASO$_2$(CH$_2$)$_n$—, NH$_2$(CH$_2$)$_n$—, ACO(CH$_2$)$_n$—, HOCH$_2$(CH$_2$)$_n$—, M(CH$_2$)$_n$—, MCH$_2$(CH$_2$)$_n$—, HSCH$_2$(CH$_2$)$_n$— or HS(CH$_2$)$_n$—, wherein n denotes zero or 1;

M is selected from Mg, Li, Cd and Sn;

TC denotes —NO$_2$ or

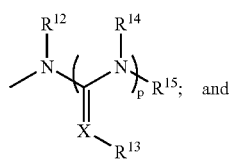

A, X and R$^{12}$ to R$^{15}$ are as defined above;

to give a compound of the formula

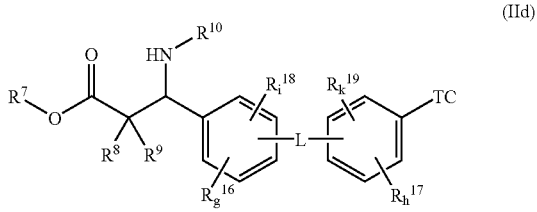

(IId)

wherein the radicals are as defined above;

if appropriate, the conversion of TC, if TC is a nitro group, into an acyclic or cyclic urea, thiourea or guanidine unit with retention of the radical (II).

The β-amino acid derivatives (IIa) are either commercially available or are accessible in a simple manner by standard chemical processes, such as are known in the art and are described in standard works such as "Methoden der Organischen Chemie" (Methods of Organic Chemistry) (Houben-Weyl), Georg Thieme Verlag, Stuttgart. In particular, reference is made to the preparation processes for β-amino acid derivatives described by Rodionow et al., J. Am. Chem. Soc 51, 844–846 (1929), Kunz et al., Angew. Chem 101, 1042–1043 (1989) and Ishihara et al., Bull. Chem. Soc. Jpn. 68 (6), 1721–1730 (1995).

According to a preferred embodiment, the β-amino acid derivatives (IIa) are obtained by reaction of malonic acid or a malonic ester with a benzaldehyde derivative of the formula

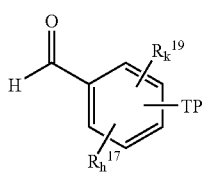

(IIe)

wherein R$^{17}$, R$^{19}$, h, k and TP are as defined above, preferably in the presence of ammonia, ammonium compounds or amines. In case of reacting a malonic ester, a base conventionally employed for this purpose, such as sodium hydride or sodium alkoxide, preferably sodium methoxide or sodium ethoxide, can be added. Preferably, an ammonium compound such as, for example, ammonium acetate is employed.

The benzaldehyde derivatives (IIe) are either commercially available or are accessible in a simple manner by standard chemical processes, such as are known in the art and are described in standard works such as "Methoden der Organischen Chemie" (Methods of Organic Chemistry) (Houben-Weyl), Georg Thieme Verlag, Stuttgart.

According to a preferred embodiment, a nitrobenzaldehyde derivative such as 3- or 4-nitro-benzaldehyde or an alkoxybenzaldehyde derivative such as 3- or 4-methoxybenzaldehyde is employed as the compound (IIe).

According to a preferred embodiment, the β-amino acid (IIa) is obtained by reaction of approximately equimolar amounts of malonic acid, ammonium acetate and 3-nitrobenzaldehyde or 3-methoxy-benzaldehyde in a solvent such as isopropanol with heating for a couple of hours, preferably 2 to 6 hours, at 50 to 110° C., preferably with reflux of the solvent, under normal conditions (i.e. under normal pressure and under an atmosphere of normal air).

For the following reaction steps, the carboxyl group is blocked by a conventional protective group PG. Protective groups of this type are known to the person skilled in the art (cf., for example, Jakubke/Jeschkeit in Aminosäuren, Peptide, Proteine [Amino Acids, Peptides, Proteins], Verlag Chemie 1982, or in "Methoden der Organischen Chemie" [Methods of Organic Chemistry] (Houben-Weyl), 4$^{th}$ ed.; Vols. 15.1 and 15.2, Georg Thieme Verlag, Stuttgart, 1974. The carboxyl group is particularly preferably esterified, where PG is a $C_{1-6}$-alkyl such as, for example, methyl, ethyl, propyl, isopropyl, butyl, isobutyl, tert.-butyl, pentyl, isopentyl, neopentyl, hexyl, a $C_{3-7}$-cycloalkyl such as, for example, cyclopropyl, cyclobutyl, cyclopentyl, cyclohexyl, a $C_{3-7}$-cycloalkyl-$C_{1-6}$-alkyl such as, for example, cyclopropylmethyl, an aryl such as, for example, phenyl, tolyl, a $C_{6-10}$-ar-$C_{1-4}$-alkyl such as, for example, benzyl, or a substituted derivative thereof. The ester groups can be converted into the corresponding free carboxylic acids in a conventional manner, such as, for example, by basic ester hydrolysis.

According to a preferred embodiment, the carboxyl group of the above β-amino acid is esterified by reaction with an alcohol such as ethanol or a polymer conventionally used for carrying out a solid-phase reaction. This can be carried out under conditions known to the person skilled in the art, such as acid catalysis and, if appropriate, addition of a dehydrating agent such as dicyclohexyl carbodiimide. Preferably, however, the β-amino acid is suspended in the appropriate alcohol present in an excess, such as ethanol, hydrogen chloride is passed through for a period of approximately 30 minutes to approximately 2 hours and the mixture is then heated under normal conditions for a couple of hours, preferably approximately 1 to 6 hours and particularly preferably approximately 3 to 5 hours, at approximately 50 to approximately 100° C., preferably under reflux of the alcohol.

According to a preferred embodiment, the synthesis of the moiety comprising radical (II) is carried out on a solid phase such as a polystyrene resin, particularly preferably a commercially available Wang polystyrene resin. In this connection, the resin is first swollen in a solvent such as dimethyl formamide. The appropriate carboxylic acid serving as a starting compound is then bonded to the resin by standard processes. For example, the bonding of the carboxylic acid to the resin can be carried out in the presence of a base such as pyridine and a reagent activating the carboxyl unit, such as an acid halide, for example dichlorobenzoyl chloride, in a solvent such as dimethyl formamide. However, other reagents conventionally used for this purpose can also be employed. The reaction mixture is stirred at room temperature and normal pressure for at least 2 hours, preferably at least 12 hours, particularly preferably approximately 24 hours, the carboxylic acid being employed in an excess, preferably in a two- to three-fold excess (based on equivalents), with respect to the loading of the solid phase.

After removal of reagents which may be unreacted, if desired a derivatization of the carboxylic acid bonded to the resin can be carried out without this previously needing to be removed from the resin. Removal from the resin is carried out in a conventional manner, preferably in an acidic medium. The product removed from the resin can be purified by known purification processes such as, for example, chromatographic processes after removal of solvents which may be present.

The carboxyl-protected β-amino acids accessible in this way can be reacted with a suitable sulphonating, carbamoylating or acylating reagent in order to obtain the corresponding sulphonamide, carbamate or amide derivatives. Preferred sulphonating and carbamoylating reagents used are sulphonyl chlorides of the formula $R^{101pr}$—$SO_2Cl$ and carbamoyl chlorides of the formula $R^{102pr}$—$COOCl$, wherein $R^{101pr}$ and $R^{102pr}$ are identical with $R^{101}$ and $R^{102}$ or are precursors which can be transformed into the radicals $R^{101}$ and $R^{102}$.

Instead of the above-mentioned sulphonyl or carbamoyl chlorides, it is also possible to employ the corresponding fluorides, bromides or iodides. As acylating reagent, the appropriate carboxylic acid halides or carboxylic acid anhydrides are reacted with the amino group, the appropriate $C_{1-6}$-alkyl carboxylic acid chlorides such as methyl, ethyl, propyl, isopropyl, butyl, isobutyl, tert.-butyl, pentyl, isopentyl, neopentyl and hexyl carboxylic acid chlorides, $C_{3-7}$-cycloalkyl carboxylic acid chlorides such as cyclopropyl, cyclobutyl, cyclopentyl and cyclohexyl carboxylic acid chlorides; aryl and aralkyl carboxylic acid chlorides such as benzoic, tolyl and benzyl carboxylic acid chlorides and substituted derivatives thereof being preferred.

For the preparation of the urea or thiourea radicals, the amino group is preferably first reacted with a carbonic acid or thiocarbonic acid derivative such as a chloroformic acid ester or thiophosgene and then with a desired amine $HNR^{101pr}R^{103pr}$ wherein $R_{101pr}$ and $R^{103pr}$ are identical to $R^{101}$ and $R^{103}$ or are precursors which can be transformed into the residues $R^{101}$ and $R^{103}$. The above reactions and their implementation are well known to the person skilled in the art and are described in detail in standard works such as, for example, in "Methoden der Organischen Chemie" [Methods of Organic Chemistry] (Houben-Weyl), Georg Thieme Verlag, Stuttgart.

According to a preferred embodiment of the invention, the carboxyl-protected β-amino acid (IIa) is treated with an equimolar amount or a slight excess of the appropriate sulphonylating agent, for example phenylsulphonyl chloride, or acylating agent, for example mesitylacetyl chloride, with cooling, preferably at about 0° C., in a solvent such as pyridine or dioxane under normal conditions, preferably in the presence of a base such as an amine such as, for example, triethyl amine or diisopropyl ethyl amine, and the mixture is agitated at this temperature for a period of approximately 10 minutes to approximately 2 hours. In the case of sulphonylation, this is followed by agitation at room temperature for a couple of hours, preferably approximately from 2 to 6 hours.

Prior to the synthesis of the linker group L, the radical TP of compound (IIb) can be converted into group Q which can participate in a nucleophilic substitution either as a nucleophilic reagent or as a substrate. If TP carries a nitro group, this will be reduced to the corresponding amino group, which can preferably be carried out by addition of tin(II) chloride to a solution of the compound (IIb) in a solvent such as ethanol and subsequent heating to approximately 50 to 110° C., preferably under reflux of the solvent, for a couple of hours, preferably from approximately 1 to approximately 4 hours, under normal conditions. If TP contains an ether group, the liberation of the corresponding hydroxyl group is preferably carried out by addition of a Lewis acid such as boron tribromide in a solvent such as dichloromethane with cooling, preferably at −78° C., and subsequent agitation for a couple of hours, preferably from 6 to 24 hours, at room temperature. If TP carries a sulpho or a carboxyl group, a conversion into the corresponding sulphonyl or carboxylic acid halide is preferably carried out, for example by reaction with thionyl chloride.

For the reaction of the Q-modified compound (IIb) with compound (IIc), the reactants can be mixed together in approximately equimolar amounts, preferably in the presence of a base such as pyridine or sodium hydride and, if appropriate, in a solvent such as, for example, tetrahydrofuran or dimethyl formamide, under normal conditions at room temperature or with cooling, preferably at approximately 0° C., and agitated for a couple of hours, preferably approximately from 1 to 24 hours, at room temperature or with cooling, for example at about 0° C.

The compounds (IId) thus obtained can be converted into moieties comprising the radicals (II) by conversion of the terminal nitro group, if present, into an acyclic or cyclic guanidine, urea or thiourea group.

For this purpose, the nitro group is first converted into an amino group, preferably by addition of a customary reducing agent such as tin-(II) chloride, if appropriate in the presence of solvents such as ethanol, by agitating the reaction mixture with heating at approximately from 50 to 110° C., preferably under reflux of the solvent, under normal conditions for approximately 2 hours.

For the conversion of the amino group thus obtained into a guanidine, urea or thiourea group, the above amino group can then preferably first be reacted with a carbonic acid ester or thiocarbonic acid ester derivative in a solvent such as dimethyl formamide in the presence of mercury-(II) chloride with cooling, preferably at approximately 0° C., and agitating for approximately from 10 minutes to 3 hours with cooling, preferably at approximately 0° C., and if appropriate subsequently at room temperature. The carbonic acid ester or thiocarbonic acid ester derivative employed can preferably be phosgene, triphosgene, thiophosgene, chloroformic acid esters or thio-pseudourea derivatives, commercially available chloroformic acid esters being preferred for the preparation of the urea derivatives, thiophosgene being preferred for the preparation of the thiourea derivatives and thio-pseudourea derivatives being preferred for the preparation of guanidine derivatives.

The carbamates or isothiocyanates formed in this way can be converted into the corresponding urea, thiourea and guanidine derivatives by reaction with appropriate amines. The amines used are substances of the formula $HNR^{101pr}R^{103pr}$, wherein $R^{101pr}$ and $R^{103pr}$ respectively are identical with $R^{101}$ and $R^{103}$ or are precursors which can be transformed into the radicals $R^{101}$ and $R^{103}$.

According to the invention, the carbamate or isothiocyanate is preferably reacted with an amine at room temperature with stirring for approximately from 1 to 5 hours, preferably approximately from 2 to 3 hours, in the presence of an auxiliary base such as diisopropyl ethyl amine in a solvent such as dimethyl formamide. In the case of the preparation of cyclic guanidine derivatives, the corresponding isothiocyanate is preferably first heated in ethanol for a couple of hours, preferably approximately from 12 to 24 hours, and then heated with a diamine such as diamino ethane in a solvent such as toluene, dimethyl formamide or a mixture of both.

According to a further preferred embodiment, it is also possible to generate the above guanidine, urea or thiourea group on the compound (IIc) in the above manner and then to react the thus modified compound (IIc) with the compound (IIb) in the manner described above.

The compounds obtained according to the process explained above can furthermore be derivatized by removal of protective groups which may be present, further substitution of nitrogen atoms present at preferred positions in the preparation process and/or conversion of the compound obtained into the free acid and/or its physiologically acceptable salts.

For example, the tert.-butoxymethoxycarbonyl groups conventionally used as protective groups for nitrogen atoms are removed in an acidic medium, for example by addition of trifluoroacetic acid.

The ester derivatives according to the invention can be converted into the corresponding free carboxylic acids in a conventional manner, such as, for example, by basic ester hydrolysis.

The conjugates according to the invention can be used as active ingredients for manufacturing medicaments against cancer.

For this purpose, they can be converted into formulations such as tablets, coated tablets, aerosols, pills, granules, syrups, emulsions, suspensions and solutions using inert, non-toxic, pharmaceutically suitable excipients or solvents. Preferably, the conjugates according to the invention are used in an amount such that their concentration in the total mixture is from approximately from 0.5 to 90% by weight, the concentration, inter alia, being dependent on the corresponding indication of the medicament.

The above-mentioned formulations can be produced, for example, by extending the active compounds with solvents and/or excipients having the above properties, where, if appropriate, additionally emulsifiers or dispersants and—in the case of water as the solvent—an organic solvent can be added. Thus, a further embodiment of the invention is a method of manufacturing a pharmaceutical composition by combining at least one of the conjugates (I) with at least one pharmacologically acceptable formulating agent.

Other formulations can, in addition to conjugate (I), contain at least one pharmaceutical active ingredient which is different from conjugate (I). Therefore, pharmaceutical compositions comprising as an active ingredient an effective amount of at least one of the conjugates (I) and at least one pharmaceutical active ingredient which is different from conjugate (I), are a further embodiment of the invention.

A further embodiment of the invention refers to a medicament in dosage unit form comprising an effective amount of conjugate (I) together with an inert pharmaceutical carrier.

A further embodiment of the invention refers to the use of conjugate (I) for manufacturing pharmaceutical compositions for the treatment of cancer.

A further embodiment of the invention refers to a method of treating cancer in mammals comprising the administration of an effective amount of at least one conjugate (I) either alone or in admixture with a diluent or in the form of a medicament.

Administration can be carried out in a customary manner, preferably orally, transdermally or parenterally, for example perlingually, buccally, intravenously, nasally, rectally or inhalationally.

For human use, in the case of oral administration, it is recommended to administer doses of from 0.001 to 50 mg/kg, preferably from 0.01 to 20 mg/kg. In the case of parenteral administration such as, for example, intravenously or via mucous membranes nasally, buccally or inhalationally, it is recommended to use doses of from 0.001 to 0.5 mg/kg.

If appropriate, it may be necessary to depart from the amounts mentioned above, namely depending on the body weight or the type of administration route, on the individual response towards the medicament, the manner of its formulation and the time or interval at which administration takes place. Thus, in some cases it may be sufficient to manage with less than the above mentioned minimum amount, while in other cases the upper limit mentioned must be exceeded. In the case of the administration of relatively large amounts, it may be recommended to divide these into several individual doses over the course of the day.

The conjugates (I) according to the invention are also suitable for use in veterinary medicine. For use in veterinary medicine, the conjugates (I) according to the invention can be administered in a suitable formulation in accordance with general veterinary practice. Depending on the kind of animal to be treated, the veterinary surgeon can determine the nature of use and the dosage.

The present invention provides conjugates for the use in a medical application, in particular for combating cancer.

The invention further provides a method of manufacturing a pharmaceutical composition by combining at least one of the conjugates of the invention with at least one pharmacologically acceptable formulating agent.

The invention further provides a pharmaceutical composition comprising as an active ingredient an effective amount of at least one of the conjugates of the invention and at least one pharmacologically acceptable formulating agent.

The invention further provides a pharmaceutical composition comprising as an active ingredient an effective amount of at least one of the conjugates of the invention and at least one pharmaceutical active ingredient which is different from the conjugates of the invention.

The invention further provides a medicament in dosage unit form comprising an effective amount of a conjugate according to the invention together with an inert pharmaceutical carrier.

The invention further provides a method of combating cancer in mammals comprising the administration of an effective amount of at least one conjugate according to the invention either alone or in admixture with a diluent or in the form of a medicament.

The present invention is illustrated below with the aid of non-restricting Examples and comparative Examples.

The percentages in the description above, in the following tests and in the Examples are—if not stated otherwise—percentages by weight; parts are parts by weight. Solvent ratios, dilution ratios and concentrations in solutions of liquids in liquids are ratios and concentrations by volume.

The yield percentages of the following Examples refer to the starting component which was used in the lowest equivalent amount.

EXAMPLES

The mass determinations were carried out by high-performance liquid chromatography-mass spectrometry (HPLC-MS) using the electron spray ionization (ESI) method or by FAB or MALDI mass spectroscopy.

List of the Abbreviations Used

| | |
|---|---|
| Abu | γ-amino butyric acid |
| ACN | acetonitrile |
| Boc | tert.-butyloxycarbonyl |
| DCM | dichloromethane |
| DIEA | diisopropyl ethyl amine (Hünig's base) |
| DMAP | dimethylamino pyridine |
| DMF | dimethyl formamide |
| DMSO | dimethyl sulphoxide |
| FCS | foetal calf serum |
| Fmoc | fluorenyl-9-methoxycarbonyl |
| HPLC | high-performance liquid chromatography |
| MTBE | methyl tert.-butyl ether |
| NMP | N-methyl pyrrolidone |
| NMRI | nude mice strain |
| RP | reverse phase |
| RT | room temperature |
| RTV | relative tumour volume |
| TFA | trifluoroacetic acid |
| THF | tetrahydrofuran |
| TLC | thin-layer chromatography |

Series I: Synthesis of Starting Materials:

I.1 20-O-L-Valyl-camptothecin trifluoroacetate

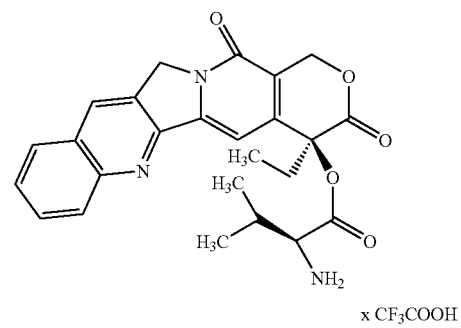

x CF$_3$COOH 14 g (2 eq.) of N-(tert-butoxycarbonyl)-valine-N-carboxyanhydride and 1 g of 4-(N,N-dimethylamino)-pyridine are added to a stirred suspension of 10 g (28.7 mmol) of 20(S)-camptothecin in 500 ml of absolute dichloromethane. After heating under reflux for 4 days, the mixture is concentrated in vacuo. The residue is stirred with 100 ml of MTBE for 20 min. 200 ml of petroleum ether are then added and the mixture is filtered. 14.9 g of the Boc-protected intermediate compound are obtained, which can contain small amounts of D-valine epimer which, however, can be removed without problems after removal of the protective group.

A mixture of 11.65 g of this Boc-protected intermediate compound in 300 ml of dichloromethane and 70 ml of anhydrous trifluoroacetic acid is then stirred at 5° C. for 1 h. After concentrating in vacuo to a small volume, the product is precipitated with diethyl ether and thoroughly washed with diethyl ether. The product is again precipitated from dichloromethane/methanol using diethyl ether. If appropriate, the crude product is again taken up in 40 ml of methanol, 120 ml of MTBE are added, and the solution is cooled to 0° C. The precipitate is filtered off, and 9.4 g (80%) of 20-O-(valyl)-camptothecin trifluoroacetate are obtained after drying.

[TLC: acetonitrile/water (20:1); $R_f$=0.39].

I.2 20-O-[L-Prolyl-L-valyl]-camptothecin trifluoroacetate

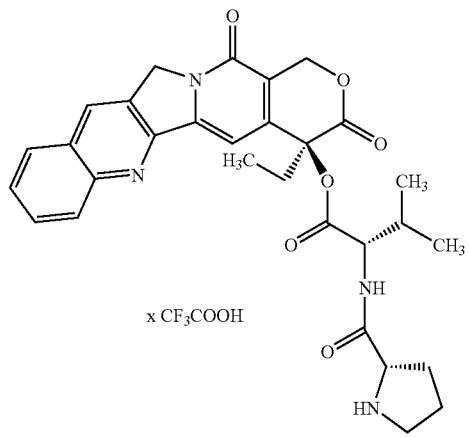

x CF$_3$COOH 1.5 g (2.67 mmol) of the compound from Example I.1 and 1.4 ml of Hunig's base are added to a solution of 1 g (3.2 mmol) of N-tert.-butoxycarbonyl-prolin-N-hydroxy succinimide ester (Boc-Pro-OSu) in 75 ml of DMF, and the mixture is stirred for 6 h. Another 1 g of Boc-Pro-OSu is added, and the mixture is stirred overnight. The solvent is evaporated, and the residue is stirred with water and filtered. The filter residue is dissolved in dichloromethane and precipitated with diethyl ether/petroleum ether (1:1). The recrystallization is repeated and the product is isolated by filtration and dried in vacuo.

Yield: 1.715 g (75%).

[TLC: acetonitrile/water (20:1); $R_f$=0.73].

1.715 g (2.66 mmol) of this Boc-protected intermediate compound are then stirred at 5° C. for 1 h in a mixture of 100 ml of dichloromethane and 20 ml of anhydrous trifluoroacetic acid. After concentrating in vacuo, the product is taken up in dichloromethane/methanol, precipitated with diethyl ether and thoroughly washed with diethyl ether. The product is again precipitated from dichloromethane/methanol using diethyl ether. The precipitate is filtered off and 1.46 g (83%) of the target compound are obtained after drying.

[TLC: acetonitrile/water/glacial acetic acid (5/1/0.2); $R_f$=0.43].

I.3 20-O-[L-Prolyl-L-leucyl]-camptothecin trifluoroacetate

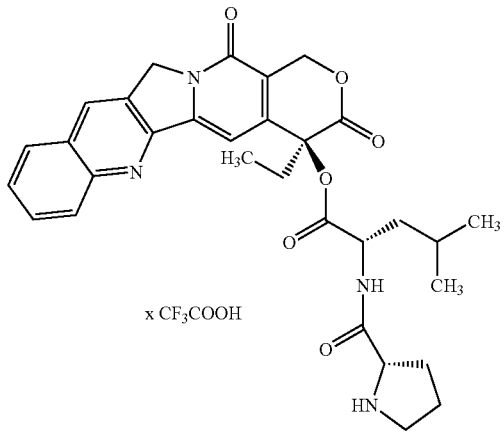

x CF$_3$COOH

This compound is prepared in analogy to Examples I.2 and I.1.

I.4 20-O-[Glycyl-L-prolyl-L-valyl]-camptothecin trifluoroacetate

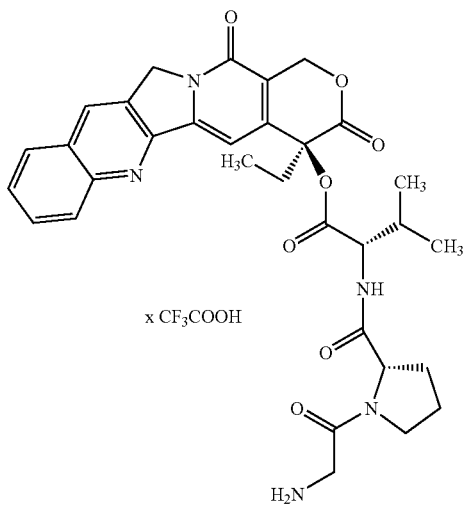

x CF$_3$COOH 371 mg (3 mmol) of 4-dimethylamino pyridine are added to a suspension of 1 g (1.52 mmol) of compound I.2 in 50 ml of dichloromethane and 653 mg (3 mmol) of N-(tert.-butoxycarbonyl)-glycin-N-carboxy-anhydride (Boc-Gly-NCA). After stirring for 1 h the solvent is removed, the residue is stirred with water and filtered. The crude product is purified by flash chromatography using acetonitrile as eluent. Isolation of relevant fractions and evaporation of solvent gives 748 mg (70%) of the protected intermediate product.

The tert.-butoxycarbonyl protecting group is removed as described in Example I.2.

709 mg (93%) of the target compound are obtained.

[TLC: acetonitrile/water/glacial acetic acid (5/1/0.2); $R_f$=0.34].

I.5 20-O-[L-Alanyl-L-prolyl-L-valyl]-camptothecin trifluoroacetate

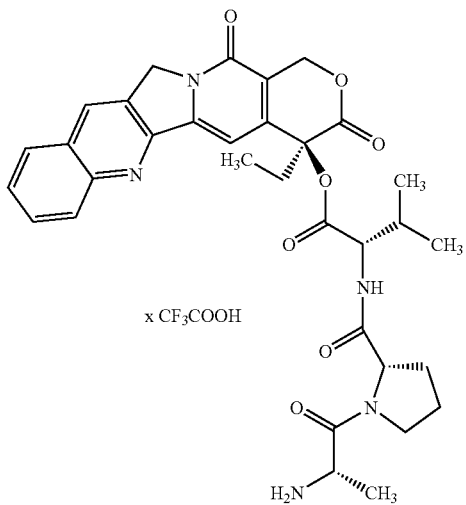

x CF$_3$COOH 80 mg of diisopropyl ethyl amine are added to a suspension of 135 mg (0.2 mmol) of compound I.2 in 25 ml of DMF and 65 mg (0.23 mmol) of N-(tert.-butoxycarbonyl)-alanine-N-hydroxysuccinimide ester (Boc-Ala-OSu). After stirring for 16 h another 32 mg of Boc-Ala-OSu are added, and stirring is continued for 6 h. The solvent is removed, the residue is stirred with water and filtered. The crude product is purified by flash chromatography using acetonitrile as eluent. Isolation of relevant fractions and evaporation of solvent gives 107 mg (73%) of the protected intermediate product.

The tert.-butoxycarbonyl protecting group is removed as described in Example I.2. 92 mg (87%) of the target compound are obtained.

[TLC: acetonitrile/water/glacial acetic acid (5/1/0.2); $R_f$=0.32].

I.6 20-O-[L-Aspartyl-L-prolyl-L-valyl]-camptothecin trifluoroacetate

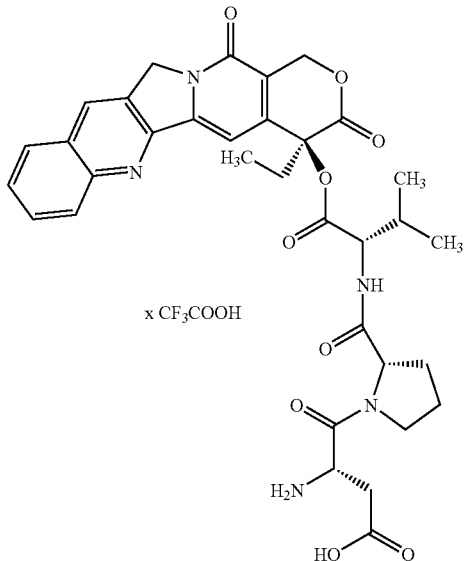

x CF$_3$COOH 12 mg of 1-hydroxy-1H-benzotriazole (HOBT), 14 mg (0.073 mmol) of N-(3-dimethylaminopropyl)-N'-ethylcarbodiimide hydrochloride and 24 mg of diisopropyl ethyl amine are added to a solution of 21 mg (0.073 mmol) of N-(tert.-butoxycarbonyl)-aspartatic acid-γ-tert.-butylester (Boc-Asp(O-tBu)—OH) in 10 ml of DMF. The mixture is stirred for 30 min. Subsequently, 40 mg (0.061 mmol) of compound I.2 are added. After sonification for 2 h, the reaction is complete and the solvent is removed. The residue is distributed between dichloromethane and water. The organic phase is dried over sodium sulphate and concentrated. The residue is precipitated from dichloromethane with a mixture of petroleum ether and diethyl ether. 47 mg (95%) of the protected intermediate compound are obtained.

Both the tert.-butyl ester and the tert.-butoxycarbonyl protecting group are removed as described in Example I.2. 33 mg (74%) of the target compound are obtained.

[TLC: acetonitrile/water/glacial acetic acid (5/1/0.2); $R_f$=0.28].

Further camptothecin peptide conjugates shown in Table 1 are synthesized in analogy to standard procedures as described in "Methoden der Organischen Chemie" [Methods of Organic Chemistry] (Houben Weyl), 4$^{th}$ ed., Vol. XV Parts 1 and 2, Georg Thieme Verlag, Stuttgart 1974, or by Hans-Dieter Jakubke and Hans Jeschkeit in Aminosäuren, Peptide, Proteine [Amino Acids, Peptides, and Proteins], Verlag Chemie, Weinheim 1982 or as exemplified in the previous Examples.

TABLE 1

| Ex. | Compound | $R_f$ |
|---|---|---|
| I.7 | 20-O-[L-Asn-L-Pro-L-Val]-camptothecin trifluoroacetate | 0.25 [*] |
| I.8 | 20-O-[L-His-L-Pro-L-Val]-camptothecin bis-trifluoroacetate | 0.17 [*] |
| I.9 | 20-O-[L-Nva-L-Pro-L-Val]-camptothecin trifluoroacetate | 0.38 [*] |
| I.10 | 20-O-[Gly-L-Pro-L-Leu]-camptothecin trifluoroacetate | 0.27 [*] |

[*] acetonitrile/water/glacial acetic acid (5/1/0.2)

I.11 N-Leucyl-quinolone-a trifluoroacetate

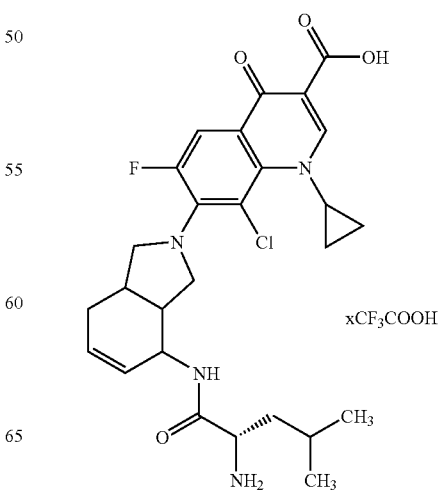

xCF$_3$COOH 108 mg of 1-hydroxy-1H-benzotriazole (HOBT), 122.3 mg (0.64 mmol) of N-(3-di-methylaminopropyl)-N'-ethyl-carbodiimide hydrochloride and 206 mg of diisopropyl ethyl amine are added to a solution of 122 mg (0.53 mmol) of N-(tert.-butoxycarbonyl)-leucine (Boc-Leu-OH) in 10 ml of DMF. The mixture is stirred for 30 min. Subsequently, 200 mg (0.48 mmol) of quinolone-a are added. After stirring for 4 h the reaction is complete and the solvent is removed. The residue is stirred with water and filtered. The residue is precipitated from dichloromethane with diethyl ether. 247 mg (74%) of the protected intermediate compound are obtained.

The tert.-butoxycarbonyl protecting group is removed as described in Example I.1.

245 mg (98%) of the target compound are obtained.

[TLC: acetonitrile/water/glacial acetic acid (5/1/0.2); $R_f$=0.46].

I.12 N-(Alanyl-prolyl-leucyl)-quinolone-a trifluoroacetate

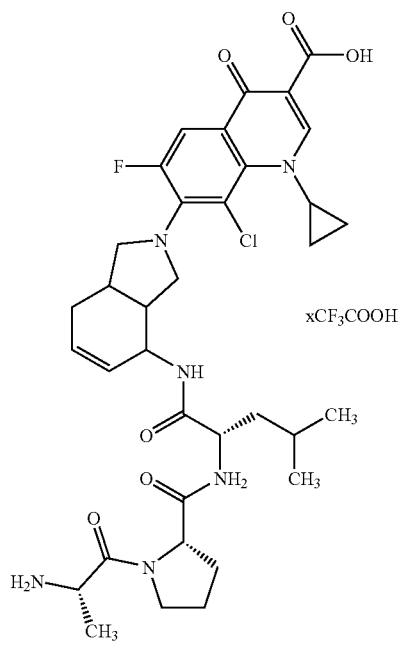

Starting from compound I.11 this conjugate is synthesized in analogy to Example I.5.

[TLC: acetonitrile/water/glacial acetic acid (5/1/0.2); $R_f$=0.35].

I.13 N-(Gycyl-prolyl-leucyl)-quinolone-a trifluoroacetate

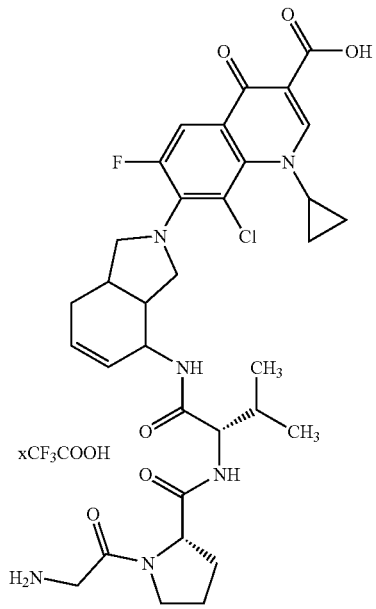

Starting from compound I.11 this conjugate is synthesized in analogy to Example I.5.

[TLC: acetonitrile/water/glacial acetic acid (5/1/0.2); $R_f$=0.4].

I.14 N-(Glycyl-prolyl-valyl)-quinolone-a trifluoroacetate

This conjugate is synthesized in analogy to Example I.12.
[TLC: acetonitrile/water/glacial acetic acid (5/1/0.2); $R_f=0.5$].

I.15 7-Ethyl-10-(L-valyl-oxy)-camptothecin trifluoroacetate

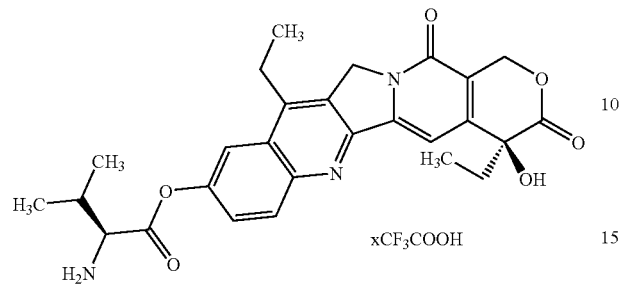

A suspension of 300 mg (764 μmol) 20(S)-7-ethyl-10-hydroxy-camptothecin in 50 ml of absolute dichloromethane is treated with stirring with 372 mg (1.5 μmol) of N-(tert-butoxycarbonyl)-valine-N-carboxyanhydride and 30 mg of 4-(N,N-dimethylamino)-pyridine. After heating under reflux for 2 hours 200 ml of dichloromethane and 50 ml of water are added; the mixture is shaken in a separation funnel, the organic phase is separated and concentrated in vacuo. The desired product is purified by flash-chromatography at silica gel employing petroleum ether/ethyl acetate (3:1→1:1) as eluent. Relevant fractions are collected and concentrated in vacuo. 140 mg (31%) of the 10-Boc-valine-oxy substituted intermediate compound are obtained.

139 mg (230 μmol) of this intermediate compound are then stirred at 5° C. for 1 h in a mixture of 10 ml of dichloromethane and 2 ml of anhydrous trifluoroacetic acid. After concentrating in vacuo to a small volume, the product is precipitated with diethyl ether and thoroughly washed with diethyl ether. The product is again precipitated from dichloromethane/methanol using diethyl ether. The precipitate is filtered off and 122 mg (86%) of 20(S)-7-ethyl-10-(valyloxy)-camptothecin trifluoroacetate are obtained after drying. [TLC: acetonitrile/water (10:1) $R_f=0.25$].

I.16 7-Ethyl-10-tert-butoxycarbonyloxy-camptothecin trifluoroacetate

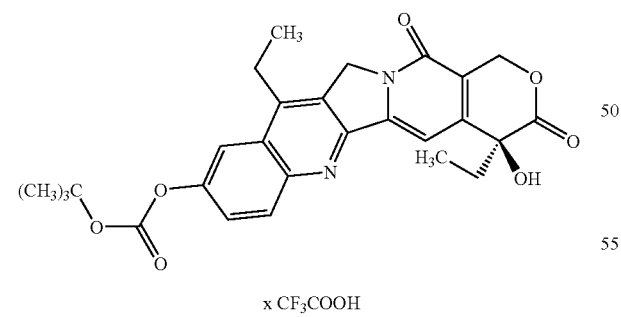

A suspension of 300 mg (764 μmol) 20(S)-7-ethyl-10-hydroxy-camptothecin in 120 ml of dichloromethane/dimethyl formamide (8:1) is treated with stirring with 1668 mg (7.65 mmol) of Boc₂O and 988 mg of N-ethyl-N-diisopropylamine. After stirring for 3 days 200 ml of dichloromethane and 50 ml of 5% strength aqueous sodium bicarbonate are added; the mixture is shaken in a separation funnel, the organic phase is separated, washed with water and concentrated in vacuo. The product is precipitated from dichloromethane using diethyl ether and petroleum ether. 345 mg (92%) of the 10-tert-butoxycarbonyl-oxy intermediate compound are obtained.
[TLC: acetonitrile/water (20:1) $R_f=0.6$].

I.17  20(S)-7-Ethyl-10-O-[glycyl-L-prolyl-L-valyl]-camptothecin trifluoroacetate

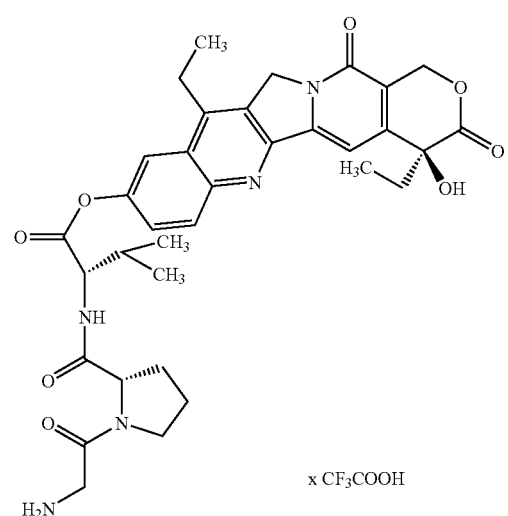

Synthesis in analogy to example I.4 starting from the compound described in example I.15.

I.18  20(S)-7-Ethyl-10-hydroxy-20-O-[glycyl-L-prolyl-L-valyl]-camptothecin trifluoroacetate

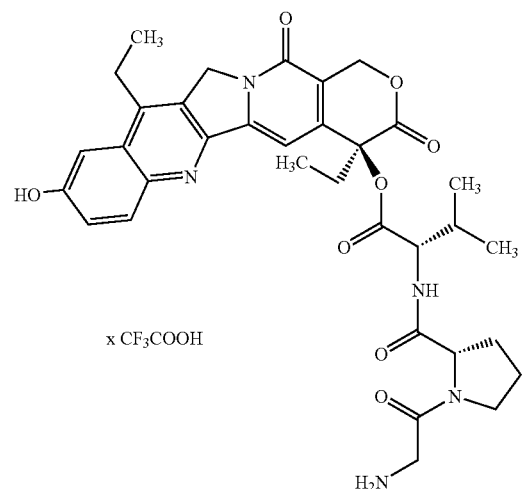

Synthesis in analogy to example I.4 starting from the compound of example I.16.

Series II: Preparation of Integrin Ligands

Example II.1

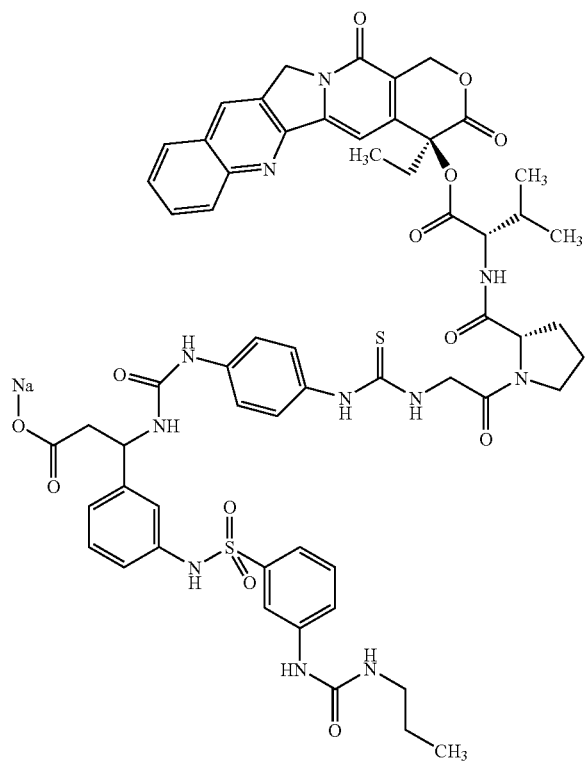

II.1-a 3-Amino-3-[3-(propylaminocarbonylamino-phenyl-sulphonylamino)-phenyl]-propionic acid

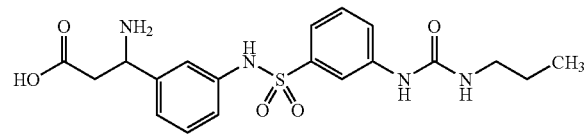

1.2 g of polystyrene Wang resin (loading 1.08 mmol/g) are swollen in DMF. The solvent is filtered off with suction and a solution of 841 mg of (3R,S)-3-(9-fluorenyl-methoxycarbonylamino)-3-(3-nitrophenyl)-propionic acid (amino acid reagent) in 15 ml of DMF is added. After shaking at room temperature for 15 min, 350 µl of pyridine and 540 mg of 2,6-dichlorobenzoyl chloride are added to the suspension. The mixture is shaken overnight at room temperature. The resin is then washed with DMF, methanol and DCM. A mixture of the resin and a solution of 5400 mg of tin(II) chloride dihydrate in 12 ml of NMP is shaken overnight at room temperature. The resin is then washed with NMP, methanol, THF and DCM. The resin is admixed with a solution of 450 µl of DIEA in 500 µl of THF and a solution of 430 mg of 3-nitrobenzenesulphonyl chloride in 500 µl of THF. The mixture is shaken overnight at room temperature. The resin is then washed with DMF, methanol and THF.

The resultant resin is admixed with a solution of 5400 mg of tin(II) chloride dihydrate in 12 ml of NMP, and the mixture is shaken overnight at room temperature. The resin is then treated with NMP, methanol, THF and DCM. The resin is treated with a solution of 500 µl of DIEA in 12 ml of THF/DCM (1:1) and a solution of 2757 mg of 4-nitrophenyl-chloroformic acid ester in 12 ml of THF/DCM (1:1). After shaking at room temperature for 45 min, it is washed with THF and DMF, and a solution of 943 mg of propyl amine and 2780 µl of DIEA in 20 ml of NMP is added. After shaking for 10 h, the resin is washed with DMF, methanol, THF and DCM.

For the removal of the product, the resin is shaken for 1 h with 12 ml of TFA/DCM and filtered off, and the filtrate is concentrated in vacuo.

II.1 3-(4-Aminophenylaminocarbonylamino)-3-[3-(3-propylaminocarbonylamino-phenyl-sulphonylamino)-phenyl]-propionic acid

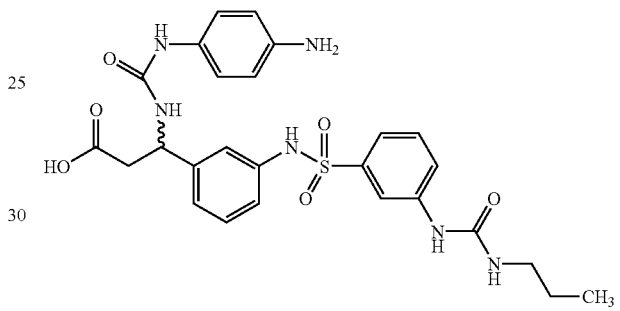

A mixture of 70 mg (0.166 mmol) of the compound II.1-a, 54 mg (2 eq) of 4-nitrophenyl isocyanate and 10 ml of DMF is stirred for 1 h. The mixture is concentrated and the residue is purified by flash chromatography on silica gel using dichloromethane/methanol/17% strength aqueous ammonia (15:2:0.2). After precipitation from dichloromethane/methanol using diethyl ether, 29 mg (30%) of intermediate-a are obtained.

This intermediate-a is dissolved in methanol and hydrogenated over palladium/carbon. The catalyst is separated off, the solution is concentrated and the residue is lyophilized from dioxane/water. 18 mg (74%) of the target compound are obtained.

II.2: Enantiomer A of II.1 3-(4-aminophenylaminocarbonylamino)-3-[3-(3-propylaminocarbonylamino-phenyl-sulphonylamino)-phenyl]-propionic acid

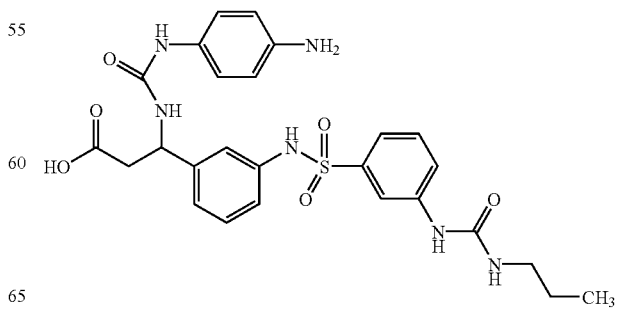

II.2.a 3-(Amino)-3-(3-nitrophenyl)-propionic acid hydrochloride

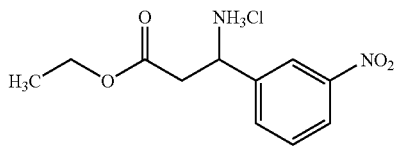

A mixture of 151 g of 3-nitrobenzaldehyde, 94 g of ammonium acetate, 127 g of malonic acid and 1 L of 2-propanol was heated under reflux for 5 h. The solution was filtered and the precipitate was washed with 0.7 L of hot 2-propanol. The crude product was dried in vacuo, suspended in 1.5 L of water, 1 N hydrochloric acid was added, and the mixture was filtered. The filtrate was concentrated to yield 146 g.

$^1$H-NMR (400 MHz, D$_4$-methanol): δ=3.09 (m, 2H), 4.88 (m, 1H), 7.74 (t, 1H), 7.90 (d, 1H), 8.33 (d, 1H), 8.43 (s, 1H).

II.2.b Ethyl 3-amino-3-(3-nitrophenyl)-propanoate hydrochloride

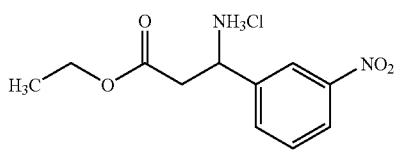

Hydrogen chloride was passed into a suspension of 60 g of 3-amino-3-(3-nitrophenyl)-propionic acid hydrochloride from Example II.2.a in 660 ml of ethanol for 1 h. The reaction mixture was then heated under reflux for 4 h and then cooled and concentrated. 62 g of a white solid were obtained.

$^1$H-NMR (400 MHz, D$_4$-methanol): δ=1.22 (t, 3H), 3.12 (dd, 1H), 3.20 (dd, 1H), 4.18 (q, 2H), 4.95 (t, 1H), 7.77 (t, 1H), 7.94 (d, 1H), 8.35 (d, 1H), 8.43 (s, 1H).

II.2.c Ethyl 3-{[(allyloxy)-carbonyl]-amino}-3-(3-nitrophenyl)-propanoate

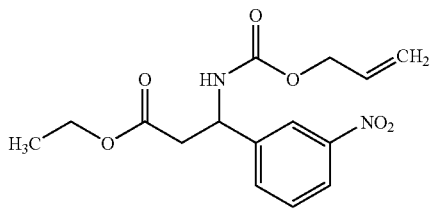

A mixture of 48.8 g of diisopropyl ethyl amine, 24.8 g of allyloxycarbonyl chloride and 150 ml of dichloromethane was added to a mixture of 41.2 g of ethyl 3-amino-3-(3-nitrophenyl)-propioniate hydrochloride from Example II.2.b and 350 ml of dichloromethane at 0° C. After stirring for 30 min, the mixture was washed with water, the organic phase was dried over magnesium sulphate and concentrated to give a white solid (yield: 56.4 g).

$^1$H-NMR (400 MHz, CDCl$_3$): δ=1.18 (t, 3H), 2.90 (d, 2H), 4.11 (q, 2H), 4.58 (m, 2H), 5.15–5.40 (m, 3H), 5.90 (m, 1H), 6.05 (m, 1H), 7.55 (t, 1H), 7.70 (d, 1H), 8.12 (d, 1H), 8.19 (s, 1H).

II.2.d Ethyl 3-{[(allyloxy)-carbonyl]-amino}-3-(3-aminophenyl)-propanoate

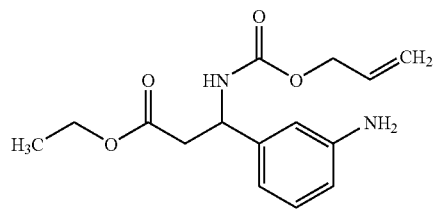

64.6 g of tin-(II) chloride were added to a solution of 18.8 g of ethyl 3-{[(allyloxy)-carbonyl]-amino}-3-(3-nitrophenyl)-propanoate from Example II.2.c in 245 ml of ethanol, and the mixture was heated to reflux for 2 h. The reaction mixture was hydrolized with 300 ml of aqueous 2N sodium hydroxide solution, then filtered through silica gel, and the filtrate was washed with dichloromethane. The organic phase was dried over magnesium sulphate and concentrated to yield 13.1 g of a white solid.

$^1$H-NMR (400 MHz, CDCl$_3$): δ=1.19 (t, 3H), 2.80 (m, 2H), 4.06 (q, 2H), 4.57 (m, 2H), 5.07 (m, 1H), 5.20 (d, 1H), 5.29 (d, 1H), 5.70 (m, 1H), 5.89 (m, 1H), 6.57 (d, 1H), 6.62 (s, 1H), 6.68 (d, 1H), 7.11 (t, 1H).

II.2.e Ethyl 3-{[(allyloxy)-carbonyl]-amino}-3-{{3-{[(3-nitrophenyl)-sulfonyl]-amino}-phenyl}}-propanoate

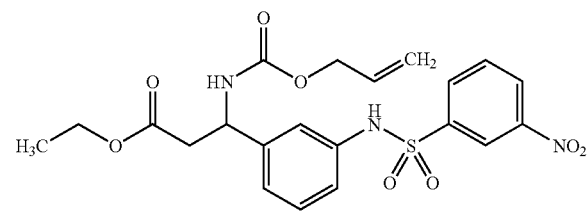

3-Nitrophenylsulphonyl chloride was added at 0° C. to a solution of 11.6 g ethyl 3-{[(allyloxy)-carbonyl]-amino}-3-(3-aminophenyl)-propanoate from Example II.2.d in 110 ml of pyridine. After a reaction time of 2 h, the mixture was concentrated, 1 N hydrochloric acid was added, and the solution was extracted with dichloromethane. After drying the organic phase over magnesium sulphate, the solvent was removed and the crude product was purified by chromatography on silica gel (dichloromethane/methanol=40:1) to give 17.8 g of a solid.

II.2.f Ethyl 3-{[(allyloxy)-carbonyl]-amino}-3-{{3-{[(3-aminophenyl)-sulfonyl]amino}-phenyl}}-propanoate

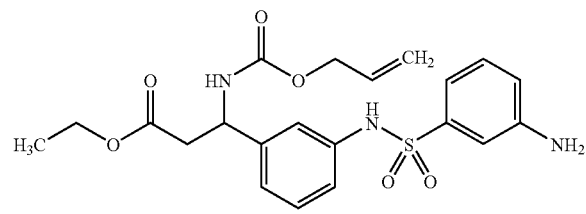

43.5 g of tin-(II) chloride were added to a solution of 17.8 g of ethyl 3-{[(allyloxy)-carbonyl]-amino}-3-{{3-{[(3-nitrophenyl)-sulfonyl]-amino}-phenyl}}-propanoate from Example II.2.e in 165 ml of ethanol, and the mixture was heated to reflux for a period of time of 2 h. The reaction mixture was hydrolized with 200 ml of aqueous 2N sodium hydroxide solution, then filtered through silica gel and washed with dichloromethane. The organic phase was dried over magnesium sulphate and concentrated to yield 9.2 g of a solid.

The material was separated into its enantiomers by chiral chromatography with the selector Bayer-CSP(N-methacryloyl-L-valin-3-pentylamide) using THF as solvent. Similar selectors have been described in the literature (Angew. Chem. Int. Ed. Engl. 30, 1662–1664 (1991)). This separation resulted in the two product fractions 1 and 2.

$^1$H-NMR (400 MHz, CDCl$_3$): δ=1.18 (t, 3H), 2.80 (m, 2H), 3.95 (br.s, 2H), 4.08 (q, 2H), 4.54 (m, 2H), 5.08 (m, 1H), 5.22 (d, 1H), 5.30 (d, 1H), 5.78 (m, 1H), 5.90 (m, 1H), 6.58 (s, 1H), 6.75 (d, 1H), 6.88 (d, 1H), 6.95 (s, 1H), 7.05 (d, 1H), 7.11 (d, 1H), 7.15–7.22 (m, 3H).

II.2.g Ethyl 3-{[(allyloxy)-carbonyl]-amino}-3-{{3-{[(3-{[(propylamino)-carbonyl]-amino}-phenyl)-sulfonyl]-amino}-phenyl}}-propanoate

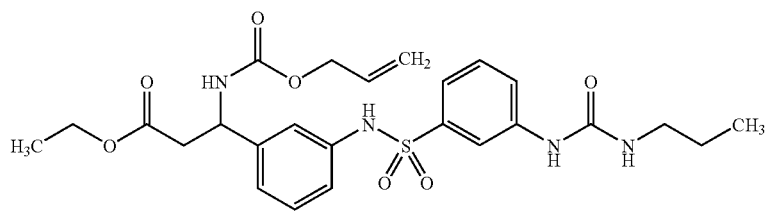

9.6 g of propyl isocyanate were added to a solution of 50 g of enantiopure ethyl 3-{[(allyloxy)-carbonyl]-amino}-3-{{3-{[(3-aminophenyl)-sulfonyl]-amino}-phenyl}}-propanoate from fraction 1 from Example II.2.f in 500 ml of dioxane, and the mixture was stirred for 18 h at 50° C. After evaporation of the solvent, 1.5 L of 1 M hydrochloric acid were added, and the solution was extracted with dichloromethane. The organic phase was dried over magnesium sulphate and concentrated. Chromatography on silica gel (dichloromethane/methanol=30:1) yielded 19.1 g of the compound.

$^1$H-NMR (400 MHz, CDCl$_3$): δ=0.90 (t, 3H), 1.19 (t, 3H), 1,52 (q, 2H), 2.83 (m, 2H), 3.18 (m, 2H), 4.10 (q, 2H), 4.56 (m, 2H), 5.05–5.35 (m, 3H), 5.90 (m, 1H), 6.18 (m, 1H), 6.77 (m, 1H), 6.88 (s, 1H), 7.00–7.45 (m, 8H), 7.98 (m, 1H).

II.2.h Ethyl 3-amino-3-{{3-{[(3-{[(propylamino)-carbonyl]-amino}-phenyl)-sulfonyl]-amino}-phenyl}}-propanoate

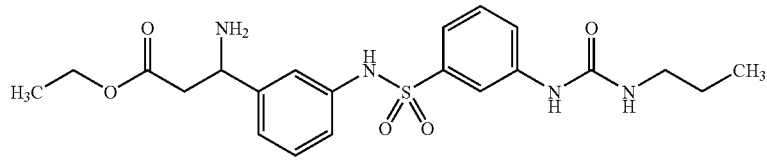

2.57 ml of acetic acid, 5.32 ml of tributyltin hydride and 177 mg of bis(triphenyl phosphine) palladium(II) chloride were added to a solution of 9.58 g of ethyl 3-{[(allyloxy)-carbonyl]-amino}-3-{{3-{[(3-{[(propylamino)-carbonyl]-amino}-phenyl)-sulphonyl]-amino}-phenyl}}-propanoate from Example II.2.g in 245 ml of dichloromethane, and the resultant mixture was stirred at room temperature for 22 h. An aqueous solution of sodium bicarbonate was added, and the mixture was extracted with dichloromethane. After drying the organic phase over magnesium sulphate, the solvent was removed, and the crude product was purified by chromatography on silica gel (dichloromethane/methanol=10:1) to give 2.30 g of the desired compound.

$^1$H-NMR (400 MHz, CDCl$_3$): δ=0.88 (t, 3H), 1.20 (t, 3H), 1,50 (q, 2H), 2.60 (dd, 1H), 2.67 (dd, 1H), 3.17 (m, 2H), 4.11 (q, 2H), 4.33 (m, 1H), 5.21 (m, 1H), 6.89 (d, 1H), 7.07 (d, 1H), 7.16 (t, 1H), 7.22–7.34 (m, 5H), 7.38 (s, 1H), 7.49 (s, 1H).-

II.2 3-(4-Aminophenylaminocarbonylamino)-3-[3-propy-laminocarbonylamino-phenyl-sulphonylamino)-phenyl]-propionic acid, enantiomer A diastereoisomer A

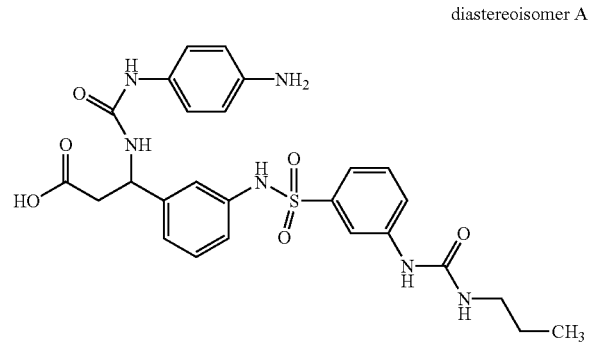

A mixture of 700 mg (1.56 mmol) of the compound II.2.h, 510 mg (2 eq) of 4-nitrophenyl isocyanate and 100 ml of DMF is stirred for 1 h. The mixture is concentrated, and the residue is purified by flash chromatography on silica gel using dichloromethane/methanol/17% strength aqueous ammonia (15:2:0.2). After precipitation from dichloromethane/methanol using diethyl ether, 290 mg (30%) of intermediate-a are obtained. This intermediate-a is dissolved in methanol and hydrogenated on palladium/carbon. The catalyst is separated off, the solution is concentrated, and the residue is lyophilized from dioxane/water. 204 mg (74%) of intermediate-b are obtained. 200 mg (0.34 mmol) of intermediate-b are dissolved in methanol and admixed with 1 ml of an aqueous 2M lithium hydroxide solution. After 6 h, additional 300 µl of lithium hydroxide solution are added, and the mixture is stirred until the de-esterification is complete. The solution is concentrated, and the product is precipitated from dichloromethane using diethyl ether. 141 mg (75%) of compound II.2 are obtained.

[TLC: (acetonitrile/water/glacial acetic acid (10/1/0.1); $R_f$=0.6].

[ESI-MS: m/e=555 (M+H)$^+$].

II.3: 3-(4-Aminophenylaminocarbonylamino)-3-[3-(propy-laminocarbonylamino-phenyl-sulphonylamino)-phenyl]-propionic acid, enantiomer B The same protocol as for the synthesis of enantiomer A was used except that fraction 2 of ethyl 3-{[(allyloxy)-carbonyl]-amino}-3-{{3-{[(3-aminophenyl)-sulfonyl]-amino}-phenyl}}-propanoate was used after the seperation of the enantiomers.

Series III: Preparation of Conjugates of Integrin Ligands with Cytotoxic Agents

General Procedure A (Thiourea Linkage):

9.6 µl (0.13 mmol) of thiophosgene are added to a solution of 0.09 mmol of an integrin ligand from series II 10 mL of dioxane/water (1:1). After stirring at room temperature for 15 min, 94 µL (0.54 mmol) of Hunig's base are added, and the mixture is stirred for a further 10 min and then concentrated. The residue is taken up in dichloromethane and precipitated using diethyl ether. The obtained isothiocyanates are reacted in the next step without further purification.

0.09 mmol of the isothiocyanate is dissolved in 15 ml of DMF, and the resultant solution is admixed with 0.08 mmol of one of the peptide conjugates in series I in the presence of 43 µL of Hiinig's base. After stirring at room temperature for 30 min, the mixture is concentrated, and the residue is stirred with water. The residue is separated and dissolved in methanol/dichloromethane. The product is precipitated using diethyl ether.

If neccessary, further purification is done by flash chromatography on silica gel. Appropriate eluent systems are:
dichloromethane/methanol/17% strength aqueous ammonia (15/3/0.3),
dichloromethane/methanol/17% strength aqueous ammonia (16/2/0.2).

The relevant fractions are collected, concentrated, and the target products are isolated by precipitation from methanol/dichloromethane using diethyl ether. In many cases conjugates are transformed into respective sodium salts to improve water solubility. Therefore, the conjugates are suspended in water, and 1–2 equivalents of an aqueous 0.01 N solution of sodium hydroxide are added until solution occurs and a pH of about 8 is reached. Subsequent lyophilisation yields the sodium salts of conjugates of integrin ligands with cytotoxic agents.

General Procedure B (Urea Linkage)

16 µL of Hünig's base are added to a solution of 0.07 mmol of 4-nitrophenyl chloroformic acid ester in 10 ml of THF. Subsequently, 0.05 mmol of one of the integrin ligands from series II dissolved in a mixture of 5 mL of THF and 0.5 mL of DMF are added in small portions, and the resultant mixture is stirred at room temperature for 10 min. 0.04 mmol of a peptide conjugate from series I dissolved in 2 mL of DMF and 24 µL of Hünig's base are added, and the resultant mixture is stirred for an additional hour at room temperature. The solvent is removed, and the residue is purified by flash chromatography on silica gel. Appropriate eluent mixtures are:
dichloromethane/methanol/17% strength aqueous ammonia (15/3/0.3),
dichloromethane/methanol/17% strength aqueous ammonia (16/2/0.2).

The relevant fractions are collected, concentrated, and the target products are isolated by precipitation from methanol/dichloromethane using diethyl ether. In many cases conjugates are transformed into the respective sodium salts to improve water solubility. Therefore, the conjugates are suspended in water, and 1–2 equivalents of an aqueous 0.01 N solution of sodium hydroxide are added, until solution occurs and a pH of about 8 is reached. Subsequent lyophilisation yields the sodium salts of conjugates of integrin ligands with cytotoxic agents.

The following eluent systems have been used for TLC:
1) dichloromethane/methanol/17% strength aqueous ammonia (15/4/0.5), and
2) acetonitrile/water/glacial acetic acid (10/1/0.1).

Example 1

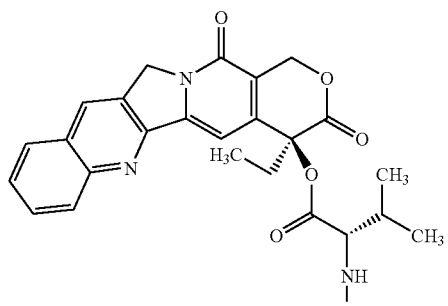

-continued
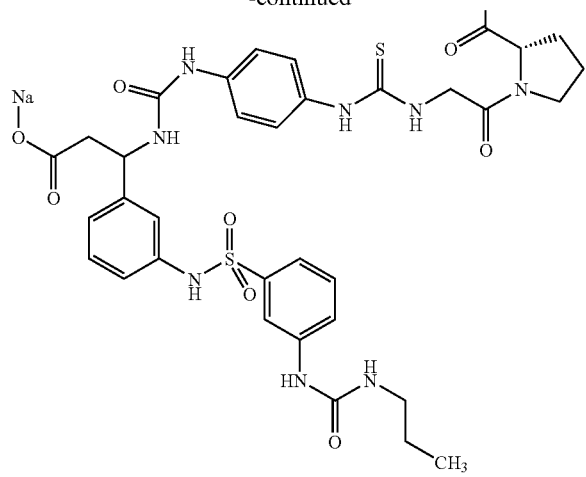
Diastereoisomer A:
Educts: I.4, II.2
Procedure: A
Yield: 51% (2 steps)
$R_f=0.37^{1)}$
[ESI-MS: m/e=1198=(M (acid)+H)$^+$]
Example 2
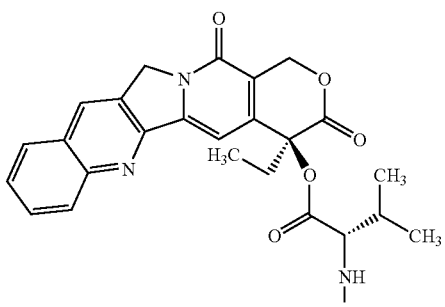
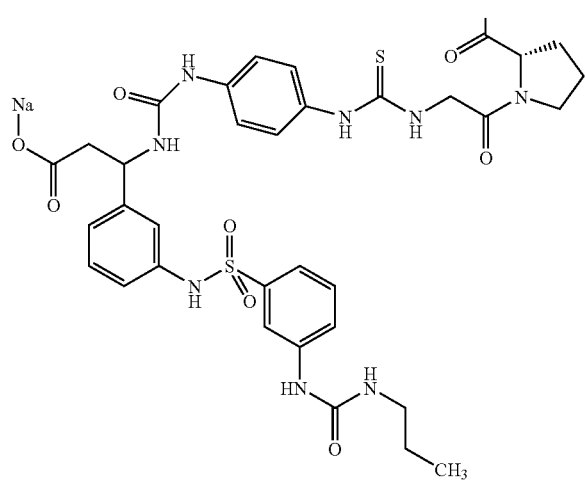
Diastereoisomer b:
Educts: I.4, II.3
Procedure: A
Yield: 51% (2 steps)
$R_f=0.37^{1)}$
[ESI-MS: m/e=1198=(M (acid)+H)$^+$]
Example 3
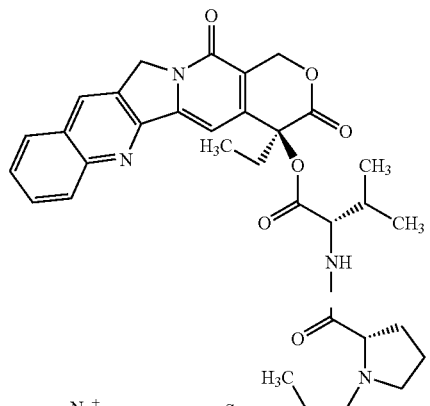
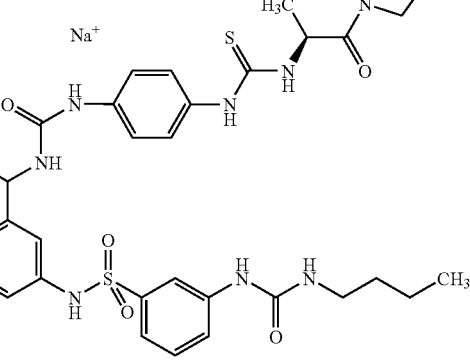
Diastereoisomer A:
Educts: I.5, II.2
Procedure: A
Yield: 69% (2 steps)
$R_f=0.39^{1)}$
[ESI-MS: m/e=1212=(M (acid)+H)$^+$]
Example 4
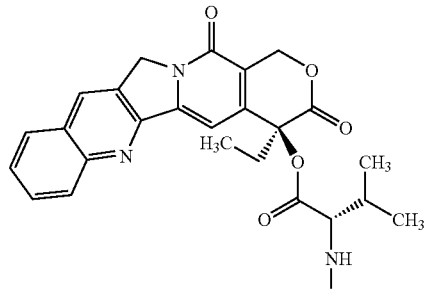

-continued

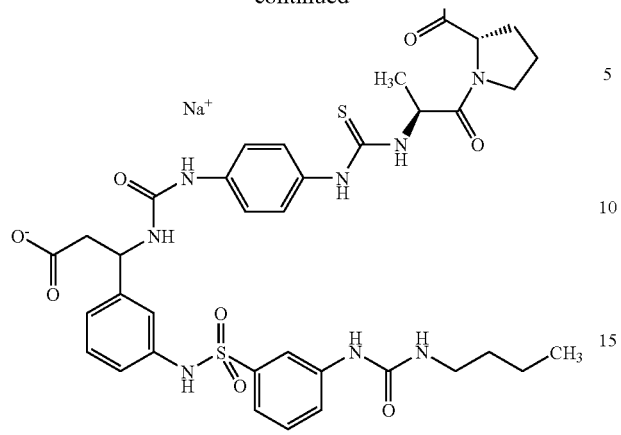

Diastereoisomer B:
Educts: I.5, I.3
Procedure: A
Yield: 66% (2 steps)
$R_f = 0.39^{1)}$
[ESI-MS: m/e=1212=(M (acid)+H)$^+$]

Example 5

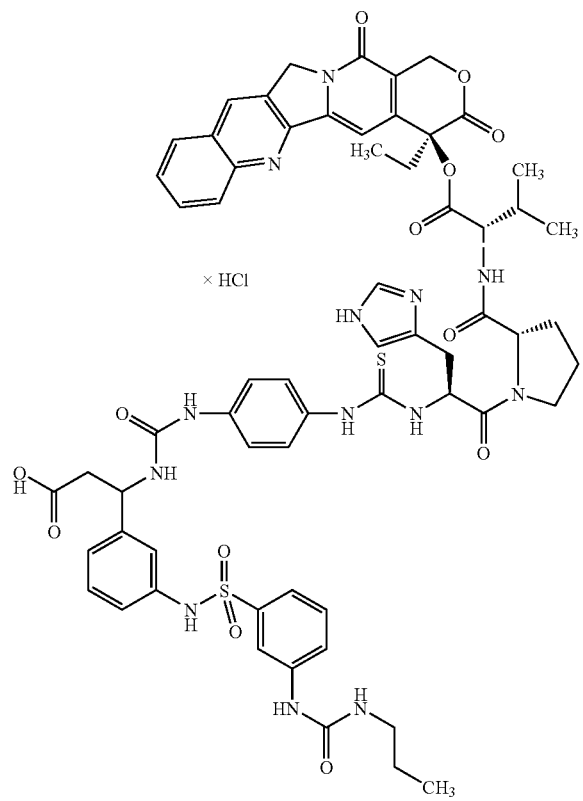

Diastereoisomer A:
Educts: I.8, II.2
Procedure: A

This compound is transformed into the hydrochloride (not into the sodium salt).

The betain is suspended in water and treated with 1 equivalent of 0.1 N hydrochloric acid.

The same volume of dioxane is added, and the mixture is lyophilized.

Yield: 5% (2 steps)
$R_f = 0.45^{1)}$
[ESI-MS: m/e=1278=(M (acid)+H)$^+$]

Example 6

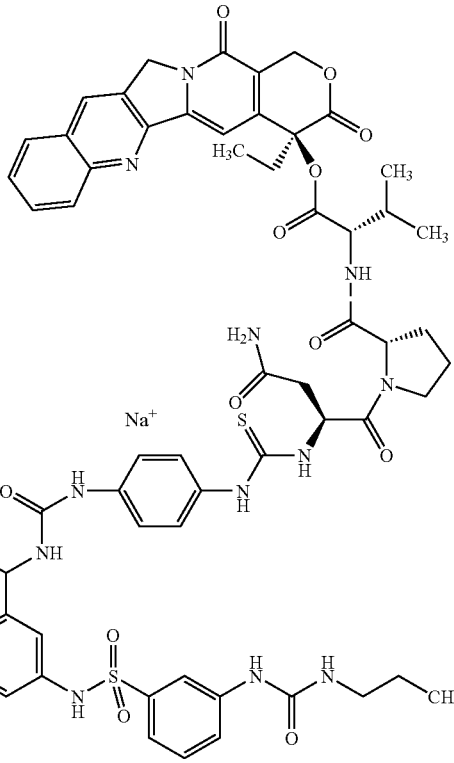

Diastereoisomer A:
Educts: I.7, II.2
Procedure: A
Yield: 44% (2 steps)
$R_f = 0.3^{1)}$
[ESI-MS: m/e=1255=(M (acid)+H)$^+$]

Example 7

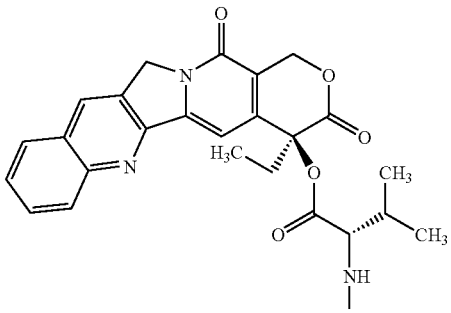

-continued
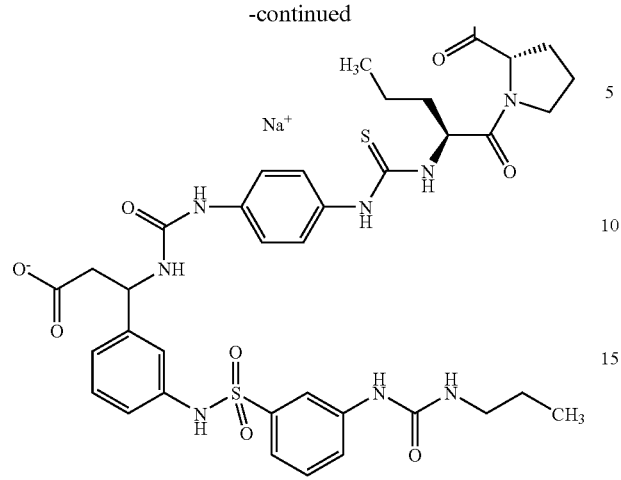
Diastereoisomer A:
Educts: I.9, II.2
Procedure: A
Yield: 57% (2 steps)
$R_f=0.44^{1)}$
[ESI-MS: m/e=1240=(M (acid)+H)$^+$]
Example 8
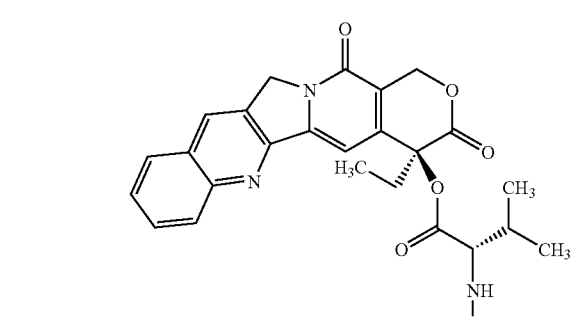
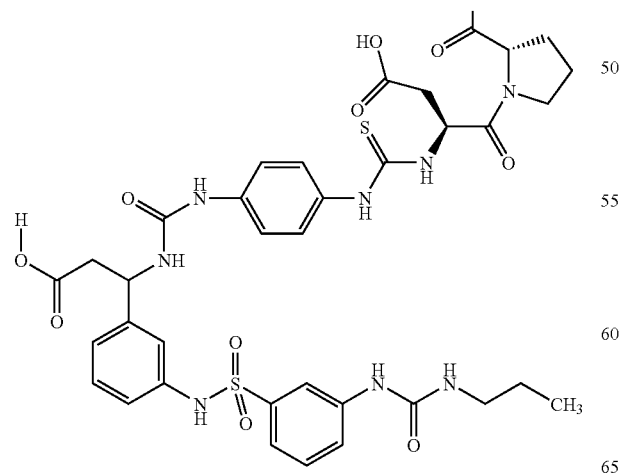
Diastereoisomer A:
Educts: I.6, II.2
Procedure: A, no transformation into sodium salt.
Yield: 12%
$R_f=0.13^{1)}$
[ESI-MS: m/e=1256=(M+H)$^+$]
Example 9
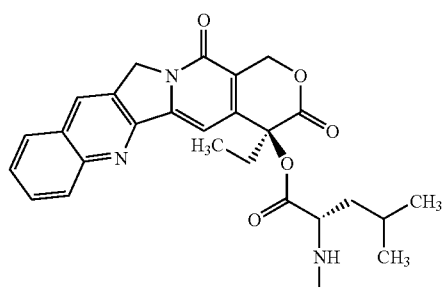
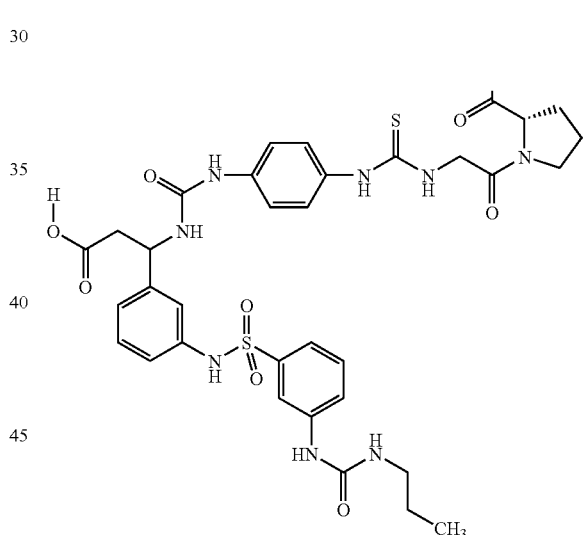
Diastereoisomer B:
Educts: I.10, II.3
Procedure: A, no transformation into sodium salt.
Yield: 40% (2 steps)
$R_f=0.41^{1)}$
[ESI-MS: m/e=1212=(M+H)$^+$]

Example 10
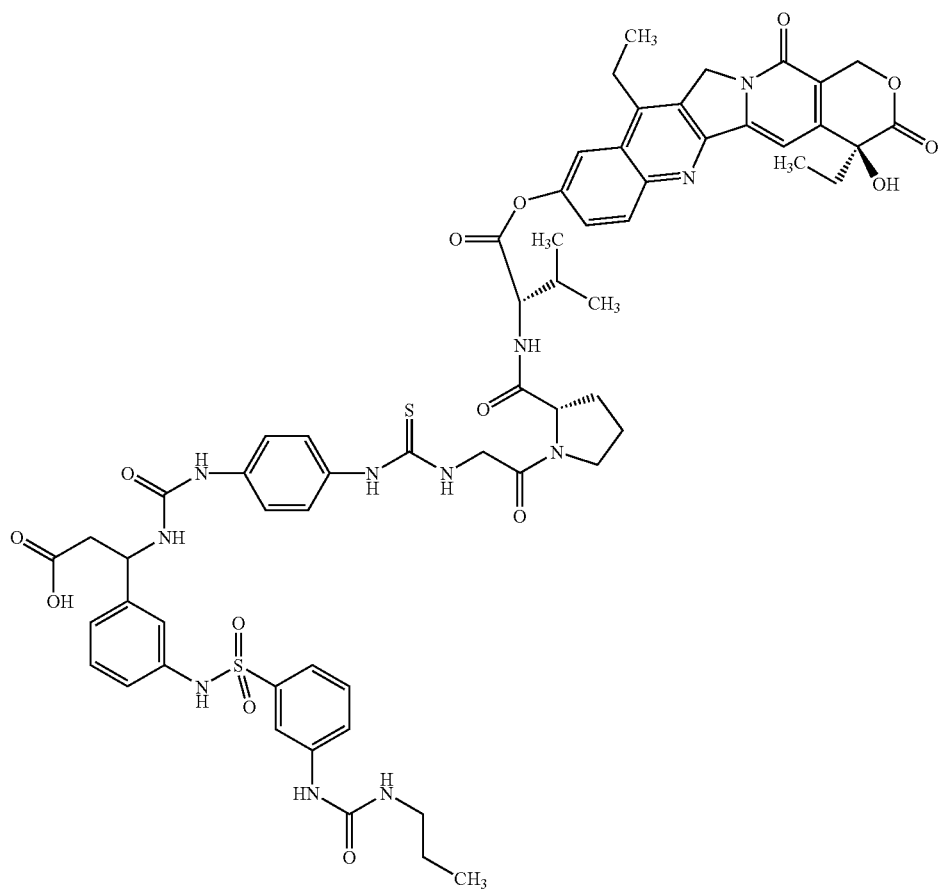
Diastereoisomer A:
Educts: I.17, II.2
Procedure: A
Example 11
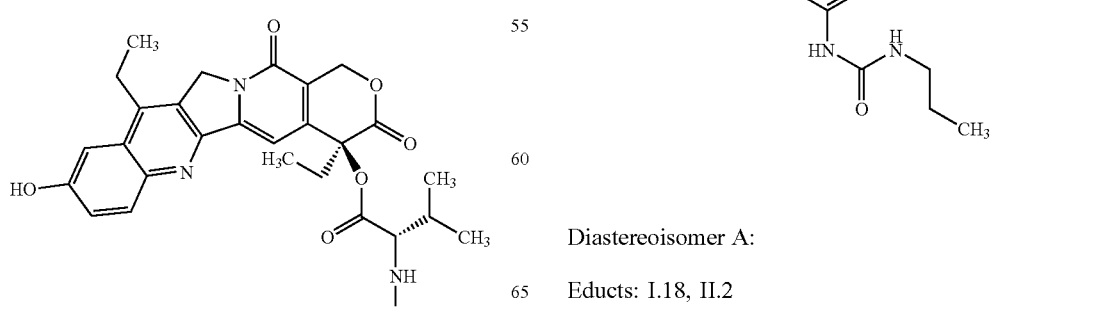
Diastereoisomer A:
Educts: I.18, II.2
Procedure: A

Example 12

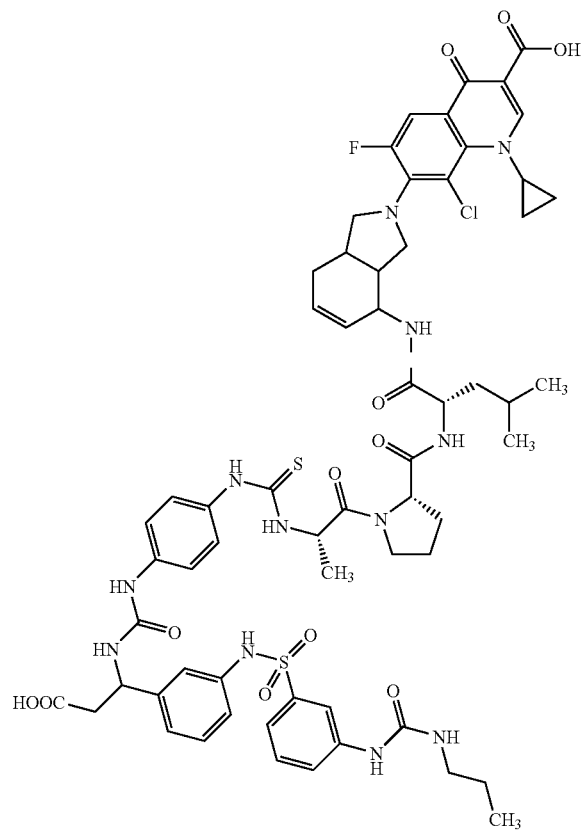

Diastereoisomer A:

Educts: I.12, II.2

Procedure: A, no transformation into sodium salt.

Purification by flash chromatography using acetonitrile/water (10/1) as eluent.

Yield: 36%

$R_f$=0.5[2)]

[ESI-LC-neg: m/e=1293=(M–H)⁻]

Biological Tests

A: $\alpha_v\beta_3$ Binding Test $\alpha_v\beta_3$ from human A375 cells was purified analogously to a procedure described by Wong et al. in Molecular Pharmacology 50, 529–537 (1996). In each case, 10 µL of $\alpha_v\beta_3$ (5 ng) in TBS pH 7.6, 2 mM $CaCl_2$, 1 mM $MgCl_2$, 1% n-octylglucopyranoside (Sigma); 10 µL of test substance in TBS pH 7.6, 0.1% DMSO and 45 µL of TBS pH 7.6, 2 mM $CaCl_2$, 1 mM $MgCl_2$, 1 mM $MnCl_2$ were incubated at room temperature for 1 h. In each case, 25 µL of WGA SPA beads (Amersham, 4 mg/ml) and 10 µL of echistatin (0.1 µCi, Amersham, chloramine-T labelled) were then added. After 16 h at room temperature, the samples were measured in a scintillation measuring apparatus (Wallac 1450). The test results are shown in Table 2 below.

TABLE 2

$IC_{50}$ values of the binding to the $\alpha_v\beta_3$ receptor

| Example | $IC_{50}$ [nM] |
|---|---|
| 1 | 8 |
| 2 | 800 |
| 3 | 15 |
| 4 | 500 |
| 5 | 30 |
| 6 | 100 |
| 7 | 100 |
| 12 | 30 |

B: Growth Inhibition Test for the Determination of the Cytotoxic Properties on Various Tumour Cell Lines The human large intestine cell lines SW 480 and HT29 (ATCC No. CCL 228) and HTB38 and the mouse melanoma cell line B16F10 (CRL 6475) were grown to confluence in Roux dishes in seromed® RPMI 1640 medium (from Biochrom KG, Berlin) with addition of 10% FCS. They were then trypsinized and taken up in RPMI plus 10% FCS to a cell count of 50,000 cells or, for B16F10, 20,000 cells per mL. 100 µL of cell suspension per well were added to a 96 microwell plate and incubated at 37° C. for 1 day in a $CO_2$ incubator. A further 100 µL of RPMI medium and 1 µL of DMSO were then added with the test substances. The growth was checked after day 6. For this purpose, 25 µL of MTT solution (3-(4,5-dimethylthiazol-2-yl)-2,5-diphenyltetrazolium bromide) were added to each well at a starting concentration of 5 mg/mL of water. The plate was incubated at 37° C. for 5 hours in a $CO_2$ incubator. The medium was then aspirated and 100 1L of i-propanol/well were added. After shaking with 100 µL of water for 30 min, the extinction was measured at 595 nm using a Multiplate Reader (BIO-RAD 3550-UV).

The cytostatic action is indicated in Table 3 as an $IC_{50}$ value, in each case for the individual cell lines.

TABLE 3

$IC_{50}$ values of the cytotoxic action on tumour cell lines

| | $IC_{50}$ [nM] | | |
|---|---|---|---|
| Example | SW480 | HT29 | B16F10 |
| 1 | 150 | 60 | 160 |
| 2 | 400 | 150 | 400 |
| 3 | 500 | 150 | 700 |
| 4 | 600 | 150 | 700 |
| 5 | 700 | 300 | 1000 |
| 6 | 400 | 200 | 600 |
| 7 | 600 | 350 | 1000 |
| 8 | 50 | 50 | 300 |
| 9 | 70 | 30 | 80 |
| 12 | 1000 | 600 | 2000 |

C. In-vivo Inhibition or Tumour Growth Using a Nude Mouse Model

Material

In all in-vivo experiments for investigating the inhibition of tumour growth, athymic nude mice (NMRI nu/nu strain) were used. The tumour was developed by serial passage in nude mice, The human origin of the tumour was confirmed by isoenzymatic and immunohistochemical methods.

Experimental Set-up:

The tumour was implanted subcutaneously in both flanks of nu/nu nude mice 6 to 8 weeks old. The treatment was started, depending on the doubling time, as soon as the tumours had reached a diameter of 5 to 7 mm. The mice were assigned to the treatment group or the control group (5 mice per group having 8 to 10 assessable tumours) by randomization. The individual tumours of the control group all grew progressively.

The size of the tumours was measured in two dimensions by means of a slide gauge. The tumour volume which correlated well with the cell count, was then used for all assessments. The volume was calculated according to the formula "length×breadth×breadth/2" ($[a \times b^2]/2$; a and b representing two diameters arranged at right angles).

The values of the relative tumour volume (RTV) were calculated for each individual tumour by dividing the tumour size on day X with the tumour size on day 0 (at the time of randomization). The average values of the RTV were then used for the further assessment.

The inhibition of the increase of the tumour volume (tumour volume of the test group/control group, T/C, in percent) was the final measured value.

Treatment:

The compounds can be administered with a daily or an intermittent therapy schedule through a couple of days either by intraperitoneal, intravenious, oral or subcutaneous route.

In a subcutaneously growing melanoma xenograft model (MEXF 989) the compounds of Examples 1 and 3 were tested and effected inhibitions of the tumour growth. The compounds are dissolved in 1% aqueous dextrose solution and administered intravenously from day 1–3 and day 15–17. The optimal calculated T/C values are given in Table 4.

TABLE 4

| Example | dose [mg/kg/day] | lethality | optimal T/C [%] |
|---|---|---|---|
| 1 | 18 | 1/5 | 7.2 |
| 1 | 24 | 1/5 | 3.2 |
| 3 | 6 | 0/5 | 10.3 |

Furthermore, in a subcutaneously growing renal xenograft model (RXF 944) the compounds of Examples 1 and 3 were tested and also effected inhibitions of the tumour growth. The compounds are dissolved in 1% aqueous dextrose solution and administered intravenously from day 1–3 and day 15–17. The optimal calculated T/C values are given in Table 5.

TABLE 5

| Example | dose [mg/kg/day] | lethality | optimal T/C [%] |
|---|---|---|---|
| 1 | 18 | 1/7 | 12.4 |
| 1 | 24 | 0/7 | 5.1 |
| 3 | 6 | 1/7 | 24.0 |
| camptothecin | 2.5 | 0/6 | 41.1 |
| topotecan | 1.8 | 0/7 | 47.8 |

Furthermore, in a subcutaneously growing breast cancer model (MX-1) the compounds of Examples 1 and 3 were tested and also effected inhibitions of the tumour growth. The compounds are dissolved in 1% aqueous dextrose solution and administered intravenously from day 1–3 and day 15–17. The optimal calculated T/C values are given in Table 6.

TABLE 6

| Example | dose [mg/kg/day] | lethality | optimal T/C [%] |
|---|---|---|---|
| 1 | 18 | 0/5 | 1.7 |
| 3 | 6 | 0/5 | 12.4 |

D. CSF-induced Proliferation of Hemopoietic Stem Cells

Bone marrow cells are flushed out of the femur of mice. $10^5$ cells are incubated in McCoy 5A medium (0.3% agar) together with recombinant murine GM-CSF (Genzyme; parent cell colony formation) and the substances ($10^{-4}$ to 100 µg/ml) at 37° C. and 7% $CO_2$. 7 days later, the colonies (<50 cells) and clusters (17–50 cells) are counted.

The compounds of Examples 1–4 were tested; they exhibit a drastically reduced toxicity against stem cells in vitro compared to camptothecin.

TABLE 7

IC$_{50}$ values of toxicity against hemopoietic stem cells

| Example | IC$_{50}$ [ng/ml] |
|---|---|
| 1 | 300 |
| 2 | 300 |
| 3 | 40 |
| 4 | 50 |
| Camptothecin | 3 |

E. Cleavage of Conjugates by Elastase in Culture Medium of HT29

TABLE 8

Ratio of peak areas of released camptothecin vs. conjugate after 24 hours hours incubation in the supernatant of HT29 supplemented with elastase

| Example | elastase mediated cleavage peak area product/educt |
|---|---|
| 1 | 43/53 |
| 2 | 33/63 |
| 3 | 96/1 |
| 4 | 93/4 |
| 6 | 91/0 |
| 7 | 95/0 |

What is claimed is:

1. A conjugate of the formula $$CT-LI-Sp_x-IA \qquad (I)$$

wherein

CT denotes a monovalent radical from the group of a cytotoxic radical, a radical of a cytostatic and a radical of a cytostatic derivative, which can each additionally carry a hydroxyl, carboxyl or amino group, LI is a group of formula -AA1-AA2-AA3-AA4$_q$- (III), wherein AA1 denotes a bivalent residue of valine, leucine or isoleucine;

AA2 denotes a bivalent proline residue,

AA3/AA4 independently from one another denote a bivalent residue of alanine, norvaline, histidine, glycine, asparagine or aspartate, and q denotes zero or 1, Sp denotes a thiocarbonyl group, x is zero or 1, IA denotes a monovalent non-peptide radical addressing an $\alpha_v\beta_3$ integrin receptor, which radical corresponds to the formula

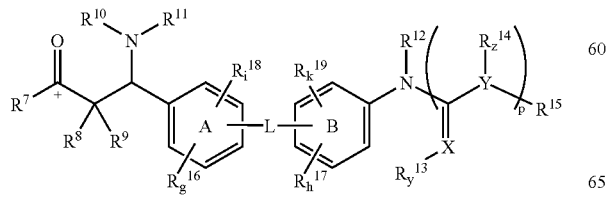

(II)

wherein the bond between radical (II) and Sp (if x=1) or LI (if x=zero) is located at one of the following alternatives:

a) between radical (II) and LI via the carbon atom which in formula (II) is marked with a cross, b) between radical (II) and Sp or LI (i) via Y (possible only, if p=1), (ii) via the nitrogen atom, to which $R^{10}$ is attached or (iii) via $R^{10}$, in which formula (II)

$R^7$ denotes hydroxyl, substituted or unsubstituted alkoxy, substituted or unsubstituted cycloalkoxy, substituted or unsubstituted aryloxy, or saturated or unsaturated, optionally substituted heterocyclyloxy or represents a single bond, in case the radical (II) is bonded to the rest of the conjugate directly via the carbon atom marked with a cross;

$R^8$ denotes hydrogen, hydroxyl, substituted or unsubstituted alkyl or alkoxy, substituted or unsubstituted cycloalkyl, substituted or unsubstituted aryl, saturated or unsaturated, substituted or unsubstituted heterocyclyl, substituted or unsubstituted alkenyl, substituted or unsubstituted alkynyl, or together with (i) $R^9$ and (ii) the carbon atom, to which $R^8$ is bonded, forms a substituted or unsubstituted carbocycle or heterocycle;

$R^9$ denotes hydrogen, hydroxyl, substituted or unsubstituted alkyl or alkoxy, substituted or unsubstituted cycloalkyl, substituted or unsubstituted alkenyl, substituted or unsubstituted alkynyl, substituted or unsubstituted aryl, saturated or unsaturated, substituted or unsubstituted heterocyclyl, or together with (i) $R^8$ and (ii) the carbon atom, to which $R^9$ is bonded, forms a substituted or unsubstituted carbocycle or heterocycle;

$R^{10}$ denotes
  a) one of the monovalent groups of $-SO_2R^{101}$, $-CO-R^{101}$, $-CO-OR^{102}$, $-CO-NR^{101}R^{103}$, $-CS-NR^{101}R^{103}$ in case the radical (II) is bonded to the rest of the conjugate directly via the carbon atom marked with a cross or via Y, or
  b) one of the bivalent groups of $-SO_2R^{101}$, $-CO-R^{101}$, $-COOR^{102}$, $-CO-NR^{101}R^{103}$, $-CS-NR^{101}R^{103}$ in case the radical (II) is bonded to the rest of the conjugate via $R^{10}$, or
  c) a single bond in case the radical (II) is bonded to the rest of the conjugate via the nitrogen atom, to which $R^{11}$ is bonded;

$R^{101}$ denotes
  a) substituted or unsubstituted alkyl, substituted or unsubstituted cycloalkyl, substituted or unsubstituted aryl, or saturated or unsaturated, substituted or unsubstituted heterocyclyl, in case the radical (II) is not bonded to the rest of the conjugate via $R^{101}$; or
  b) a bivalent group selected from substituted or unsubstituted alkylene, substituted or unsubstituted cycloalkylene, substituted or unsubstituted arylene, and saturated or unsaturated, substituted or unsubstituted heterocyclo-diyl, in case the radical (II) is bonded to the rest of the conjugate via $R^{101}$, $R^{102}$ denotes
  a) a monovalent group selected from substituted or unsubstituted alkyl, substituted or unsubstituted cycloalkyl, substituted or unsubstituted aryl, or saturated or unsaturated, substituted or unsubstituted heterocyclyl, in case the radical (II) is not bonded to the rest of the conjugate via $R^{102}$, or
  b) a bivalent group selected from substituted or unsubstituted alkylene, substituted or unsubstituted cycloalkylene, substituted or unsubstituted arylene, or saturated or unsaturated, substituted or unsubstituted heterocyclo-diyl, in case the radical (II) is bonded to the rest of the conjugate via $R^{102}$;

$R^{103}$ denotes hydrogen or one of the meanings of $R^{101}$;

$R^{11}$ denotes (i) hydrogen, (ii) substituted or unsubstituted alkyl, (iii) the radical of a saturated or unsaturated (non-aromatic or aromatic) cyclic compound which can contain up to 4 hetero atoms per molecule or (iv) alkyl, substituted with a radical of group (iii) above;

L denotes $-(CH_2)_nNHSO_2(CH_2)_o-$, $-(CH_2)_nSO_2NH(CH_2)_o-$, $-(CH_2)_nNHCO(CH_2)_o-$, $-(CH_2)_nCONH(CH_2)_o-$, $-(CH_2)_nOCH_2(CH_2)_o-$, $-(CH_2)_nCH_2O(CH_2)_o-$, $-(CH_2)_nCOO(CH_2)_o-$, $-(CH_2)_nOOC(CH_2)_o-$, $-(CH_2)_nCH_2CO(CH_2)_o-$, $-(CH_2)_nCOCH_2(CH_2)_o-$, $-NHCONH-$, $-(CH_2)_nSCH_2(CH_2)_o-$, $-(CH_2)_nCH_2S(CH_2)_o-$, $-(CH_2)_nCH_2SO(CH_2)_o-$, $-(CH_2)_nSOCH_2(CH_2)_o-$, $-(CH_2)_nCH_2SO_2(CH_2)_o-$ or $-(CH_2)_nSO_2CH_2(CH_2)_o-$, wherein n and o denote zero or 1 and wherein $n+o \leq 1$;

$R^{12}$ denotes hydrogen, substituted or unsubstituted alkyl, substituted or unsubstituted cycloalkyl, substituted or unsubstituted aryl, or saturated or unsaturated, substituted or unsubstituted heterocyclyl, or together with (i) one of $R^{15}$ (if present), $R^{13}$ or $R^{14}$ and (ii) the nitrogen atom, to which $R^{12}$ is bonded, forms saturated or unsaturated, substituted or unsubstituted heterocyclyl which can contain further hetero atoms;

X denotes N, O or S;

y denotes zero if X=O or S, and denotes 1 if X=N;

$R^{13}$ denotes hydrogen, substituted or unsubstituted alkyl, substituted or unsubstituted cycloalkyl, cyano, nitro, $-CO-R^{104}$ or $-CO-OR^{105}$, or together with (i) X and (ii) one of $R^{12}$, $R^{14}$ or $R^{15}$ forms substituted or unsubstituted heterocyclyl which can contain further hetero atoms;

$R^{104}$ denotes hydrogen, substituted or unsubstituted alkyl, substituted or unsubstituted cycloalkyl, substituted or unsubstituted aryl, or saturated or unsaturated, substituted or unsubstituted heterocyclyl which can contain further hetero atoms;

$R^{105}$ denotes one of the meanings of $R^{104}$;

Y denotes N or S;

$R^{14}$ denotes (i) hydrogen, (ii) substituted or unsubstituted alkyl, (iii) the radical of a saturated or unsaturated (non-aromatic or aromatic) cyclic compound which can contain up to 4 hetero atoms per molecule or (iv) alkyl, substituted with a radical of group (iii) above; or together with (i) Y and (ii) one of $R^{15}$ (if present), $R^{12}$ or $R^{13}$ forms a saturated or unsaturated, substituted or unsubstituted heterocyclyl which can contain further hetero atoms;

z denotes zero, if Y=S, and denotes 1, if Y=N;

p denotes zero or 1;

$R^{15}$ denotes hydrogen, substituted or unsubstituted alkyl, substituted or unsubstituted cycloalkyl, substituted or unsubstituted aryl, or saturated or unsaturated, substituted or unsubstituted heterocyclyl or together with (i) Y and (ii) one of $R^{14}$ (if p=z=1), $R^{12}$, or $R^{13}$ forms saturated or unsaturated, substituted or unsubstituted heterocyclyl which can contain further hetero atoms, or represents a single bond in case the radical (II) is bonded to the rest of the conjugate via Y;

$R^{16}$ to $R^{19}$ independently from each other denote cyano, halogen, substituted or unsubstituted alkyl or alkoxy, or substituted or unsubstituted cycloalkyl; and g, h, i, and k independently from each other denote zero or 1;

or a stereoisomer, hydrate, physiologically acceptable salt, or hydrate of said salt thereof.

2. The conjugate according to claim 1, wherein

CT denotes the radical of camptothecin or a camptothecin derivative, which is formally formed by the abstraction of the hydrogen atom from the hydroxyl group at its $C_{20}$-carbon atom or from a functional group present in the molecule;

LI and Sp are as defined in claim 1; and

IA is a non-peptide radical of the formula (II) addressing an $\alpha_v\beta_3$ integrin receptor, wherein $R^7$ denotes methoxy, ethoxy, propoxy, isopropoxy, butoxy, isobutoxy, tert-butoxy, pentoxy, isopentoxy, neopentoxy, hexoxy, cyclopropoxy, cyclopropylmethoxy, cyclobutoxy, cyclopentoxy, cyclohexoxy, phenoxy, tolyloxy, benzyloxy, or a substituted derivative thereof or hydroxyl or a single bond (in case the radical (II) is bonded to the rest of the conjugate via the carbon atom marked with a cross);

$R^8$ denotes hydrogen, hydroxyl, methyl, ethyl, propyl, isopropyl, butyl, isobutyl, tert-butyl, pentyl, isopentyl, neopentyl, hexyl, methoxy, ethoxy, propoxy, butoxy, pentoxy, hexoxy, cyclopropyl, cyclobutyl, cyclopentyl, cyclohexyl, cycloheptyl, phenyl, tolyl, benzyl, benzyloxy, or a substituted derivative thereof, or together with (i) $R^9$ and (ii) the carbon atom, to which $R^8$ is bonded, forms a substituted or unsubstituted 3- to 6-membered carbocycle or heterocycle;

$R^9$ denotes hydrogen, hydroxyl, methyl, ethyl, propyl, isopropyl, butyl, isobutyl, tert-butyl, pentyl, isopentyl, neopentyl, hexyl, methoxy, ethoxy, propoxy, butoxy, pentoxy, hexoxy, cyclopropyl, cyclobutyl, cyclopentyl, cyclohexyl, cycloheptyl, phenyl, tolyl, benzyl, or a substituted derivative thereof, or together with (i) $R^8$ and (ii) the carbon atom, to which $R^9$ is bonded, forms a substituted or unsubstituted 3- to 6-membered carbocycle or heterocycle;

$R^{10}$ is as defined in claim 1;

$R^{101}$ denotes a monovalent radical selected from methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, phenyl, tolyl, benzyl, or a substituted derivative thereof, $—C_6H_2(CH_3)_3$, $—C_6(CH_3)_5$, $—CH_2—C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 4-chlorophenylmethyl, 2,4-dichlorophenyl-methyl, 2,6-dichlorophenylmethyl, 3-aminophenyl, 4-aminophenyl, 4-carboxyphenyl,2-methoxycarbonylphenylmethyl, 3-trifluoromethylphenyl, 4-trifluoromethylphenyl, 3,5-bis(trifluoromethyl)-phenyl, 4-trifluoromethoxyphenyl, benzyl, 2-acetamido-4-methylthiazol-5-yl, phenylethyl, 1-phenylpropyl, (S)-(+)-camphor-10-yl, (R)-(−)-camphor-10-yl, 2-thiophenyl, 4-methoxyphenyl, 3,5-dimethoxyphenyl, 3-methylphenyl, 4-methylphenyl, 4-tert-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)-anilino, 4-acetamidophenyl, 2,2,2-trifluoroethyl, 5-chloro-3-methylbenzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methylisoxazol-3-yl, 1-adamantyl, 4-chlorophenoxymethyl, 2-chloropyridine-5-methyl, 5,7-dimethyl-1,3,4-triazaindolizin-2-yl, (S)-camphan-1-yl, (R)-camphan-1-yl or 8-quinolinyl, or a bivalent radical formally obtained by abstraction of a hydrogen from the above monovalent $R^{101}$ radicals, via which bivalent radical the radical (II) can be bonded to the rest of the conjugate;

$R^{102}$ denotes a monovalent radical selected from methyl, ethyl, propyl, isopropyl, butyl, isobutyl, tert-butyl, pentyl, isopentyl, neopentyl, hexyl; cyclopropyl, cyclobutyl, cyclopentyl, cyclohexyl, cycloheptyl; phenyl, tolyl, benzyl, or a substituted derivative thereof; $—C_6H_2(CH_3)_3$, $—C_6(CH_3)_5$, $—CH_2C_6H_2(CH_3)_3$, 2-chlorophenyl, 3-chlorophenyl, 4-chlorophenyl, 2,3-dichlorophenyl, 2,4-dichlorophenyl, 3,4-dichlorophenyl, 2,5-dichlorophenyl, 3,5-dichlorophenyl, 2,6-dichlorophenyl, 3-aminophenyl, 4-aminophenyl, 4-chlorophenylmethyl, 2,4-dichlorophenylmethyl, 2,6-dichlorophenylmethyl, 2-methoxycarbonylphenylmethyl, 3-trifluoromethylphenyl, 4-trifluoromethylphenyl, 3,5-bis(trifluoromethyl)phenyl, 4-trifluoromethoxyphenyl, 2-acetamido-4-methylthiazol-5-yl, phenylethyl, 1-phenylpropyl, (S)-(+)-camphor-10-yl, (R)-(−)-camphor-10-yl, 2-phenylethenyl, 2-thiophenyl, 4-methoxyphenyl, 3,5-dimethoxyphenyl, 3-methylphenyl, 4-methylphenyl, 4-tert-butylphenyl, 4-propylphenyl, 2,5-dimethylphenyl, 2-methoxy-5-methylphenyl, 2,3,5,6-tetramethylphenyl, 1-naphthyl, 2-naphthyl, 4-fluorophenyl, 2,4-difluorophenyl, 2-chloro-6-methylphenyl, 2-chloro-4-fluorophenyl, 2,5-dimethoxyphenyl, 3,4-dimethoxyphenyl, 3-chloro-6-methoxyphenyl, 2-trifluoromethylphenyl, 2-alkylsulphonylphenyl, 2-arylsulphonylphenyl, 3-(N-acetyl-6-methoxy)-aniline, 4-acetamidophenyl, 2,2,2-trifluoroethyl, 5-chloro-3-methyl-benzothiazol-2-yl, N-methoxycarbonyl-piperidin-3-yl, thiophen-2-yl, isoxazol-5-yl, ethoxy, 2-chloropyridin-3-yl, pyridin-3-yl, benzyloxy, 5-methyl-isoxazol-3-yl, 1-adamantyl, 4-chlorophenoxy-methyl, 2,2-dimethylethenyl, 2-chloropyridin-5-methyl, 5,7-dimethyl-1,3,4-triazaindolizin-2-yl, (S)-camphan-1-yl, (R)-camphan-1-yl or 8-quinolinyl, or a bivalent radical formally obtained by abstraction of a hydrogen from the above monovalent $R^{102}$ radicals, via which bivalent radical the radical (II) can be bonded to the rest of the conjugate;

$R^{103}$ denotes hydrogen or one of the meanings of $R^{101}$, via which radical $R^{103}$, if it is bivalent, the radical (II) can be bonded to the rest of the conjugate;

$R^{11}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methylhex-2-yl, amino-$C_{1-4}$-alkyl, $C_{1-4}$-alkylamino-$C_{1-4}$-alkyl, $C_{1-4}$-dialkylamino-$C_{1-4}$-alkyl or $C_{1-4}$-alkoxy-$C_{1-4}$-alkyl, phenyl, tolyl, benzyl, or a substituted derivative thereof, or one of the following radicals:

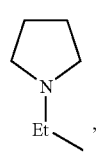
(a1)

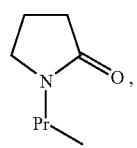
(a2)

-continued
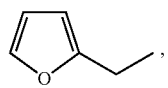 (a3)
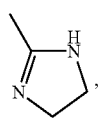 (a4)
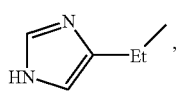 (a5)
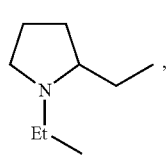 (a6)
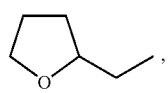 (a7)
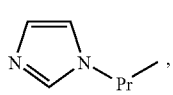 (a8)
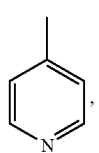 (a9)
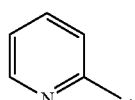 (a10)
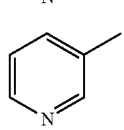 (a11)
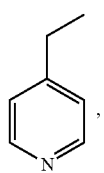 (a12)
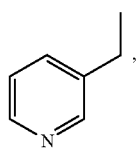 (a13)
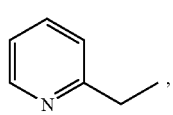 (a14)
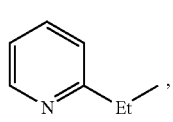 (a15)
-continued
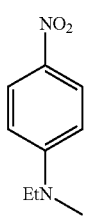 (a16)
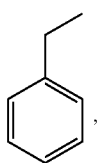 (a17)
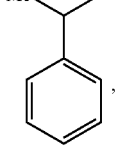 (a18)
 (a19)
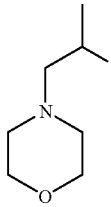 (a20)
 (a21)
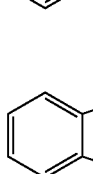 (a22)
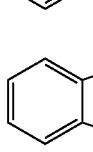 (a23)
(a24)

(a25)
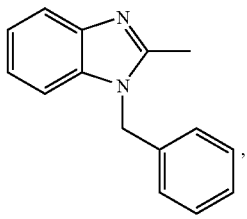, (a26)
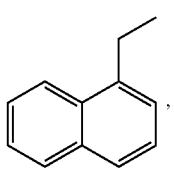, (a27)
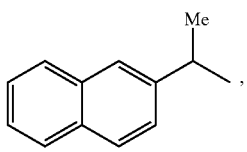, (a28)
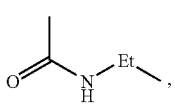,

L denotes —NHSO$_2$—, —CH$_2$NHSO$_2$—, —NHSO$_2$CH$_2$—, —SO$_2$—NH—, —CH$_2$SO$_2$NH—, —SO$_2$NHCH$_2$—, —NHCO—, —CH$_2$NH—CO—, —NHCOCH$_2$—, —CONH—, —CH$_2$CONH—, —CONHCH$_2$—, —OCH$_2$—, —CH$_2$OCH$_2$—, —OCH$_2$CH$_2$—, —CH$_2$O— or —CH$_2$CH$_2$O—;

$R^{12}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methyl-hex-2-yl, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$-alkyl, phenyl, tolyl, benzyl, or a substituted derivative thereof, or one of the radicals (a1) to (a28) or together with (i) one of $R^{15}$ (if present), $R^{13}$ or $R^{14}$, and (ii) the nitrogen atom, to which $R^{12}$ is bonded, forms a substituted or unsubstituted, saturated or unsaturated 4- to 6-membered heterocyclic residue which can contain further hetero atoms;

X denotes N, O or S;

p denotes zero or 1;

$R^{13}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, nitro, cyano, —COR$^{104}$, —CO—OR$^{105}$ or together with (i) X and (ii) one of $R^{12}$, $R^{14}$ or $R^{15}$ forms a substituted or unsubstituted 4- to 6-membered heterocycle which can contain further hetero atoms;

$R^{104}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, phenyl, tolyl, benzyl, or a substituted derivative thereof;

$R^{105}$ denotes one of the meanings of $R^{104}$,

Y denotes N or S;

$R^{14}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methyl-hex-2-yl, phenyl, tolyl, benzyl, or a substituted derivative thereof, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$-alkyl, one of the radicals (a1) to (a28), or together with (i) Y and (ii) one of $R^{15}$ (if present), $R^{12}$, or $R^{13}$ forms a saturated or unsaturated, substituted or unsubstituted 4- to 6-membered heterocyclic residue which can contain further hetero atoms; and $R^{15}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methyl-hex-2-yl, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$-alkyl, phenyl, tolyl, benzyl, or a substituted derivative thereof, one of the radicals (a1) to (a28) or together with (i) Y and (ii) one of $R^{14}$ (if p=z=1), $R^{12}$, or $R^{13}$ forms a saturated or unsaturated, substituted or unsubstituted 4- to 6-membered heterocyclic residue which can contain further hetero atoms, or represents a single bond in case the radical (II) is bonded to the rest of the conjugate via Y, and the other radicals are as defined in claim 1, or a stereoisomer, hydrate, physiologically acceptable salt, or hydrate of said salt thereof.

3. The conjugate according to claim 2, wherein
$R^7$ represents a single bond and
the radical (II) is bonded to the rest of the conjugate directly via the carbon atom marked with a cross,
and the other radicals of formula (II) are as defined in claim 2,
or a stereoisomer, hydrate, physiologically acceptable salt, or hydrate of said salt thereof.

4. The conjugate according to claim 2, wherein
$R^{15}$ represents a single bond via which the radical (II) is bonded to the rest of the conjugate,
and the other radicals of formula (II) are as defined in claim 2,
or a stereoisomer, hydrate, physiologically acceptable salt, or hydrate of said salt thereof.

5. The conjugate according to claim 2, wherein the radical (II) is bonded to the rest of the conjugate via $R^{10}$,
and the other radicals of formula (II) are as defined in claim 2,
or a stereoisomer, hydrate, physiologically acceptable salt, or hydrate of said salt thereof.

6. A conjugate of the formula $$CT-LI-Sp_x-IA \qquad (I)$$

wherein

CT denotes the radical of camptothecin or a camptothecin derivative, which is formally formed by the abstraction of the hydrogen atom from the hydroxyl group at its $C_{20}$-carbon atom or from a functional group present in the molecule;

LI is a group of formula -AA1-AA2-AA3-AA4$_q$- (III),
wherein
  AA1 denotes a bivalent residue of valine, leucine or isoleucine;
  AA2 denotes a bivalent proline residue,
  AA3/AA4 independently from one another denote a bivalent residue of alanine, norvaline, histidine, glycine, asparagine or aspartate,
  q denotes zero or 1,
x is 1;
Sp is a thiocarbonyl group,
IA is radical (II)

(II)

wherein
R$^7$ is hydroxyl,
R$^8$, R$^9$, R$^{12}$, and R$^{14}$ are hydrogen,
g, h, i, and k are zero, resulting in R$^{16}$ to R$^{19}$ being absent;
R$^{10}$ is —CO—NH-Ph-*NH— wherein the radical (II) is bonded to the rest of the conjugate via the nitrogen atom marked with a star, and
L is —NH—SO$_2$ linked to the adjacent phenylene units A and B such that each of these phenylene units is 1,3-substituted,
R$^{11}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methylhex-2-yl, amino-C$_{1-4}$-alkyl, C$_{1-4}$-alkylamino-C$_{1-4}$-alkyl, C$_{1-4}$-dialkylamino-C$_{1-4}$-alkyl or C$_{1-4}$-alkoxy-C$_{1-4}$-alkyl, phenyl, tolyl, benzyl, or a substituted derivative thereof, or one of the following radicals:

(a1)

(a2)

(a3)

-continued (a4)

(a5)

(a6)

(a7)

(a8)

(a9)

(a10)

(a11)

-continued (a12) 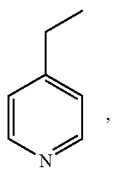

(a13) 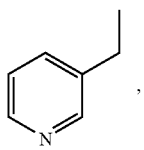

(a14) 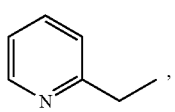

(a15) 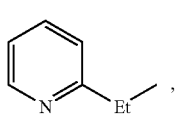

(a16) 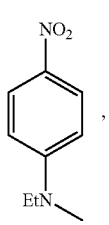

(a17) 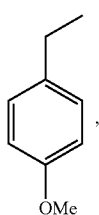

(a18) 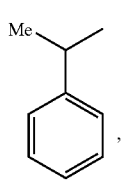

(a19) 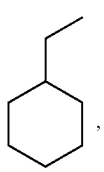

(a20) 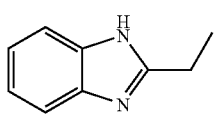

-continued (a21) 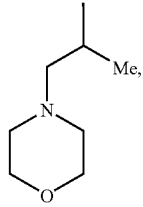

(a22) 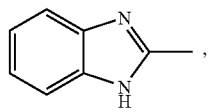

(a23) 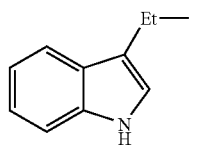

(a24) 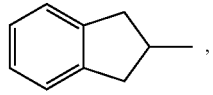

(a25) 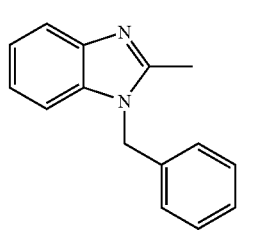

(a26) 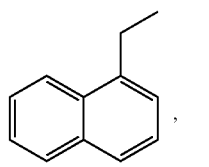

(a27) 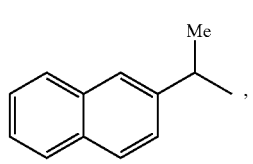

(a28) 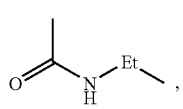

X denotes N, O, or S;
y denotes zero if X is O or S, and denotes 1 if X is N;
Y denotes N;
z denotes 1;
p denotes 0 or 1;
$R^{13}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, nitro, cyano, —$COR^{104}$, or —CO—$OR^{105}$,
wherein
$R^{104}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, phenyl, tolyl, benzyl, or a substituted derivative thereof; and $R^{105}$ denotes one of the meanings of $R^{104}$, $R^{15}$ denotes hydrogen, methyl, ethyl, propyl, isopropyl, butyl, isobutyl, tert-butyl, pentyl, isopentyl, neopentyl, hexyl, cyclopropyl, cyclobutyl, cyclopentyl, cyclohexyl, cycloheptyl, 4-methylcyclohexyl, 3,3,5-trimethylcyclohexyl, cyclopropylmethyl, 5-methylhex-2-yl, $C_{1-4}$-alkoxy-$C_{1-4}$-alkyl, amino-$C_{1-4}$-alkyl, $C_{1-4}$-alkylamino-$C_{1-4}$-alkyl, $C_{1-4}$-dialkylamino-$C_{1-4}$-alkyl, phenyl, tolyl, benzyl, or a substituted derivative thereof, or one of the radicals (a1) to (a28) or together with (i) Y and (ii) one of $R^{14}$ (if p=z=1), $R^{12}$, or $R^{13}$ forms a saturated or unsaturated, substituted or unsubstituted 4- to 6-membered heterocyclic residue which can contain further hetero atoms, or represents a single bond in case the radical (II) is bonded to the rest of the conjugate via Y, or a stereoisomer, hydrate, physiologically acceptable salt, or hydrate of said salt thereof.

7. A conjugate selected from the compounds having the following structures:

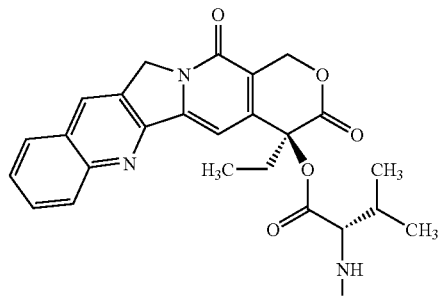

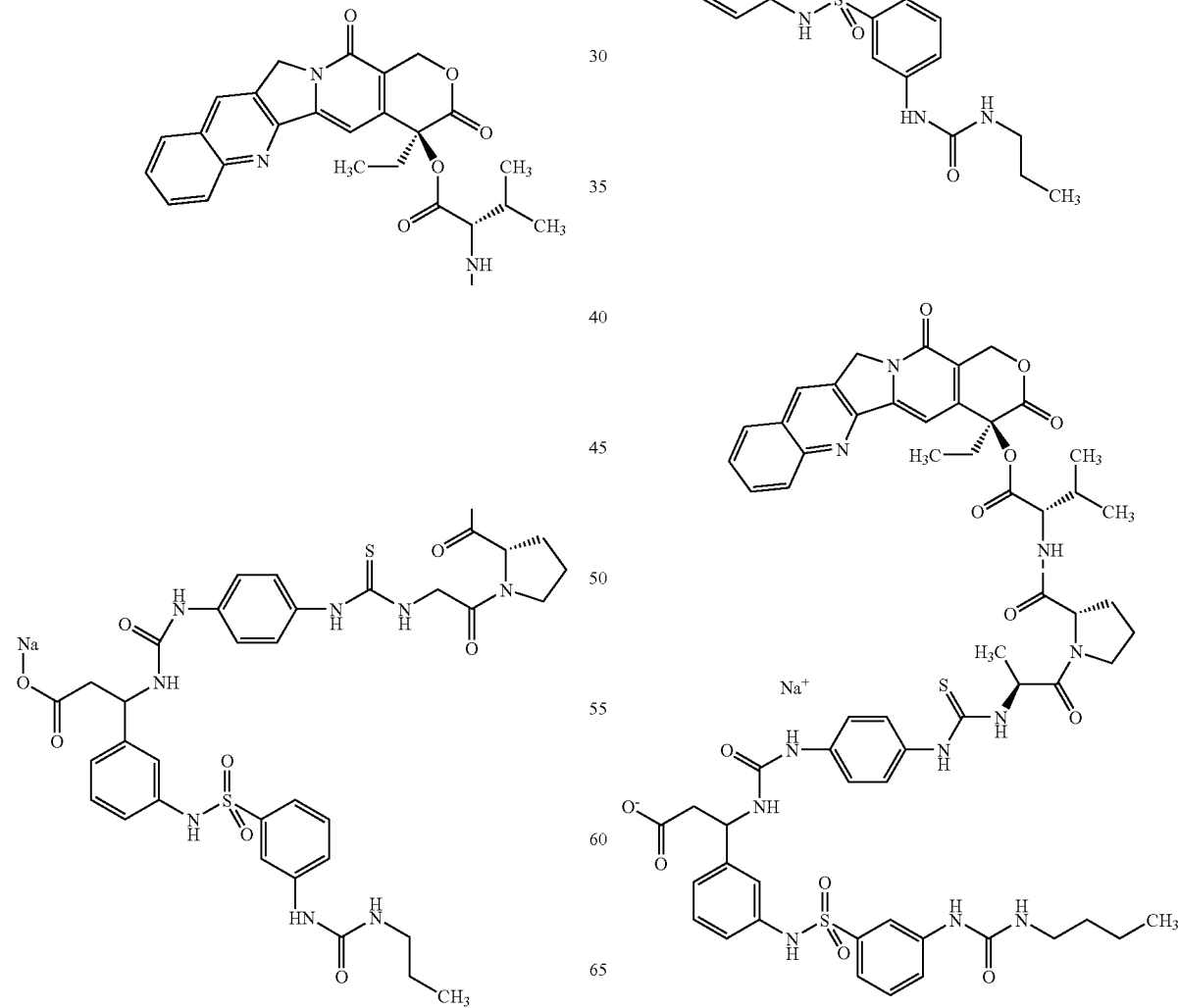

77
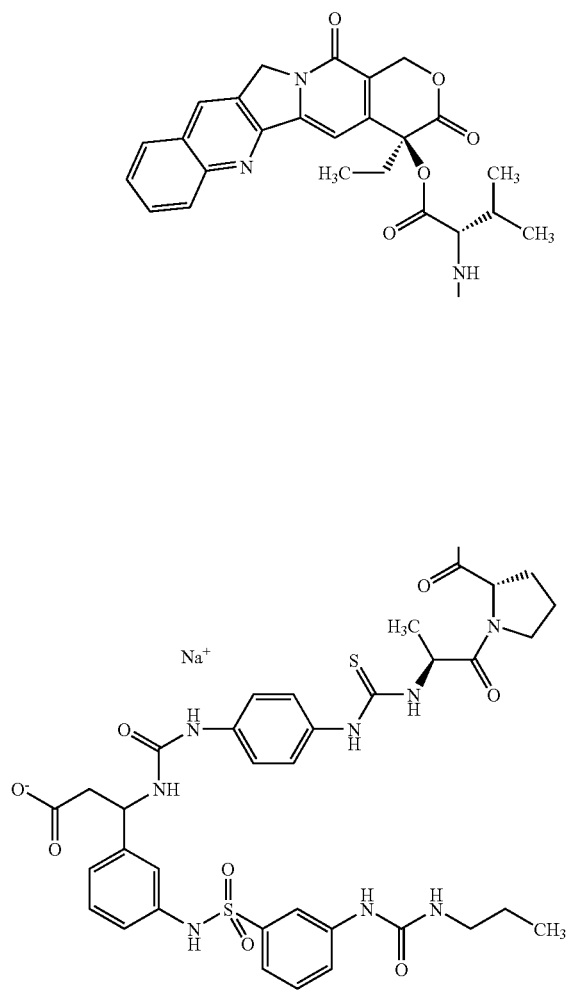
78
-continued
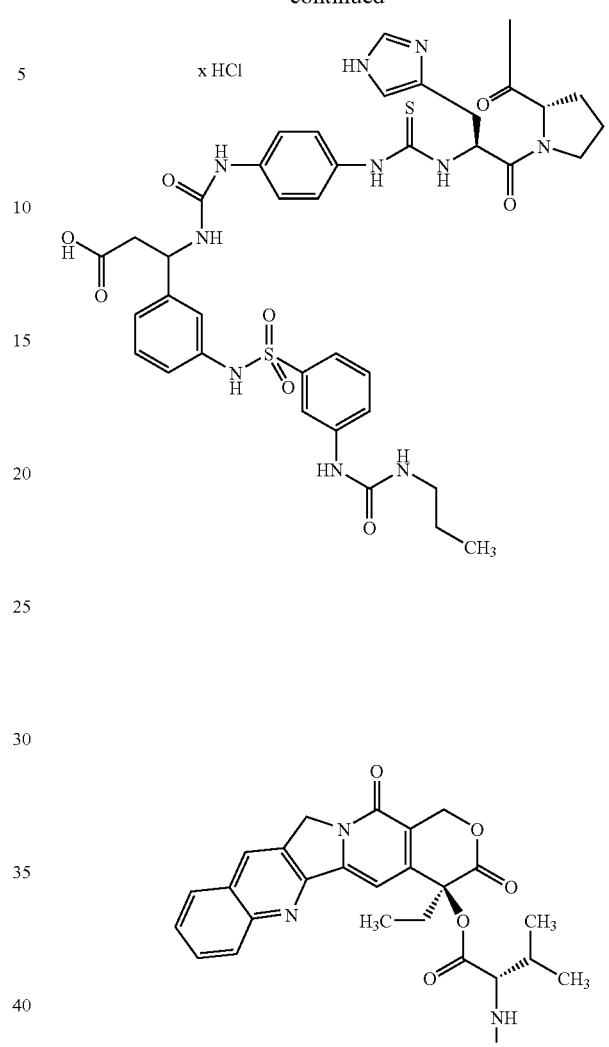
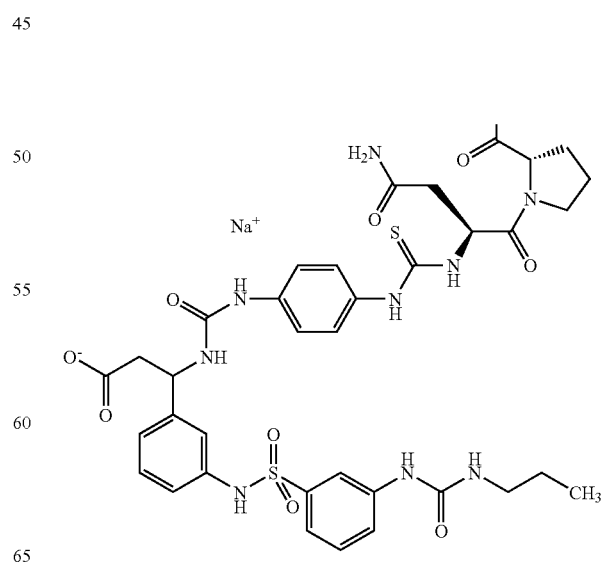

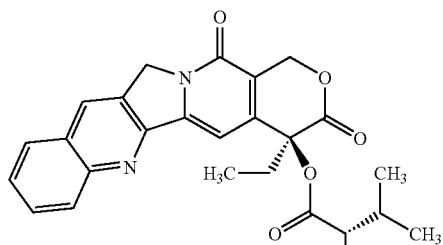
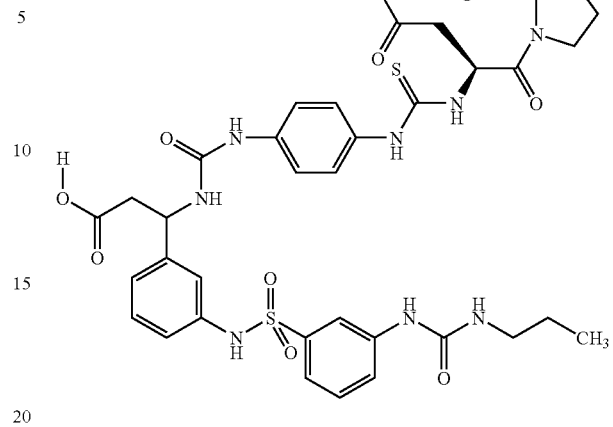
-continued
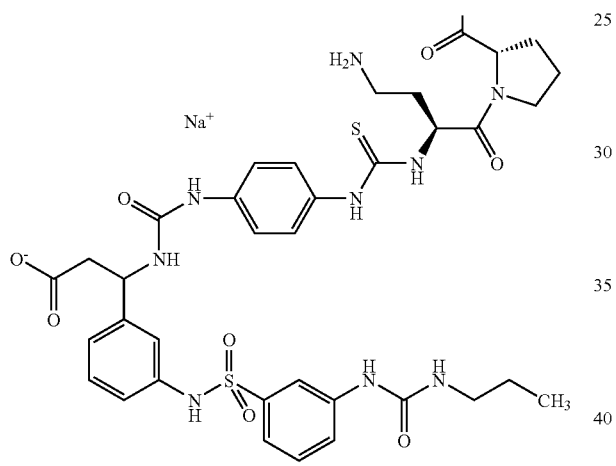
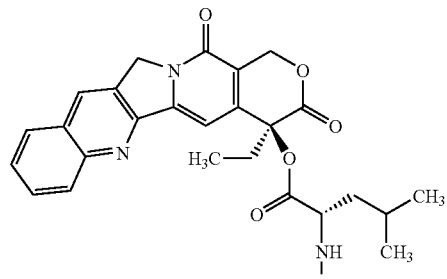
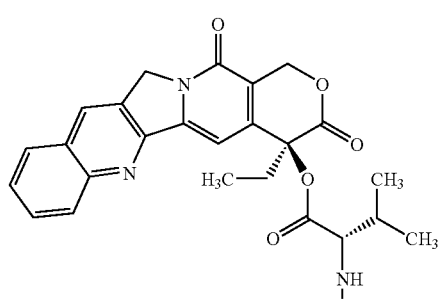
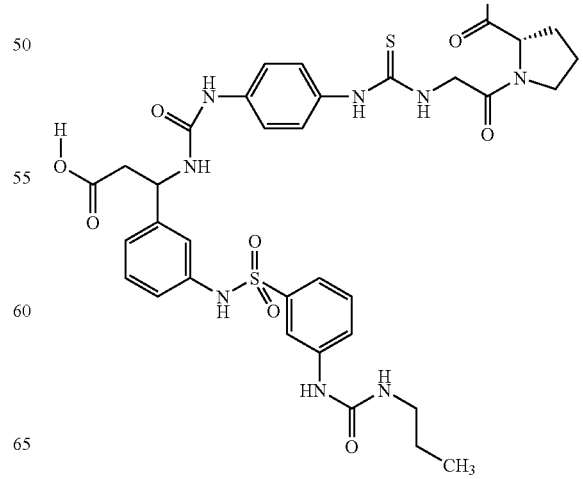

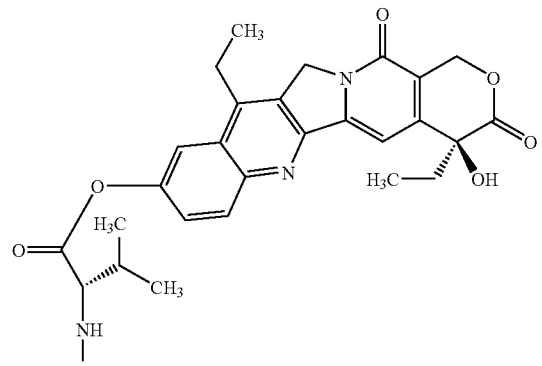
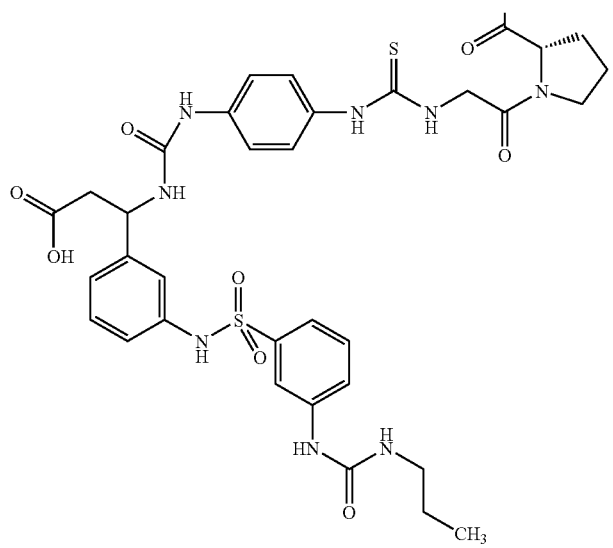

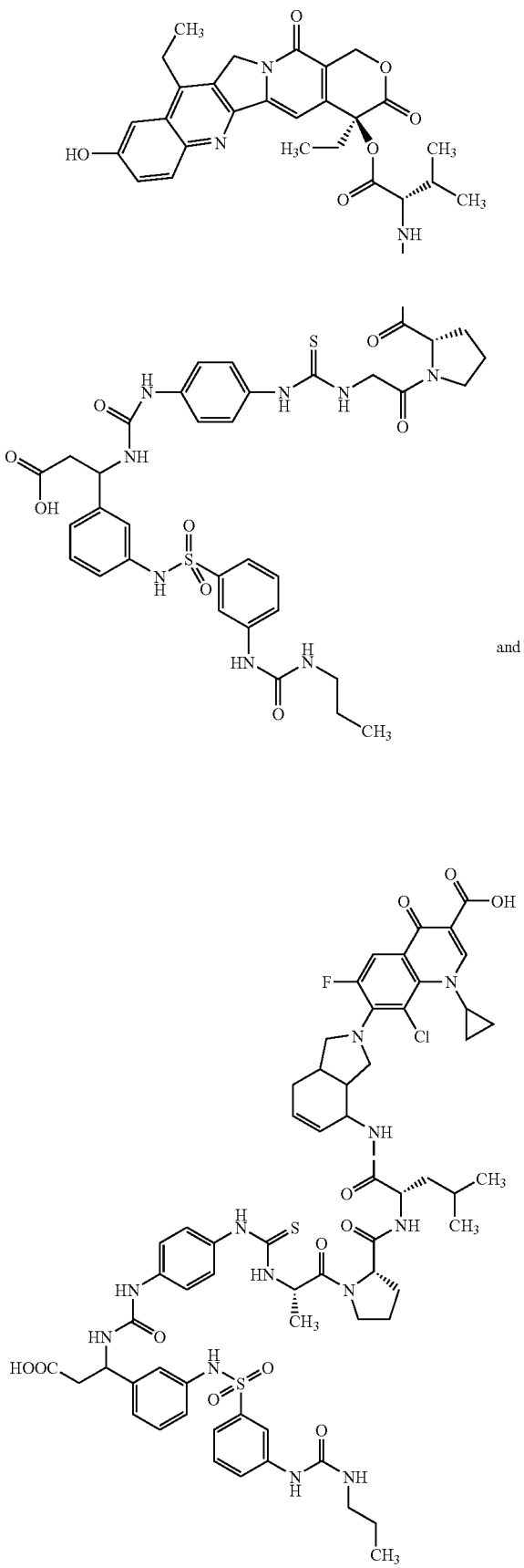

and or a stereoisomer, hydrate, physiologically acceptable salt, or hydrate of said salt thereof.

8. A process for preparing the conjugates of claim 1 comprising (A) (for conjugates (I) wherein x=zero) reacting a moiety comprising radical (II) which has a free or an activated carboxyl function, with a moiety comprising the unit CT-LI- which has a free primary or secondary amino group, or (B) reacting a moiety comprising radical (II) which has a free primary or secondary amino function, with a carbonic acid derivative, followed by the reaction with a moiety comprising the unit CT-LI- which has a free primary or secondary amino group, or (C) reacting a moiety comprising radical (II) which contains a free primary or secondary amino function, with a moiety comprising the unit CT-LI- which contains a free or activated carboxyl function, wherein all radicals throughout (A) to (C) have the meanings of formula (I) in claim 1.

9. A method for the treatment of cancer comprising administering to a host in need thereof an effective amount of a conjugate according to claim 1, 2, 3, 4, 5, 6, or 7.

10. A pharmaceutical composition comprising as an active ingredient an effective amount of at least one of the conjugates according to claim 1, 2, 3, 4, 5, 6, or 7 and at least one pharmacologically acceptable formulating agent.

11. A method of manufacturing a pharmaceutical composition by combining at least one of the conjugates according to claim 1, 2, 3, 4, 5, 6, or 7 with at least one pharmacologically acceptable formulating agent.

12. A pharmaceutical composition comprising as an active ingredient an effective amount of at least one of the conjugates according to claim 1, 2, 3, 4, 5, 6, or 7 and at least one pharmaceutical active ingredient which is different from the conjugates according to claims 1 to 7.

13. A pharmaceutical composition in dosage unit form comprising an effective amount of a conjugate according to claim 1, 2, 3, 4, 5, 6, or 7 and an inert pharmaceutical carrier.

14. A method of treating cancer in mammals comprising the administration of an effective amount of at least one conjugate according to claim 1, 2, 3, 4, 5, 6, or 7 either alone or in admixture with a diluent or pharmaceutical carrier.

15. The conjugate of claim 2, wherein in the definition of CT, said functional group present in the molecule is an amino or hydroxy group.

16. The conjugate of claim 6, wherein in the definition of CT, said functional group present in the molecule is an amino or hydroxy group.

17. The process of claim 8, wherein in alternative (B) the carbonic acid derivative is phosgene, thio-phosgene or a chloroformic acid ester.

* * * * *